United States Patent
Park

(10) Patent No.: US 12,390,645 B1
(45) Date of Patent: *Aug. 19, 2025

(54) SPINAL CORD MODULATION FOR INHIBITING PAIN VIA SHORT PULSE WIDTH WAVEFORMS, AND ASSOCIATED SYSTEMS AND METHODS

(71) Applicant: Nevro Corp., Redwood City, CA (US)

(72) Inventor: Sangsoo Wesley Park, San Jose, CA (US)

(73) Assignee: Nevro Corp., Redwood City, CA (US)

( * ) Notice: Subject to any disclaimer, the term of this patent is extended or adjusted under 35 U.S.C. 154(b) by 195 days.

This patent is subject to a terminal disclaimer.

(21) Appl. No.: 17/739,653

(22) Filed: May 9, 2022

Related U.S. Application Data

(60) Continuation of application No. 16/781,960, filed on Feb. 4, 2020, now abandoned, which is a continuation of application No. 16/048,131, filed on Jul. 27, 2018, now Pat. No. 10,569,089, which is a division of application No. 14/534,769, filed on Nov. 6, 2014, now Pat. No. 10,149,978.

(60) Provisional application No. 61/901,255, filed on Nov. 7, 2013.

(51) Int. Cl.
*A61N 1/36* (2006.01)
*A61N 1/05* (2006.01)

(52) U.S. Cl.
CPC ..... *A61N 1/36175* (2013.01); *A61N 1/36062* (2017.08); *A61N 1/36157* (2013.01); *A61N 1/36171* (2013.01); *A61N 1/0553* (2013.01); *A61N 1/36071* (2013.01)

(58) Field of Classification Search
CPC ............. A61N 1/0553; A61N 1/36157; A61N 1/36171; A61N 1/36071; A61N 1/36175
See application file for complete search history.

(56) References Cited

U.S. PATENT DOCUMENTS

| | | |
|---|---|---|
| 1,597,061 A | 8/1926 | Cultra |
| 2,622,601 A | 12/1952 | Nemec |
| 3,195,540 A | 7/1965 | Waller |
| 3,724,467 A | 4/1973 | Avery et al. |
| 3,727,616 A | 4/1973 | Lenzkes |
| 3,817,254 A | 6/1974 | Maurer |
| 3,822,708 A | 7/1974 | Zilber |

(Continued)

FOREIGN PATENT DOCUMENTS

| | | |
|---|---|---|
| CN | 101175530 | 5/2008 |
| DE | 10318071 A1 | 11/2004 |

(Continued)

OTHER PUBLICATIONS

U.S. Appl. No. 61/171,790, filed Apr. 22, 2009, Walker et al.

(Continued)

*Primary Examiner* — Joseph M Dietrich

(57) ABSTRACT

Short pulse width spinal cord modulation for inhibiting pain with reduced side effects and associated systems and methods are disclosed. In particular embodiments, modulation signal has pulse widths in the range of from about 10 microseconds to about 50 microseconds may be applied to the patient's spinal cord region to address chronic pain without using paresthesia or tingling to mask or cover the patient's sensation of pain. In other embodiments, modulation in accordance with similar parameters can be applied to other spinal or peripheral locations to address other indications.

29 Claims, 8 Drawing Sheets

(56) References Cited

U.S. PATENT DOCUMENTS

| | | |
|---|---|---|
| 3,893,463 A | 7/1975 | Williams |
| 4,014,347 A | 3/1977 | Halleck et al. |
| 4,023,574 A | 5/1977 | Nemec |
| 4,055,190 A | 10/1977 | Tany et al. |
| 4,148,321 A | 4/1979 | Wyss et al. |
| 4,379,462 A | 4/1983 | Borkan et al. |
| 4,414,986 A | 11/1983 | Dickhudt et al. |
| 4,535,777 A | 8/1985 | Castel |
| 4,541,432 A | 9/1985 | Molina-Negro et al. |
| 4,608,985 A | 9/1986 | Crish et al. |
| 4,612,934 A | 9/1986 | Borkan et al. |
| 4,649,935 A | 3/1987 | Charmillot et al. |
| 4,735,204 A | 4/1988 | Sussman et al. |
| 4,764,132 A | 8/1988 | Stutz, Jr. |
| 4,793,353 A | 12/1988 | Borkan et al. |
| 4,841,973 A | 6/1989 | Stecker |
| RE33,420 E | 11/1990 | Sussman et al. |
| 5,002,053 A | 3/1991 | Garcia-Rill |
| 5,058,584 A | 10/1991 | Bourgeois |
| 5,335,657 A | 8/1994 | Terry, Jr. et al. |
| 5,354,320 A | 10/1994 | Schaldach et al. |
| 5,514,175 A | 5/1996 | Kim et al. |
| 5,540,734 A | 7/1996 | Zabara |
| 5,562,717 A | 10/1996 | Tippey et al. |
| 5,643,330 A | 7/1997 | Holsheimer et al. |
| 5,716,377 A | 2/1998 | Rise et al. |
| 5,755,758 A | 5/1998 | Wolozko |
| 5,776,170 A | 7/1998 | MacDonald et al. |
| 5,830,151 A | 11/1998 | Hadzic et al. |
| 5,853,373 A | 12/1998 | Griffith et al. |
| 5,893,883 A | 4/1999 | Torgerson et al. |
| 5,938,690 A | 8/1999 | Law |
| 5,983,141 A | 11/1999 | Sluijter et al. |
| 5,995,872 A | 11/1999 | Bourgeois |
| 6,002,964 A | 12/1999 | Feler et al. |
| 6,014,588 A | 1/2000 | Fitz |
| 6,027,456 A | 2/2000 | Feler et al. |
| 6,049,701 A | 4/2000 | Sparksman |
| 6,161,044 A | 12/2000 | Silverstone |
| 6,161,048 A | 12/2000 | Sluijter et al. |
| 6,167,311 A | 12/2000 | Rezai |
| 6,176,242 B1 | 1/2001 | Rise |
| 6,233,488 B1 | 5/2001 | Hess |
| 6,236,892 B1 | 5/2001 | Feler et al. |
| 6,238,423 B1 | 5/2001 | Bardy |
| 6,246,912 B1 | 6/2001 | Sluijter et al. |
| 6,319,241 B1 | 11/2001 | King et al. |
| 6,341,236 B1 | 1/2002 | Osorio et al. |
| 6,356,786 B1 | 3/2002 | Rezai et al. |
| 6,366,814 B1 | 4/2002 | Boveja |
| 6,393,325 B1 | 5/2002 | Mann et al. |
| 6,397,108 B1 | 5/2002 | Camps et al. |
| 6,405,079 B1 | 6/2002 | Ansarinia |
| 6,421,566 B1 | 7/2002 | Holsheimer |
| 6,440,090 B1 | 8/2002 | Schallhorn |
| 6,473,644 B1 | 10/2002 | Terry, Jr. et al. |
| 6,505,078 B1 | 1/2003 | King et al. |
| 6,510,347 B2 | 1/2003 | Borkan |
| 6,516,227 B1 | 2/2003 | Meadows et al. |
| 6,526,318 B1 | 2/2003 | Ansarinia |
| 6,571,127 B1 | 5/2003 | Ben-Haim et al. |
| 6,584,358 B2 | 6/2003 | Carter et al. |
| 6,587,724 B2 | 7/2003 | Mann |
| 6,609,030 B1 | 8/2003 | Rezai et al. |
| 6,622,048 B1 | 9/2003 | Mann et al. |
| 6,659,968 B1 | 12/2003 | McClure |
| 6,662,051 B1 | 12/2003 | Eraker et al. |
| 6,714,822 B2 | 3/2004 | King et al. |
| 6,721,603 B2 | 4/2004 | Zabara et al. |
| 6,795,737 B2 | 9/2004 | Gielen et al. |
| 6,856,315 B2 | 2/2005 | Eberlein |
| 6,862,479 B1 | 3/2005 | Whitehurst |
| 6,871,090 B1 | 3/2005 | He et al. |
| 6,871,099 B1 | 3/2005 | Whitehurst et al. |
| 6,885,888 B2 | 4/2005 | Rezai |
| 6,892,097 B2 | 5/2005 | Holsheimer et al. |
| 6,907,293 B2 | 6/2005 | Grill et al. |
| 6,907,295 B2 | 6/2005 | Gross et al. |
| 6,923,784 B2 | 8/2005 | Stein |
| 6,928,230 B2 | 8/2005 | Squibbs |
| 6,928,320 B2 | 8/2005 | King |
| 6,944,501 B1 | 9/2005 | Pless |
| 6,950,707 B2 | 9/2005 | Whitehurst |
| 6,959,215 B2 | 10/2005 | Gliner |
| 6,968,237 B2 | 11/2005 | Doan et al. |
| 6,990,376 B2 | 1/2006 | Tanagho et al. |
| 7,024,246 B2 | 4/2006 | Acosta et al. |
| 7,047,079 B2 | 5/2006 | Erickson |
| 7,054,686 B2 | 5/2006 | MacDonald |
| 7,082,333 B1 | 7/2006 | Bauhahn et al. |
| 7,117,034 B2 | 10/2006 | Kronberg |
| 7,146,223 B1 | 12/2006 | King |
| 7,146,224 B2 | 12/2006 | King |
| 7,149,574 B2 | 12/2006 | Yun et al. |
| 7,162,304 B1 | 1/2007 | Bradley |
| 7,167,750 B2 | 1/2007 | Knudson et al. |
| 7,174,215 B2 | 2/2007 | Bradley |
| 7,177,702 B2 | 2/2007 | Wallace et al. |
| 7,180,760 B2 | 2/2007 | Varrichio et al. |
| 7,206,640 B1 | 4/2007 | Overstreet |
| 7,212,865 B2 | 5/2007 | Cory |
| 7,225,035 B2 | 5/2007 | Brabec et al. |
| 7,236,822 B2 | 6/2007 | Dobak, III |
| 7,236,830 B2 | 6/2007 | Gliner |
| 7,239,912 B2 | 7/2007 | Dobak, III |
| 7,252,090 B2 | 8/2007 | Goetz |
| 7,260,436 B2 | 8/2007 | Kilgore et al. |
| 7,266,412 B2 | 9/2007 | Stypulkowski |
| 7,288,062 B2 | 10/2007 | Spiegel |
| 7,313,440 B2 | 12/2007 | Miesel |
| 7,324,852 B2 | 1/2008 | Barolat et al. |
| 7,326,181 B2 | 2/2008 | Katims |
| 7,333,857 B2 | 2/2008 | Campbell |
| 7,337,005 B2 | 2/2008 | Kim et al. |
| 7,346,398 B2 | 3/2008 | Gross et al. |
| 7,349,743 B2 | 3/2008 | Tadlock |
| RE40,279 E | 4/2008 | Sluijter et al. |
| 7,359,751 B1 | 4/2008 | Erickson et al. |
| 7,363,076 B2 | 4/2008 | Yun et al. |
| 7,389,145 B2 | 6/2008 | Kilgore et al. |
| 7,393,351 B2 | 7/2008 | Woloszko et al. |
| 7,463,927 B1 | 12/2008 | Chaouat |
| 7,483,747 B2 | 1/2009 | Gliner et al. |
| 7,493,172 B2 | 2/2009 | Whitehurst et al. |
| 7,502,652 B2 | 3/2009 | Gaunt et al. |
| 7,571,007 B2 | 8/2009 | Erickson et al. |
| 7,580,753 B2 | 8/2009 | Kim et al. |
| 7,599,737 B2 | 10/2009 | Yomtov et al. |
| 7,634,317 B2 | 12/2009 | Ben-David et al. |
| 7,676,269 B2 | 3/2010 | Yun et al. |
| 7,689,276 B2 | 3/2010 | Dobak |
| 7,689,289 B2 | 3/2010 | King |
| 7,715,915 B1 | 5/2010 | Rye et al. |
| 7,734,340 B2 | 6/2010 | De Ridder |
| 7,734,355 B2 | 6/2010 | Cohen et al. |
| 7,742,810 B2 | 6/2010 | Moffitt et al. |
| 7,761,170 B2 | 7/2010 | Kaplan et al. |
| 7,778,704 B2 | 8/2010 | Rezai |
| 7,792,591 B2 | 9/2010 | Rooney et al. |
| 7,801,604 B2 | 9/2010 | Brockway et al. |
| 7,813,803 B2 | 10/2010 | Heruth et al. |
| 7,826,901 B2 | 11/2010 | Lee et al. |
| 7,853,322 B2 | 12/2010 | Bourget et al. |
| 7,860,570 B2 | 12/2010 | Whitehurst et al. |
| 7,865,243 B1 | 1/2011 | Whitehurst et al. |
| 7,877,136 B1 | 1/2011 | Moffitt et al. |
| 7,877,146 B1 | 1/2011 | Rezai |
| 7,890,176 B2 | 2/2011 | Jaax et al. |
| 7,890,182 B2 | 2/2011 | Parramon et al. |
| 7,914,452 B2 | 3/2011 | Hartley et al. |
| 7,933,654 B2 | 4/2011 | Merfeld et al. |
| 7,937,145 B2 | 5/2011 | Dobak |
| 8,000,794 B2 | 8/2011 | Lozano |
| 8,010,198 B2 | 8/2011 | Libbus et al. |

(56) References Cited

U.S. PATENT DOCUMENTS

| | | |
|---|---|---|
| 8,010,203 B2 | 8/2011 | DeMulling et al. |
| 8,027,718 B2 | 9/2011 | Spinner et al. |
| 8,046,075 B2 | 10/2011 | Rezai |
| 8,060,208 B2 | 11/2011 | Kilgore et al. |
| 8,082,039 B2 | 12/2011 | Kim et al. |
| 8,103,341 B2 | 1/2012 | Libbus et al. |
| 8,150,531 B2 | 4/2012 | Skelton |
| 8,170,658 B2 | 5/2012 | Dacey et al. |
| 8,170,675 B2 | 5/2012 | Alataris et al. |
| 8,180,445 B1 | 5/2012 | Moffitt |
| 8,209,021 B2 | 6/2012 | Alataris et al. |
| 8,209,028 B2 | 6/2012 | Skelton et al. |
| 8,224,453 B2 | 7/2012 | De Ridder |
| 8,224,459 B1 | 7/2012 | Pianca et al. |
| 8,255,048 B2 | 8/2012 | Dal Molin et al. |
| 8,280,515 B2 | 10/2012 | Greenspan |
| 8,301,241 B2 | 10/2012 | Ternes et al. |
| 8,340,775 B1 | 12/2012 | Cullen et al. |
| 8,355,792 B2 | 1/2013 | Alataris et al. |
| 8,359,102 B2 | 1/2013 | Alataris et al. |
| 8,359,103 B2 | 1/2013 | Alataris et al. |
| 8,364,271 B2 | 1/2013 | De Ridder |
| 8,364,273 B2 | 1/2013 | De Ridder |
| 8,396,559 B2 | 3/2013 | Alataris et al. |
| 8,412,338 B2 | 4/2013 | Faltys |
| 8,423,147 B2 | 4/2013 | Alataris et al. |
| 8,428,735 B2 | 4/2013 | Littlewood et al. |
| 8,428,748 B2 | 4/2013 | Alataris et al. |
| 8,467,875 B2 | 6/2013 | Bennett et al. |
| 8,483,830 B2 | 7/2013 | Tweden |
| 8,569,935 B1 | 10/2013 | Kosierkiewicz |
| 8,577,458 B1 | 11/2013 | Libbus et al. |
| 8,612,018 B2 | 12/2013 | Gillbe |
| 8,649,874 B2 | 2/2014 | Alataris et al. |
| 8,666,506 B2 | 3/2014 | King |
| 8,688,212 B2 | 4/2014 | Libbus et al. |
| 8,691,877 B2 | 4/2014 | Yun et al. |
| 8,712,534 B2 | 4/2014 | Wei |
| 8,751,009 B2 | 6/2014 | Wacnik |
| 8,768,469 B2 | 7/2014 | Tweden et al. |
| 8,805,512 B1 | 8/2014 | Greiner et al. |
| 8,825,164 B2 | 9/2014 | Tweden et al. |
| 8,825,166 B2 | 9/2014 | John |
| 8,886,326 B2 | 11/2014 | Alataris et al. |
| 8,886,328 B2 | 11/2014 | Alataris et al. |
| 8,892,209 B2 | 11/2014 | Alataris et al. |
| 8,918,172 B2 | 12/2014 | Moffitt et al. |
| 8,918,190 B2 | 12/2014 | Libbus et al. |
| 8,918,191 B2 | 12/2014 | Libbus et al. |
| 8,923,964 B2 | 12/2014 | Libbus et al. |
| 8,923,990 B2 | 12/2014 | Libbus et al. |
| 8,965,521 B2 | 2/2015 | Birkholz et al. |
| 8,996,125 B2 | 3/2015 | Greiner et al. |
| 9,002,457 B2 | 4/2015 | Hamann et al. |
| 9,002,459 B2 | 4/2015 | Lee et al. |
| 9,026,214 B2 | 5/2015 | Ternes et al. |
| 9,026,215 B2 | 5/2015 | Rossing |
| 9,026,226 B2 | 5/2015 | Gerber et al. |
| 9,067,076 B2 | 6/2015 | Nolan et al. |
| 9,101,770 B2 | 8/2015 | Arcot-Krishnamurthy et al. |
| 9,126,044 B2 | 9/2015 | Kramer et al. |
| 9,132,272 B2 | 9/2015 | Alves et al. |
| 9,180,298 B2 | 11/2015 | Alataris et al. |
| 9,205,258 B2 | 12/2015 | Simon et al. |
| 9,211,410 B2 | 12/2015 | Levine et al. |
| 9,295,840 B1 | 3/2016 | Thacker |
| 9,308,370 B2 | 4/2016 | Lima et al. |
| 9,327,127 B2 | 5/2016 | Alataris et al. |
| 9,370,659 B2 | 6/2016 | Franke et al. |
| 9,381,356 B2 | 7/2016 | Parker |
| 9,403,007 B2 | 8/2016 | Moekelke et al. |
| 9,421,355 B2 | 8/2016 | Colborn |
| 9,440,074 B2 | 9/2016 | Ternes et al. |
| 9,462,398 B2 | 10/2016 | De Ridder |
| 9,480,846 B2 | 11/2016 | Strother |
| 9,533,153 B2 | 1/2017 | Libbus et al. |
| 9,555,248 B2 | 1/2017 | De Ridder |
| 9,561,366 B2 | 2/2017 | Wei et al. |
| 9,561,370 B2 | 2/2017 | Rezai |
| 9,572,983 B2 | 2/2017 | Levine et al. |
| 9,694,183 B2 | 7/2017 | Grandhe |
| 9,700,724 B2 | 7/2017 | Liu et al. |
| 9,724,509 B2 | 8/2017 | Su et al. |
| 9,724,511 B2 | 8/2017 | Wei et al. |
| 9,724,513 B2 | 8/2017 | Lane et al. |
| 9,833,614 B1 | 12/2017 | Gliner |
| 9,895,532 B2 | 2/2018 | Kaula et al. |
| 9,895,539 B1 | 2/2018 | Heit |
| 9,913,980 B2 | 3/2018 | Ostroff et al. |
| 9,950,173 B2 | 4/2018 | Doan |
| 9,968,732 B2 | 5/2018 | Drew et al. |
| 10,029,102 B2 | 7/2018 | Doan |
| 10,076,668 B2 | 9/2018 | De Ridder |
| 10,092,758 B2 | 10/2018 | De Ridder |
| 10,149,978 B1 | 12/2018 | Park |
| 10,188,856 B1 | 1/2019 | Libbus et al. |
| 10,207,109 B2 | 2/2019 | Zhu et al. |
| 10,220,205 B2 | 3/2019 | Bhadra et al. |
| 10,328,256 B1 | 6/2019 | Gliner |
| 10,328,264 B2 | 6/2019 | Hamann et al. |
| 10,463,861 B2 | 11/2019 | Ternes et al. |
| 10,485,975 B2 | 11/2019 | Greiner et al. |
| 10,493,275 B2 | 12/2019 | Alataris |
| 10,537,740 B2 | 1/2020 | Cabunaru |
| 10,556,112 B1 | 2/2020 | Park |
| 10,561,845 B2 | 2/2020 | Giftakis et al. |
| 10,569,089 B1 | 2/2020 | Park |
| 10,576,286 B1 | 3/2020 | Park |
| 10,632,300 B2 | 4/2020 | Wagenbach et al. |
| 10,675,468 B2 | 6/2020 | Torgerson |
| 10,898,714 B2 | 1/2021 | Libbus et al. |
| 11,045,649 B2 | 6/2021 | Wei et al. |
| 11,229,792 B2 | 1/2022 | Alataris |
| 11,235,153 B2 | 2/2022 | Kibler et al. |
| 11,446,504 B1 | 9/2022 | Lee |
| 11,759,638 B2 | 9/2023 | Alataris |
| 2002/0055779 A1 | 5/2002 | Andrews |
| 2002/0087201 A1 | 7/2002 | Firlik et al. |
| 2002/0128700 A1 | 9/2002 | Cross |
| 2003/0036783 A1 | 2/2003 | Bauhahn |
| 2003/0100931 A1 | 5/2003 | Mullett |
| 2003/0120323 A1 | 6/2003 | Meadows et al. |
| 2003/0135248 A1 | 7/2003 | Stypulkowski |
| 2003/0204221 A1 | 10/2003 | Rodriguez et al. |
| 2004/0015202 A1 | 1/2004 | Chandler et al. |
| 2004/0034394 A1 | 2/2004 | Woods et al. |
| 2004/0039425 A1 | 2/2004 | Greenwood-Van Meerveld |
| 2004/0059395 A1 | 3/2004 | North et al. |
| 2004/0073273 A1 | 4/2004 | Gluckman et al. |
| 2004/0093093 A1 | 5/2004 | Andrews |
| 2004/0116977 A1 | 6/2004 | Finch et al. |
| 2004/0116978 A1 | 6/2004 | Bradley |
| 2004/0122477 A1 | 6/2004 | Whitehorse |
| 2004/0158298 A1 | 8/2004 | Gliner |
| 2004/0158839 A1 | 8/2004 | Gliner et al. |
| 2004/0162590 A1 | 8/2004 | Whitehurst et al. |
| 2004/0167584 A1 | 8/2004 | Carroll et al. |
| 2004/0186532 A1 | 9/2004 | Tadlock |
| 2004/0193228 A1 | 9/2004 | Gerber |
| 2004/0210270 A1 | 10/2004 | Erickson |
| 2004/0210271 A1 | 10/2004 | Campen et al. |
| 2004/0267330 A1 | 12/2004 | Lee et al. |
| 2005/0021104 A1 | 1/2005 | DiLorenzo |
| 2005/0033381 A1 | 2/2005 | Carter et al. |
| 2005/0038489 A1 | 2/2005 | Grill |
| 2005/0060001 A1 | 3/2005 | Singhal et al. |
| 2005/0070982 A1 | 3/2005 | Heruth et al. |
| 2005/0113877 A1 | 5/2005 | Spinelli et al. |
| 2005/0113878 A1 | 5/2005 | Gerber |
| 2005/0113882 A1 | 5/2005 | Cameron et al. |
| 2005/0119713 A1 | 6/2005 | Whitehurst et al. |
| 2005/0143783 A1 | 6/2005 | Boveja |
| 2005/0143789 A1 | 6/2005 | Whitehurst et al. |
| 2005/0149148 A1 | 7/2005 | King |

(56) References Cited

U.S. PATENT DOCUMENTS

| | | |
|---|---|---|
| 2005/0153885 A1 | 7/2005 | Yun et al. |
| 2005/0154435 A1 | 7/2005 | Stern et al. |
| 2005/0222641 A1 | 10/2005 | Pless |
| 2005/0240241 A1 | 10/2005 | Yun et al. |
| 2005/0245978 A1 | 11/2005 | Varrichio et al. |
| 2005/0245987 A1 | 11/2005 | Woods |
| 2005/0246006 A1 | 11/2005 | Daniels |
| 2005/0267545 A1 | 12/2005 | Cory |
| 2005/0278000 A1 | 12/2005 | Strother et al. |
| 2005/0288721 A1 | 12/2005 | Girouard |
| 2006/0004422 A1 | 1/2006 | De Ridder |
| 2006/0009820 A1 | 1/2006 | Royle |
| 2006/0015153 A1 | 1/2006 | Gliner et al. |
| 2006/0030895 A1 | 2/2006 | Simon et al. |
| 2006/0041285 A1 | 2/2006 | Johnson |
| 2006/0074456 A1 | 4/2006 | Pyles et al. |
| 2006/0079937 A1 | 4/2006 | King et al. |
| 2006/0095088 A1 | 5/2006 | De Ridder |
| 2006/0100671 A1 | 5/2006 | Ridder |
| 2006/0149337 A1 | 7/2006 | John |
| 2006/0161219 A1 | 7/2006 | Mock et al. |
| 2006/0161235 A1 | 7/2006 | King |
| 2006/0167512 A1 | 7/2006 | Ross et al. |
| 2006/0167525 A1 | 7/2006 | King |
| 2006/0168805 A1 | 8/2006 | Hegland et al. |
| 2006/0190044 A1 | 8/2006 | Libbus et al. |
| 2006/0190048 A1 | 8/2006 | Gerber |
| 2006/0224187 A1 | 10/2006 | Bradley et al. |
| 2006/0229687 A1 | 10/2006 | Goetz et al. |
| 2006/0253182 A1 | 11/2006 | King |
| 2006/0271108 A1 | 11/2006 | Libbus et al. |
| 2007/0021803 A1 | 1/2007 | Deem et al. |
| 2007/0032827 A1 | 2/2007 | Katims |
| 2007/0039625 A1 | 2/2007 | Heruth et al. |
| 2007/0043400 A1 | 2/2007 | Donders et al. |
| 2007/0049988 A1 | 3/2007 | Carbunaru |
| 2007/0049991 A1 | 3/2007 | Klostermann et al. |
| 2007/0060954 A1 | 3/2007 | Cameron et al. |
| 2007/0066997 A1 | 3/2007 | He et al. |
| 2007/0073353 A1 | 3/2007 | Rooney et al. |
| 2007/0073354 A1 | 3/2007 | Knudson et al. |
| 2007/0083240 A1 | 4/2007 | Peterson et al. |
| 2007/0100388 A1 | 5/2007 | Gerber |
| 2007/0106337 A1 | 5/2007 | Errico et al. |
| 2007/0106342 A1 | 5/2007 | Schumann |
| 2007/0150029 A1 | 6/2007 | Bourget et al. |
| 2007/0150034 A1 | 6/2007 | Rooney et al. |
| 2007/0156183 A1 | 7/2007 | Rhodes |
| 2007/0167992 A1 | 7/2007 | Carley |
| 2007/0179559 A1 | 8/2007 | Giftakis et al. |
| 2007/0179579 A1 | 8/2007 | Feler et al. |
| 2007/0191902 A1 | 8/2007 | Errico |
| 2007/0203537 A1 | 8/2007 | Goetz et al. |
| 2007/0213789 A1 | 9/2007 | Nolan et al. |
| 2007/0239226 A1 | 10/2007 | Overstreet |
| 2007/0244522 A1 | 10/2007 | Overstreet |
| 2007/0255118 A1 | 11/2007 | Miesel et al. |
| 2007/0265675 A1 | 11/2007 | Lund |
| 2007/0265681 A1 | 11/2007 | Gerber et al. |
| 2007/0293893 A1 | 12/2007 | Stolen et al. |
| 2007/0299482 A1 | 12/2007 | Littlewood et al. |
| 2008/0033511 A1 | 2/2008 | Dobak |
| 2008/0046012 A1 | 2/2008 | Covalin et al. |
| 2008/0065158 A1 | 3/2008 | Ben-Ezra |
| 2008/0086036 A1 | 4/2008 | Hartley |
| 2008/0097539 A1 | 4/2008 | Belalcazar |
| 2008/0103570 A1 | 5/2008 | Gerber |
| 2008/0167697 A1 | 7/2008 | Johnson |
| 2008/0183259 A1 | 7/2008 | Bly et al. |
| 2008/0234791 A1 | 9/2008 | Arle et al. |
| 2008/0269854 A1 | 10/2008 | Hegland et al. |
| 2008/0281381 A1 | 11/2008 | Gerber et al. |
| 2008/0300449 A1 | 12/2008 | Gerber |
| 2008/0319511 A1 | 12/2008 | Pless |
| 2009/0018617 A1 | 1/2009 | Skelton et al. |
| 2009/0024187 A1 | 1/2009 | Erickson et al. |
| 2009/0024189 A1 | 1/2009 | Lee et al. |
| 2009/0036945 A1 | 2/2009 | Chancellor et al. |
| 2009/0054962 A1 | 2/2009 | Lefler et al. |
| 2009/0069803 A1 | 3/2009 | Starkebaum |
| 2009/0076565 A1 | 3/2009 | Surwit |
| 2009/0083070 A1 | 3/2009 | Giftakis |
| 2009/0112282 A1 | 4/2009 | Kast et al. |
| 2009/0118777 A1 | 5/2009 | Iki |
| 2009/0125079 A1 | 5/2009 | Armstrong et al. |
| 2009/0132010 A1 | 5/2009 | Kronberg |
| 2009/0132016 A1 | 5/2009 | Putz |
| 2009/0157141 A1 | 6/2009 | Chiao et al. |
| 2009/0157149 A1 | 6/2009 | Wahlgren et al. |
| 2009/0196472 A1 | 8/2009 | Goetz et al. |
| 2009/0198306 A1 | 8/2009 | Goetz et al. |
| 2009/0204173 A1 | 8/2009 | Fang et al. |
| 2009/0204192 A1 | 8/2009 | Carlton et al. |
| 2009/0264789 A1 | 10/2009 | Molnar |
| 2009/0281595 A1 | 11/2009 | King et al. |
| 2009/0287274 A1 | 11/2009 | De Ridder |
| 2009/0287279 A1 | 11/2009 | Parramon et al. |
| 2009/0326611 A1 | 12/2009 | Gillbe |
| 2010/0010567 A1 | 1/2010 | Deem et al. |
| 2010/0016929 A1 | 1/2010 | Prochazka |
| 2010/0036454 A1 | 2/2010 | Bennett et al. |
| 2010/0042193 A1 | 2/2010 | Slavin |
| 2010/0057178 A1 | 3/2010 | Simon |
| 2010/0094375 A1 | 4/2010 | Donders et al. |
| 2010/0125313 A1 | 5/2010 | Lee et al. |
| 2010/0137938 A1 | 6/2010 | Kishawi et al. |
| 2010/0152817 A1 | 6/2010 | Gillbe |
| 2010/0191307 A1 | 7/2010 | Fang et al. |
| 2010/0198298 A1 | 8/2010 | Glukhovsky |
| 2010/0241190 A1 | 9/2010 | Kilgore et al. |
| 2010/0249875 A1 | 9/2010 | Kishawi et al. |
| 2010/0256696 A1 | 10/2010 | Schleicher et al. |
| 2010/0274312 A1 | 10/2010 | Alataris et al. |
| 2010/0274314 A1 | 10/2010 | Alataris et al. |
| 2010/0274315 A1 | 10/2010 | Alataris et al. |
| 2010/0274316 A1 | 10/2010 | Alataris et al. |
| 2010/0274317 A1 | 10/2010 | Parker et al. |
| 2010/0274318 A1 | 10/2010 | Walker et al. |
| 2010/0274320 A1 | 10/2010 | Torgerson |
| 2010/0274326 A1 | 10/2010 | Chitre et al. |
| 2010/0324630 A1 | 12/2010 | Lee et al. |
| 2010/0331916 A1 | 12/2010 | Parramon et al. |
| 2011/0009919 A1 | 1/2011 | Carbunaru et al. |
| 2011/0009923 A1 | 1/2011 | Lee |
| 2011/0009927 A1 | 1/2011 | Parker et al. |
| 2011/0022114 A1 | 1/2011 | Navarro |
| 2011/0040291 A1 | 2/2011 | Weissenrieder-Norlin et al. |
| 2011/0071589 A1 | 3/2011 | Starkebaum et al. |
| 2011/0184301 A1 | 7/2011 | Holmstrom et al. |
| 2011/0184486 A1 | 7/2011 | De Ridder |
| 2011/0184488 A1 | 7/2011 | De Ridder |
| 2011/0201977 A1 | 8/2011 | Tass |
| 2011/0276107 A1 | 11/2011 | Simon et al. |
| 2011/0282412 A1 | 11/2011 | Glukhovsky et al. |
| 2012/0010680 A1 | 1/2012 | Wei |
| 2012/0016437 A1 | 1/2012 | Alataris et al. |
| 2012/0016438 A1 | 1/2012 | Alataris et al. |
| 2012/0016439 A1 | 1/2012 | Alataris et al. |
| 2012/0083857 A1 | 4/2012 | Bradley |
| 2012/0089200 A1 | 4/2012 | Ranu et al. |
| 2012/0150252 A1 | 6/2012 | Feldman et al. |
| 2012/0203304 A1 | 8/2012 | Alataris et al. |
| 2012/0209349 A1 | 8/2012 | Alataris et al. |
| 2012/0277833 A1 | 11/2012 | Gerber et al. |
| 2012/0283797 A1 | 11/2012 | De Ridder |
| 2013/0006325 A1 | 1/2013 | Woods et al. |
| 2013/0023951 A1 | 1/2013 | Greenspan |
| 2013/0041425 A1 | 2/2013 | Fang et al. |
| 2013/0066411 A1 | 3/2013 | Thacker et al. |
| 2013/0079840 A1 | 3/2013 | Su et al. |
| 2013/0079841 A1 | 3/2013 | Su |
| 2013/0096643 A1 | 4/2013 | Fang et al. |
| 2013/0096644 A1 | 4/2013 | Fang et al. |
| 2013/0110196 A1 | 5/2013 | Alataris et al. |

(56) References Cited

U.S. PATENT DOCUMENTS

| | | |
|---|---|---|
| 2013/0123879 A1 | 5/2013 | Alataris et al. |
| 2013/0172955 A1 | 7/2013 | Alataris |
| 2013/0204173 A1 | 8/2013 | Kelly et al. |
| 2013/0204320 A1 | 8/2013 | Alataris et al. |
| 2013/0204321 A1 | 8/2013 | Alataris et al. |
| 2013/0204322 A1 | 8/2013 | Alataris et al. |
| 2013/0204323 A1 | 8/2013 | Thacker et al. |
| 2013/0204324 A1 | 8/2013 | Alataris et al. |
| 2013/0204338 A1 | 8/2013 | Alataris et al. |
| 2013/0211487 A1 | 8/2013 | Fang et al. |
| 2013/0237948 A1 | 9/2013 | Donders |
| 2013/0261695 A1 | 10/2013 | Thacker et al. |
| 2013/0261696 A1 | 10/2013 | Alataris et al. |
| 2013/0261697 A1 | 10/2013 | Alataris et al. |
| 2013/0282078 A1 | 10/2013 | Wacnik |
| 2013/0289659 A1 | 10/2013 | Nelson |
| 2014/0005744 A1 | 1/2014 | Hershey |
| 2014/0031896 A1 | 1/2014 | Alataris et al. |
| 2014/0142656 A1 | 5/2014 | Alataris et al. |
| 2014/0142657 A1 | 5/2014 | Alataris et al. |
| 2014/0142658 A1 | 5/2014 | Alataris et al. |
| 2014/0142659 A1 | 5/2014 | Alataris et al. |
| 2014/0142673 A1 | 5/2014 | Alataris et al. |
| 2014/0316484 A1 | 10/2014 | Edgerton |
| 2014/0343622 A1 | 11/2014 | Alataris et al. |
| 2014/0379044 A1 | 12/2014 | Walker et al. |
| 2015/0012079 A1 | 1/2015 | Goroszeniuk et al. |
| 2015/0018896 A1 | 1/2015 | Alataris et al. |
| 2015/0032181 A1 | 1/2015 | Baynham |
| 2015/0032182 A1 | 1/2015 | Alataris et al. |
| 2015/0032183 A1 | 1/2015 | Alataris et al. |
| 2015/0039040 A1 | 2/2015 | Cowan et al. |
| 2015/0039049 A1 | 2/2015 | Alataris et al. |
| 2015/0039050 A1 | 2/2015 | Alataris et al. |
| 2015/0045853 A1 | 2/2015 | Alataris et al. |
| 2015/0045854 A1 | 2/2015 | Alataris et al. |
| 2015/0051664 A1 | 2/2015 | Alataris et al. |
| 2015/0051665 A1 | 2/2015 | Hershey et al. |
| 2015/0073510 A1 | 3/2015 | Perryman |
| 2015/0202444 A1 | 7/2015 | Franke et al. |
| 2015/0217116 A1 | 8/2015 | Parramon et al. |
| 2015/0343220 A1 | 12/2015 | Alataris et al. |
| 2016/0114165 A1 | 4/2016 | Levine |
| 2016/0121119 A1 | 5/2016 | Alataris et al. |
| 2016/0256689 A1 | 9/2016 | Vallejo et al. |
| 2016/0263376 A1 | 9/2016 | Yoo et al. |
| 2016/0287872 A1 | 10/2016 | Alataris et al. |
| 2016/0287873 A1 | 10/2016 | Alataris et al. |
| 2016/0287874 A1 | 10/2016 | Alataris et al. |
| 2016/0287875 A1 | 10/2016 | Thacker et al. |
| 2016/0287888 A1 | 10/2016 | Alataris et al. |
| 2016/0303374 A1 | 10/2016 | Alataris et al. |
| 2016/0339239 A1 | 11/2016 | Yoo et al. |
| 2017/0001003 A1 | 1/2017 | Pivonka |
| 2017/0036020 A1 | 2/2017 | Harrah |
| 2017/0050021 A1 | 2/2017 | Cosman, Sr. |
| 2017/0087369 A1 | 3/2017 | Bokil |
| 2017/0095669 A1 | 4/2017 | Libbus et al. |
| 2017/0128722 A1 | 5/2017 | Perez |
| 2017/0165485 A1 | 6/2017 | Sullivan et al. |
| 2017/0216602 A1 | 8/2017 | Waataja et al. |
| 2017/0239470 A1 | 8/2017 | Wei et al. |
| 2017/0274209 A1 | 9/2017 | Edgerton |
| 2017/0348526 A1 | 12/2017 | Southwell |
| 2018/0256906 A1 | 9/2018 | Pivonka |
| 2018/0272132 A1 | 9/2018 | Subbaroyan |
| 2019/0001135 A1 | 1/2019 | Yoo et al. |
| 2019/0321641 A1 | 10/2019 | Baldoni |
| 2020/0139138 A1 | 5/2020 | Sit et al. |
| 2020/0171309 A1 | 6/2020 | Alataris et al. |

FOREIGN PATENT DOCUMENTS

| | | |
|---|---|---|
| EP | 1070518 | 1/2001 |
| EP | 1181947 A2 | 2/2002 |
| EP | 2243511 A2 | 10/2010 |
| EP | 2448633 A1 | 5/2012 |
| EP | 2630984 A1 | 8/2013 |
| EP | 2586491 | 8/2016 |
| GB | 2449546 A | 11/2008 |
| JP | 2002200179 A | 7/2002 |
| JP | 2007528774 A | 10/2007 |
| JP | 2008500086 | 1/2008 |
| SU | 1512625 A1 | 10/1989 |
| SU | 1690727 A1 | 11/1991 |
| WO | WO-02065896 A2 | 8/2002 |
| WO | WO-02/085448 | 10/2002 |
| WO | WO-02092165 A1 | 11/2002 |
| WO | WO-03015863 A2 | 2/2003 |
| WO | WO-03066154 A2 | 8/2003 |
| WO | WO-2004007018 A1 | 1/2004 |
| WO | WO-2005087314 | 9/2005 |
| WO | WO-2005115532 A2 | 12/2005 |
| WO | WO-2006007048 | 1/2006 |
| WO | WO-2006057734 A1 | 6/2006 |
| WO | WO-2006063458 | 6/2006 |
| WO | WO-2006083884 | 8/2006 |
| WO | WO-2006084635 A2 | 8/2006 |
| WO | WO-2006119046 A1 | 11/2006 |
| WO | WO-2007035925 A2 | 3/2007 |
| WO | WO-2007082382 A1 | 7/2007 |
| WO | WO-2007103324 A1 | 9/2007 |
| WO | WO-2007117232 A1 | 10/2007 |
| WO | WO-2008039982 A2 | 4/2008 |
| WO | WO-2008045434 A2 | 4/2008 |
| WO | WO-2008106174 A1 | 9/2008 |
| WO | WO-2008121891 A1 | 10/2008 |
| WO | WO-2008140940 | 11/2008 |
| WO | WO-2008142402 A1 | 11/2008 |
| WO | WO-2008153726 A2 | 12/2008 |
| WO | WO-2009018518 A1 | 2/2009 |
| WO | WO-2009061813 A1 | 5/2009 |
| WO | WO-2009097224 | 8/2009 |
| WO | WO-20090129329 A1 | 10/2009 |
| WO | WO-2010111358 A2 | 9/2010 |
| WO | WO-2011014570 A1 | 2/2011 |
| WO | WO-2012154985 | 11/2012 |
| WO | WO-2016154091 A1 | 9/2016 |
| WO | WO-2017044904 | 3/2017 |
| WO | WO-2017146658 | 8/2017 |
| WO | WO-2020236946 | 11/2020 |

OTHER PUBLICATIONS

U.S. Appl. No. 61/176,868, filed May 8, 2009, Alataris et al.

U.S. Appl. No. 61/901,255, filed Nov. 7, 2013, Park.

FDA—Premarket Approval, PMA P030017-S002, Boston Scientific Corp., Precision Spinal Cord Stimulation (SCS), Stimulator, Spinal Cord, Totally Implanted for Pain Relief, Model No. SC-1110, https://www.accessdata.fda.gov/scripts/cdrh/cfdocs/cfpma/pma.cfm?id=P030017, Oct. 1, 2004, 3 pages.

New Release, "Boston Scientific Announces Launch of New Precision Plus Spinal Cord Stimulation System—Hardware and software innovations offer new benefits to physicans and patients," PRNewswire—First Call, https://news.bostonscientific.com/news-releases?item=58980, 2 pages.

Shaw et al., "1200Hz Sub-Threshold Epidural Stimulation for Pain Control," Shepherd Center, Interventional Pain Management Physician, Shephard Center, Atlanta, GA., 1 page.

Petition for Inter Partes Review for U.S. Pat. No. 8,892,209—IPR2022-00510, *Boston Scientific Corporation and Boston Scientific Neuromodulation Corporation* (Petitioners) v. *Nevro Corporation* (Patent Owner), Filed Feb. 10, 2022, 102 pages.

Petitioner' Statement on Parallel Petitions for U.S. Pat. No. 8,892,209—IPR2022-00510, *Boston Scientific Corporation and Boston Scientific Neuromodulation Corporation* (Petitioners) v. *Nevro Corporation* (Patent Owner), Filed Feb. 10, 2022, 7 pages.

Petitioner' Updated Exhibit List for U.S. Pat. No. 8,892,209—IPR2022-00510, *Boston Scientific Corporation and Boston Scientific Neuromodulation Corporation* (Petitioners) v. *Nevro Corporation* (Patent Owner), Filed Feb. 14, 2022, 10 pages.

(56) References Cited

OTHER PUBLICATIONS

Patent Owner's Mandatory Notices for U.S. Pat. No. 8,892,209—IPR2022-00510, *Boston Scientific Corporation and Boston Scientific Neuromodulation Corporation* (Petitioners) v. *Nevro Corporation* (Patent Owner), Filed Feb. 25, 2022, 5 pages.
Petition for Inter Partes Review for U.S. Pat. No. 8,892,209—IPR2022-00509, *Boston Scientific Corporation and Boston Scientific Neuromodulation Corporation* (Petitioners) v. *Nevro Corporation* (Patent Owner), Filed Feb. 7, 2022, 95 pages.
Petitioner' Statement on Parallel Petitions for U.S. Pat. No. 8,892,209—IPR2022-00509, *Boston Scientific Corporation and Boston Scientific Neuromodulation Corporation* ; (Petitioners) v. *Nevro Corporation* (Patent Owner), Filed Feb. 7, 2022, 7 pages.
Petitioner' Updated Exhibit List for U.S. Pat. No. 8,892,209—IPR2022-00509, *Boston Scientific Corporation and Boston Scientific Neuromodulation Corporation* (Petitioners) v. *Nevro Corporation* (Patent Owner), Filed Feb. 14, 2022, 10 pages.
Patent Owner's Mandatory Notices for U.S. Pat. No. 8,892,209—IPR2022-00509, *Boston Scientific Corporation and Boston Scientific Neuromodulation Corporation* (Petitioners) v. *Nevro Corporation* (Patent Owner), Filed Feb. 25, 2022, 5 pages.
Exhibit 1007: Declaration of Marom Bikson, Ph.D., Feb. 10, 2022, 191 pages for Petition for Inter Partes Review for U.S. Pat. No. 8,892,209—IPR2022-00510 and Petition for Inter Partes Review for U.S. Pat. No. 8,892,209—IPR2022-00509, *Boston Scientific Corporation and Boston Scientific Neuromodulation Corporation* (Petitioners) v. *Nevro Corporation* (Patent Owner).
Exhibit 1008: Curriculum Vitae of Marom Bikson, Ph.D., 72 pages, for Petition for Inter Partes Review for U.S. Pat. No. 8,892,209—IPR2022-00510 and Petition for Inter Partes Review for U.S. Pat. No. 8,892,209—IPR2022-00509, *Boston Scientific Corporation and Boston Scientific Neuromodulation Corporation* (Petitioners) v. *Nevro Corporation* (Patent Owner).
Exhibit 1022: Declaration of Natalie Bryan, Feb. 7, 2022, 15 pages, for Petition for Inter Partes Review for U.S. Pat. No. 8,892,209—IPR2022-00510 and Petition for Inter Partes Review for U.S. Pat. No. 8,892,209—IPR2022-00509, *Boston Scientific Corporation and Boston Scientific Neuromodulation Corporation* (Petitioners) v. *Nevro Corporation* (Patent Owner).
Exhibit 1024: Declaration of Thomas L. Yearwood, M.D., Ph.D., 13 pages, for Petition for Inter Partes Review for U.S. Pat. No. 8,892,209—IPR2022-00510 and Petition for Inter Partes Review for U.S. Pat. No. 8,892,209—IPR2022-00509, *Boston Scientific Corporation and Boston Scientific Neuromodulation Corporation* (Petitioners) v. *Nevro Corporation* (Patent Owner).
Exhibit 1036: Declaration of Michael Henry Verdolin, M.D. Feb. 7, 2022, 30 pages, for Petition for Inter Partes Review for U.S. Pat. No. 8,892,209—IPR2022-00510 and Petition for Inter Partes Review for U.S. Pat. No. 8,892,209—IPR2022-00509, *Boston Scientific Corporation and Boston Scientific Neuromodulation Corporation* (Petitioners) v. *Nevro Corporation* (Patent Owner).
Exhibit 1037: Curriculum Vitae of Michael Henry Verdolin, M.D, for Petition for Inter Partes Review for U.S. Pat. No. 8,892,209—IPR2022-00510 and Petition for Inter Partes Review for U.S. Pat. No. 8,892,209—IPR2022-00509, *Boston Scientific Corporation and Boston Scientific Neuromodulation Corporation* (Petitioners) v. *Nevro Corporation* (Patent Owner).
Exhibit 1081: Inter Partes Review 2021-01023 for U.S. Pat. No. 9,333,357—Patent Owner's Preliminary Response, *Nalu Medical, Inc.* v. *Nevro Corp.*, Sep. 16, 2021, 85 pages, for Petition for Inter Partes Review for U.S. Pat. No. 8,892,209—IPR2022-00510 and Petition for Inter Partes Review for U.S. Pat. No. 8,892,209—IPR2022-00509, *Boston Scientific Corporation and Boston Scientific Neuromodulation Corporation* (Petitioners) v. *Nevro Corporation* (Patent Owner).
Exhibit 1083: Curriculum Vitae of Thomas L. Yearwood, M.D, for Petition for Inter Partes Review for U.S. Pat. No. 8,892,209—IPR2022-00510 and Petition for Inter Partes Review for U.S. Pat. No. 8,892,209—IPR2022-00509, *Boston Scientific Corporation and Boston Scientific Neuromodulation Corporation* (Petitioners) v. *Nevro Corporation* (Patent Owner).
Exhibit 1092: Patent Owner's Contingent Motion to Amend for Inter Partes Review 2020-01562 for U.S. Pat. No. 9,002,460, *Boston Scientific Corporation and Boston Scientific Neuromodulation Corp* (Petitioners) v. *Nevro Corp* (Patent Owner), Jul. 25, 2021, 34 pages, for Petition for Inter Partes Review for U.S. Pat. No. 8,892,209—IPR2022-00509, *Boston Scientific Corporation and Boston Scientific Neuromodulation Corporation* (Petitioners) v. *Nevro Corporation* (Patent Owner).
Exhibit 1095: Declaration of Wendy Gu, Ph.D., Jan. 31, 2021 for Petition for Inter Partes Review for U.S. Pat. No. 8,892,209—IPR2022-00509, *Boston Scientific Corporation and Boston Scientific Neuromodulation Corporation* (Petitioners) v. *Nevro Corporation* (Patent Owner).
Advanced Bionics—Precision, Physician Implant Manual, Implantable Pulse Generator model SC1100, https://www.fcc.gov/oet/ea/fccid, 2003, 45 pages.
Aronow et al., "Spinal Cord Stimulation for Treatment of Angina Pectoris," Coronary Artery Disease, 2004, 5 pages.
Barolat et al., "Mapping of sensory responses to epidural stimulation of intraspinal neural structures in man," Jourcal of Neurosurgery, vol. 78, Feb. 1993, 7 pages.
Congress of Neurological Surgeons—Preliminary Program, Annual Meeting Chicago, Illinois Oct. 7-12, 2006, 84 pages.
De Jongste et al., "Efficacy of Spinal Cord Stimulation as Adjuvant Therapy for Intractable Angina Pectoris: A Prospective, Randomized Clinical Study," JACC, vol. 7, Jun. 1994, 6 pages.
Falowski et al., "Spinal Cord Stimulation: An Update," Neurotherapeutics: The Journal of the American Society for Experimental NeuroTherapeautics, vol. 5, Jan. 2008, 14 pages.
FDA—Premarket Approval, PMA P030017-S008, Approval for Artisan 2×8 Paddle Lead, Model SC-8116-XX for the Precision SCS System, https://www.accessdata.fda.gov/scripts/cdrh/cfdocs/cfpma/pma.cfm?id=P030017S008, Aug. 18, 2005, 3 pages.
FDA, Premarket Approval—PMA P840001-S037, Itrel 3 Spinal Cord Stimulation (SCS) for Treatment of Chronic Intractable Pain of hte Trunk and or Limbs, https://www.accessdata.fda.gov/scripts/cdrh/cfdocs/cfpma/pma.cfm?id=P840001S037, Aug. 29, 1995, 3 pages.
Mannheimer et al., "Electrical Stimulation Versus Coronary Artery Bypass Surgery in Severe Angina Pectoris—The ESBY Study," American Heart Association, Inc., 1998, 7 pages.
Manuscript of Eddicks et al., "Thoracic Spinal Cord Stimulation Improves Functional Status and Relieves Symptoms in Patients with Refactory Angina Pectoris: The First Placebo-Controlled Randomized Study," Heart Online First, Jan. 19, 2007, 19 pages.
Medtronic—ITREL 3 Neurostimulator 7425 Neurostimulator, Implant Manual, https://www.neuromodulation.ch/sites/default/files/pictures/itrel3_implant_manual.pdf, 1995, 20 pages.
Medtronic—Itrel EZ Model 7437A Patient Programmer, User Manual, https://fcc.gov/oet/ea/fccid, 2001, 154 pages.
Medtronic—Neuromodulation Product Performance, https://www.medtronic.com/content/dam/medtronic-com/products/product-performance/ppr-reports/product-performance-report-2009.pdf, 2009, 61 pages.
Medtronic—Product Performance Report, https://www.medtronic.com/content/dam/medtronic-com/products/product-performance/ppr-reports/product-performance-report-2010.pdf, 2010, 86 pages.
Medtronic—Spinal Cord Stimulation, Patient Management Guidelines for Clinicians, https://web.archive/org/web/20060522070227/http://medtronic.com/neuro/paintherapies/pain_treatment_ladder/library.html, 1999, 19 pages.
Medtronic—Synergy EZ Model 7435 Patient Programmer, User Manual, https://www.fcc.gov/oet/ea/fccid, 1998, 110 pages.
Medtronic—Synergy, Synergy Versitrel 7427 7427V, Dual-Program Neurostimulators for Spinal Cord Stimulation (SCS), http://www.neuromodulation.ch/sites/default/files/pictures/synergy_implant_manual.pdf, 2003, 96 pages.
Medtronic Activa Parkinson's Control Therapy, Summary of Safety and Effectiveness Data for a Supplemental Premarket Approval Application, PMA P960009/S7, https://www.accessdata.fda.gov/cdrh_docs/pdf/p960009S007b.pdf, Aug. 29, 1995, 30 pages.

(56) References Cited

OTHER PUBLICATIONS

Merrill et al., "Electrical Stimulation of Excitable Tissue: Design of Efficacious and Safe Protocols," Journal of Neuroscience Methods, 2005, 28 pages.
Summary of Safety and Effectiveness, PMA P030017, Precision Spinal Cord Stimulator (SCS) System, https://www.accessdata.fda.gov/cdrh_docs/pdf3/P030017B.pdf, 2004, 18 pages.
Wolter et al., "Effects of Sub-perception threshold spinal cord stimulation in neuropathic pain: A randomized controlled double-blind crossover study," European Journal of Pain, 2012, 8 pages.
Petition for Inter Partes Review for U.S. Pat. No. 10,576,286—IPR2022-00512, *Boston Scientific Corporation and Boston Scientific Neuromodulation Corporation* (Petitioners) v. *Nevro Corporation* (Patent Owner), Filed Feb. 15, 2022, 95 pages.
Notice of Filing Date Accorded to Petition and Time for Filing Patent Owner Preliminary Response for U.S. Pat. No. 10,576,286—IPR2022-00512, *Boston Scientific Corporation and Boston Scientific Neuromodulation Corporation* (Petitioners) v. *Nevro Corporation* (Patent Owner), Feb. 24, 2022, 5 pages.
Patent Owner's Mandatory Notices for U.S. Pat. No. 10,576,286—IPR2022-00512, *Boston Scientific Corporation and Boston Scientific Neuromodulation Corporation* (Petitioners) v. *Nevro Corporation* (Patent Owner), Filed Mar. 2, 2022, 5 pages.
Petition for Inter Partes Review for U.S. Pat. No. 10,556,112—IPR2022-00511, *Boston Scientific Corporation and Boston Scientific Neuromodulation Corporation* (Petitioners) v. *Nevro Corporation* (Patent Owner), Filed Feb. 15, 2022, 95 pages.
Notice of Filing Date Accorded to Petition and Time for Filing Patent Owner Preliminary Response for U.S. Pat. No. 10,556,112—IPR2022-00511, *Boston Scientific Corporation and Boston Scientific Neuromodulation Corporation* (Petitioners) v. *Nevro Corporation* (Patent Owner), Feb. 24, 2022, 5 pages.
Patent Owner's Mandatory Notices for U.S. Pat. No. 10,556,112—IPR2022-00511, *Boston Scientific Corporation and Boston Scientific Neuromodulation Corporation* (Petitioners) v. *Nevro Corporation* (Patent Owner), Filed Mar. 2, 2022, 5 pages.
Exhibit 1003: Declaration of Marom Bikson, Ph.D., Feb. 15, 2022, 128 pages, for Petition for Inter Partes Review for U.S. Pat. No. 10,576,286—IPR2022-00512 and Petition for Inter Partes Review for U.S. Pat. No. 10,556,112—IPR2022-00511, *Boston Scientific Corporation and Boston Scientific Neuromodulation Corporation* (Petitioners) v. *Nevro Corporation* (Patent Owner).
Exhibit 1004: Curriculum Vitae of Marom Bikson, Ph.D., 72 pages, for Petition for Inter Partes Review for U.S. Pat. No. 10,576,286—IPR2022-00512 and Petition for Inter Partes Review for U.S. Pat. No. 10,556,112—IPR2022-00511, *Boston Scientific Corporation and Boston Scientific Neuromodulation Corporation* (Petitioners) v. *Nevro Corporation* (Patent Owner).
Exhibit 1014: Declaration of Natalie Bryan, Feb. 7, 2022, 15 pages. for Petition for Inter Partes Review for U.S. Pat. No. 10,576,286—IPR2022-00512 and Petition for Inter Partes Review for U.S. Pat. No. 10,556,112—IPR2022-00511, *Boston Scientific Corporation and Boston Scientific Neuromodulation Corporation* (Petitioners) v. *Nevro Corporation* (Patent Owner).
Exhibit 1015: Declaration of Dr. Erik Shaw, Feb. 14, 2022, for Petition for Inter Partes Review for U.S. Pat. No. 10,576,286—IPR2022-00512 and Petition for Inter Partes Review for U.S. Pat. No. 10,556,112—IPR2022-00511, *Boston Scientific Corporation and Boston Scientific Neuromodulation Corporation* (Petitioners) v. *Nevro Corporation* (Patent Owner).
Exhibit 1019: Declaration of Michael Henry Verdolin, Feb. 15, 2022, for Petition for Inter Partes Review for U.S. Pat. No. 10,576,286—IPR2022-00512 and Petition for Inter Partes Review for U.S. Pat. No. 10,556,112—IPR2022-00511, *Boston Scientific Corporation and Boston Scientific Neuromodulation Corporation* (Petitioners) v. *Nevro Corporation* (Patent Owner).
Exhibit 1022: Declaration of Thomas L. Yearwood, M.D., Ph.D., 13 pages, for Petition for Inter Partes Review for U.S. Pat. No. 10,576,286—IPR2022-00512 and Petition for Inter Partes Review for U.S. Pat. No. 10,556,112—IPR2022-00511, *Boston Scientific Corporation and Boston Scientific Neuromodulation Corporation* (Petitioners) v. *Nevro Corporation* (Patent Owner).
Exhibit 1034: Curriculum Vitae of Dr. Erik Shaw, 4 pages, for Petition for Inter Partes Review for U.S. Pat. No. 10,576,286—IPR2022-00512 and Petition for Inter Partes Review for U.S. Pat. No. 10,556,112—IPR2022-00511, *Boston Scientific Corporation and Boston Scientific Neuromodulation Corporation* (Petitioners) v. *Nevro Corporation* (Patent Owner).
Exhibit 1035: Declaration of Dr. Richard Boydston North, Feb. 12, 2022, 10 pages, for Petition for Inter Partes Review for U.S. Pat. No. 10,576,286—IPR2022-00512 and Petition for Inter Partes Review for U.S. Pat. No. 10,556,112—IPR2022-00511, *Boston Scientific Corporation and Boston Scientific Neuromodulation Corporation* (Petitioners) v. *Nevro Corporation* (Patent Owner).
Exhibit 1036: Curriculum Vitae of Dr. Richard Boydston North, 53 pages, for Petition for Inter Partes Review for U.S. Pat. No. 10,576,286—IPR2022-00512 and Petition for Inter Partes Review for U.S. Pat. No. 10,556,112—IPR2022-00511, *Boston Scientific Corporation and Boston Scientific Neuromodulation Corporation* (Petitioners) v. *Nevro Corporation* (Patent Owner).
Exhibit 1051: Response to Certificate of Corrections for U.S. Pat. No. 9,002,549, Jan. 25, 2022, 2 pages, for Petition for Inter Partes Review for U.S. Pat. No. 10,576,286—IPR2022-00512 and Petition for Inter Partes Review for U.S. Pat. No. 10,556,112—IPR2022-00511, *Boston Scientific Corporation and Boston Scientific Neuromodulation Corporation* (Petitioners) v. *Nevro Corporation* (Patent Owner).
Exhibit 1052: Applicant's Reply to Response to the Request for Certificate of Corrections for U.S. Pat. No. 9,002,459, Jul. 28, 2021, 2 pages, for Petition for Inter Partes Review for U.S. Pat. No. 10,576,286—IPR2022-00512 and Petition for Inter Partes Review for U.S. Pat. No. 10,556,112—IPR2022-00511, *Boston Scientific Corporation and Boston Scientific Neuromodulation Corporation* (Petitioners) v. *Nevro Corporation* (Patent Owner).
Patent Owner's Preliminary Response for U.S. Pat. No. 8,892,209 for Inter Partes Review IPR2022-00509, *Boston Scientific Corporation and Boston Scientific Neuromodulation Corporation* (Petitioners) v. *Nevro Corporation* (Patent Owner), Filed May 16, 2022, 86 pages.
Patent Owner's Exhibit List for U.S. Pat. No. 8,892,209 for Inter Partes Review IPR2022-00509, *Boston Scientific Corporation and Boston Scientific Neuromodulation Corporation* (Petitioners) v. *Nevro Corporation* (Patent Owner), Filed May 16, 2022, 10 pages.
Patent Owner's Response to Petitioner's Statement on Parallel Petitions for U.S. Pat. No. 8,892,209 for Inter Partes Review IPR2022-00509, *Boston Scientific Corporation and Boston Scientific Neuromodulation Corporation* (Petitioners) v. *Nevro Corporation* (Patent Owner), Filed May 16, 2022, 8 pages.
Petitioner's Reply to Patent Owner's Preliminary Response for U.S. Pat. No. 8,892,209 for Inter Partes Review IPR2022-00509, *Boston Scientific Corporation and Boston Scientific Neuromodulation Corporation* (Petitioners) v. *Nevro Corporation* (Patent Owner), Filed Jun. 24, 2022, 12 pages.
Petitioner's Updated Exhibit List for U.S. Pat. No. 8,892,209 for Inter Partes Review IPR2022-00509, *Boston Scientific Corporation and Boston Scientific Neuromodulation Corporation* (Petitioners) v. *Nevro Corporation* (Patent Owner), Filed Jun. 24, 2022, 11 pages.
Patent Owner's Sur-Reply for U.S. Pat. No. 8,892,209 for Inter Partes Review IPR2022-00509, *Boston Scientific Corporation and Boston Scientific Neuromodulation Corporation* (Petitioners) v. *Nevro Corporation* (Patent Owner), Filed Jul. 5, 2022, 13 pages.
Joint Motion to Terminate Pursuant to 35 U.S.C. § 317 for U.S. Pat. No. 8,892,209 for Inter Partes Review IPR2022-00509, *Boston Scientific Corporation and Boston Scientific Neuromodulation Corporation* (Petitioners) v. *Nevro Corporation* (Patent Owner), Filed Aug. 5, 2022, 6 pages.
Joint Request that the Settlement Agreement be Treated as Business Confidential Information pursuant to 35 U.S.C. § 317 for U.S. Pat. No. 8,892,209 for Inter Partes Review IPR2022-00509, *Boston Scientific Corporation and Boston Scientific Neuromodulation Corporation* (Petitioners) v. *Nevro Corporation* (Patent Owner), Filed Aug. 5, 2022, 4 pages.

(56) References Cited

OTHER PUBLICATIONS

Patent Owner's Preliminary Response for U.S. Pat. No. 8,892,209—IPR2022-00510, *Boston Scientific Corporation and Boston Scientific Neuromodulation Corporation* (Petitioners) v. *Nevro Corporation* (Patent Owner), Filed May 16, 2022, 80 pages.

Patent Owner's Exhibit List for U.S. Pat. No. 8,892,209—IPR2022-00510, *Boston Scientific Corporation and Boston Scientific Neuromodulation Corporation* (Petitioners) v. *Nevro Corporation* (Patent Owner), Filed May 16, 2023, 10 pages.

Petitioners' Reply to Patent Owner's Preliminary Response for U.S. Pat. No. 8,892,209—IPR2022-00510, *Boston Scientific Corporation and Boston Scientific Neuromodulation Corporation* (Petitioners) v. *Nevro Corporation* (Patent Owner), Filed Jun. 24, 2022, 12 pages.

Petitioners' Updated Exhibit List for U.S. Pat. No. 8,892,209—IPR2022-00510, *Boston Scientific Corporation and Boston Scientific Neuromodulation Corporation* (Petitioners) v. *Nevro Corporation* (Patent Owner), Filed Jun. 24, 2022, 11 pages.

Patent Owners' Sur-Reply for U.S. Pat. No. 8,892,209—IPR2022-00510, *Boston Scientific Corporation and Boston Scientific Neuromodulation Corporation* (Petitioners) v. *Nevro Corporation* (Patent Owner), Filed Jul. 5, 2022, 13 pages.

Joint Request that the Settlement Agreement Be Treated as Business Confidential Information Pursuant to 35 U.S.C.§ 317 for U.S. Pat. No. 8,892,209—IPR2022-00510, *Boston Scientific Corporation and Boston Scientific Neuromodulation Corporation* (Petitioners) v. *Nevro Corporation* (Patent Owner), Filed Aug. 5, 2022, 4 pages.

Decision—Settlement Prior to Institution of Trial 37 C.F.R. § 42.74 for U.S. Pat. No. 8,892,209—IPR2022-00510; U.S. Pat. No. 8,892,209 for Inter Partes Review IPR2022-00509; U.S. Pat. No. 10,576,286—Inter Partes Review for IPR2022-00512; U.S. Pat. No. 10,556,112—Inter Partes Review for IPR2022-00511—*Boston Scientific Corporation and Boston Scientific Neuromodulation Corporation* (Petitioners) v. *Nevro Corporation* (Patent Owner), Filed Aug. 8, 2022, 4 page.

Exhibit 2002: C.V. of Peter Crosby for U.S. Pat. No. 8,892,209—IPR2022-00510 and Petition for Inter Partes Review for U.S. Pat. No. 8,892,209—IPR2022-00509, *Boston Scientific Corporation and Boston Scientific Neuromodulation Corporation* (Petitioners) v. *Nevro Corporation* (Patent Owner).

Exhibit 2003: Declaration of Peter Crosby for U.S. Pat. No. 8,892,209—IPR2022-00510 and Petition for Inter Partes Review for U.S. Pat. No. 8,892,209—IPR2022-00509, *Boston Scientific Corporation and Boston Scientific Neuromodulation Corporation* (Petitioners) v. *Nevro Corporation* (Patent Owner).

Exhibit 2007: C.V. of Michael Fishman, M.D. for U.S. Pat. No. 8,892,209—IPR2022-00510 and Petition for Inter Partes Review for U.S. Pat. No. 8,892,209—IPR2022-00509, *Boston Scientific Corporation and Boston Scientific Neuromodulation Corporation* (Petitioners) v. *Nevro Corporation* (Patent Owner).

Exhibit 2008: Declaration of Michael Fishman, M.D. for U.S. Pat. No. 8,892,209—IPR2022-00510 and Petition for Inter Partes Review for U.S. Pat. No. 8,892,209—IPR2022-00509, *Boston Scientific Corporation and Boston Scientific Neuromodulation Corporation* (Petitioners) v. *Nevro Corporation* (Patent Owner).

Exhibit 2015: *Nevro Corp.* v. *Boston Scientific Corp.*, 955 F.3d 35 (Fed. Cir. 2020) for U.S. Pat. No. 8,892,209—IPR2022-00510; U.S. Pat. No. 8,892,209 for Inter Partes Review IPR2022-00509; U.S. Pat. No. 10,576,286—Inter Partes Review for IPR2022-00512; U.S. Pat. No. 10,556,112—Inter Partes Review for IPR2022-00511—*Boston Scientific Corporation and Boston Scientific Neuromodulation Corporation* (Petitioners) v. *Nevro Corporation* (Patent Owner).

Exhibit 2016: *Nevro Corp.* v. *Boston Scientific Corp.*, No. 16-cv-06830-VC, 2018 WL 4676501 (N.D. Cal. Jul. 24, 2018) for U.S. Pat. No. 8,892,209—IPR2022-00510 and Petition for Inter Partes Review for U.S. Pat. No. 8,892,209—IPR2022-00509, *Boston Scientific Corporation and Boston Scientific Neuromodulation Corporation* (Petitioners) v. *Nevro Corporation* (Patent Owner).

Exhibit 2022: *Nevro Corp.* v. *Boston Scientific Corp.*, No. 3:16-cv-6830, Dkt. 1, Complaint for Patent Infringement and Declaratory Judgment, Demand for Jury Trial (N.D. Cal. Nov. 28, 2016) for U.S. Pat. No. 8,892,209—IPR2022-00510; U.S. Pat. No. 8,892,209 for Inter Partes Review IPR2022-00509; U.S. Pat. No. 10,576,286—Inter Partes Review for IPR2022-00512; U.S. Pat. No. 10,556,112—Inter Partes Review for IPR2022-00511—*Boston Scientific Corporation and Boston Scientific Neuromodulation Corporation* (Petitioners) v. *Nevro Corporation* (Patent Owner).

Exhibit 2023: *Nevro Corp.* v. *Boston Scientific Corp.*, No. 3:16-cv-06830-VC, Dkt. 554, Stipulation and [Proposed] Order of Dismissal (N.D. Cal. Dec. 14, 2020) for U.S. Pat. No. 8,892,209—IPR2022-00510; U.S. Pat. No. 8,892,209 for Inter Partes Review IPR2022-00509; U.S. Pat. No. 10,576,286—Inter Partes Review for IPR2022-00512; U.S. Pat. No. 10,556,112—Inter Partes Review for IPR2022-00511—*Boston Scientific Corporation and Boston Scientific Neuromodulation Corporation* (Petitioners) v. *Nevro Corporation* (Patent Owner).

Exhibit 2025: *Nevro Corp.* v. *Boston Scientific Corp.*, No. 1:21-cv-00258-UNA, Dkt. 1, Complaint (D.Del. Feb. 23, 2021) for U.S. Pat. No. 8,892,209—IPR2022-00510; U.S. Pat. No. 8,892,209 for Inter Partes Review IPR2022-00509; U.S. Pat. No. 10,576,286—Inter Partes Review for IPR2022-00512; U.S. Pat. No. 10,556,112—Inter Partes Review for IPR2022-00511—*Boston Scientific Corporation and Boston Scientific Neuromodulation Corporation* (Petitioners) v. *Nevro Corporation* (Patent Owner).

Exhibit 2026: *Nevro Corp.* v. *Stimwave Technologies, Inc.*, No. 1:19-cv-00325-UNA, Dkt. 1, Complaint for Patent Infringement, Declaratory Judgment of Patent Infringement, Violation of the Lanham Act, and Deceptive Trade Practices (D. Del Feb. 14, 2019) for U.S. Pat. No. 8,892,209—IPR2022-00510 and Petition for Inter Partes Review for U.S. Pat. No. 8,892,209—IPR2022-00509, *Boston Scientific Corporation and Boston Scientific Neuromodulation Corporation* (Petitioners) v. *Nevro Corporation* (Patent Owner).

Exhibit 2027:*Nevro Corp.* v. *Stimwave Technologies, Inc.*, No. 1:19-cv-00325-CFC, Dkt. 98, Stimwave's Answering Brief in Opposition to Plaintiff Nevro's Motion for a Preliminary Injunction (D.Del. Jun. 6, 2019) for U.S. Pat. No. 8,892,209—IPR2022-00510 and Petition for Inter Partes Review for U.S. Pat. No. 8,892,209—IPR2022-00509, *Boston Scientific Corporation and Boston Scientific Neuromodulation Corporation* (Petitioners) v. *Nevro Corporation* (Patent Owner).

Exhibit 2028: *Nevro Corp.* v. *Stimwave Technologies, Inc.*, No. 1:19-cv-00325-CFC, Dkt. 231, Stipulated Consent Judgment and Permanent Injunction (D.Del. Mar. 2, 2020) for U.S. Pat. No. 8,892,209—IPR2022-00510 and Petition for Inter Partes Review for U.S. Pat. No. 8,892,209—IPR2022-00509, *Boston Scientific Corporation and Boston Scientific Neuromodulation Corporation* (Petitioners) v. *Nevro Corporation* (Patent Owner).

Exhibit 2032: Ex parte Knudson, Appeal No. 2021-001841, Decision on Appeal (PTAB Oct. 26, 2021) for U.S. Pat. No. 8,892,209—IPR2022-00510 and Petition for Inter Partes Review for U.S. Pat. No. 8,892,209—IPR2022-00509, *Boston Scientific Corporation and Boston Scientific Neuromodulation Corporation* (Petitioners) v. *Nevro Corporation* (Patent Owner).

Exhibit 2033: *Nevro Corp.* v. *Nalu Medical, Inc.*, No. 20-291 (CFC)(JLH), Nevro Corp.'s Response to Defendant Nalu Medical, Inc.'s First Set of Interrogatories (Nos. 1-10) (D.Del. May 7, 2021) for U.S. Pat. No. 8,892,209—IPR2022-00510 and Petition for Inter Partes Review for U.S. Pat. No. 8,892,209—IPR2022-00509, *Boston Scientific Corporation and Boston Scientific Neuromodulation Corporation* (Petitioners) v. *Nevro Corporation* (Patent Owner).

Exhibit 2035: *Boston Scientific Neuromodulation Corporation* v. *Nevro Corporation*, IPR2015-01203, Paper 10, Decision Denying Institution of Inter Partes Review (PTAB Nov. 30, 2015) for U.S. Pat. No. 8,892,209—IPR2022-00510; U.S. Pat. No. 8,892,209 for Inter Partes Review IPR2022-00509; U.S. Pat. No. 10,576,286; Inter Partes Review for IPR2022-00512; U.S. Pat. No. 10,556,112—Inter Partes Review for IPR2022-00511—*Boston Scientific Corporation and Boston Scientific Neuromodulation Corporation* (Petitioners) v. *Nevro Corporation* (Patent Owner).

Exhibit 2038: *Nevro Corp.* v. *Nalu Medical, Inc.*, No. 1:20-cv-00291-CFC, Dkt. 14, First Amended Complaint for Patent Infringement (D. Del Jun. 1, 2020) for U.S. Pat. No. 8,892,209—IPR2022-00510 and Petition for Inter Partes Review for U.S. Pat. No.

(56) References Cited

OTHER PUBLICATIONS 8,892,209—IPR2022-00509, *Boston Scientific Corporation and Boston Scientific Neuromodulation Corporation* (Petitioners) v. *Nevro Corporation* (Patent Owner).
Exhibit 2045: *Nevro Corp.* v. *Stimwave Technologies, Inc.*, No. 19-325-CFC, 2019 WL 3322368 (D.Del. Jul. 24, 2019) for U.S. Pat. No. 8,892,209—IPR2022-00510 and Petition for Inter Partes Review for U.S. Pat. No. 8,892,209—IPR2022-00509, *Boston Scientific Corporation and Boston Scientific Neuromodulation Corporation* (Petitioners) v. *Nevro Corporation* (Patent Owner).
Exhibit 2046: *Nevro Corp.* v. *Nalu Medical, Inc.*, No. 1:20-cv-00291-UNA, Dkt. 1, Complaint for Patent Infringement (D.Del. Feb. 28, 2020) for U.S. Pat. No. 8,892,209—IPR2022-00510 and Petition for Inter Partes Review for U.S. Pat. No. 8,892,209—IPR2022-00509, *Boston Scientific Corporation and Boston Scientific Neuromodulation Corporation* (Petitioners) v. *Nevro Corporation* (Patent Owner).
Exhibit 2052: U.S. Patent and Trademark Office, Declaration of James Thacker, U.S. Appl. No. 13/705,021 (Dec. 4, 2012) (No. 3:16-cv-06830-VC, Dkt. 398-13, Exhibit 12 (May 24, 2018) for U.S. Pat. No. 8,892,209—IPR2022-00510 and Petition for Inter Partes Review for U.S. Pat. No. 8,892,209—IPR2022-00509, *Boston Scientific Corporation and Boston Scientific Neuromodulation Corporation* (Petitioners) v. *Nevro Corporation* (Patent Owner).
Exhibit 2055: *Nevro Corp.* v. *Boston Scientific Corp.*, No. 18-2220, Dkt. 32, Principal and Response Brief for Defendants-Cross-Appellants Boston Scientific Corporation and Boston Scientific Neuromodulation Corporation (Fed. Cir. Jan. 17, 2019) for U.S. Pat. No. 8,892,209—IPR2022-00510 and Petition for Inter Partes Review for U.S. Pat. No. 8,892,209—IPR2022-00509, *Boston Scientific Corporation and Boston Scientific Neuromodulation Corporation* (Petitioners) v. *Nevro Corporation* (Patent Owner).
Exhibit 2060: Inter Partes Review 2021-01203 for U.S. Pat. No. 8,359,102—Patent Owner's Preliminary Response, *Boston Scientific Neuromodulation Corporation.* v. *Nevro Corp.*, Sep. 1, 2015, 70 pages, for Petition for Inter Partes Review for U.S. Pat. No. 8,892,209—IPR2022-00510, *Boston Scientific Corporation and Boston Scientific Neuromodulation Corporation* (Petitioners) v. *Nevro Corporation* (Patent Owner).
Patent Owner's Preliminary Response for U.S. Pat. No. 10,576,286—Inter Partes Review for IPR2022-00512, *Boston Scientific Corporation and Boston Scientific Neuromodulation Corporation* (Petitioners) v. *Nevro Corporation* (Patent Owner), Filed May 24, 2022, 38 pages.
Joint Motion to Terminate Pursuant to 35 U.S.C. 317 for U.S. Pat. No. 10,576,286—Inter Partes Review for IPR2022-00512, *Boston Scientific Corporation and Boston Scientific Neuromodulation Corporation* (Petitioners) v. *Nevro Corporation* (Patent Owner), Filed Aug. 5, 2022, 6 pages.
Joint Request that the Settlement Agreement be Treated as Business Confidential Information Pursuant to 35 U.S.C. 317 for U.S. Pat. No. 10,576,286—Inter Partes Review for IPR2022-00512, *Boston Scientific Corporation and Boston Scientific Neuromodulation Corporation* (Petitioners) v. *Nevro Corporation* (Patent Owner), Filed Aug. 5, 2022, 4 pages.
Patent Owner's Preliminary Response for U.S. Pat. No. 10,556,112—Inter Partes Review IPR2022-00511, *Boston Scientific Corporation and Boston Scientific Neuromodulation Corporation* (Petitioners) v. *Nevro Corporation* (Patent Owner), Filed May 24, 2022, 37 pages.
Joint Motion to Terminate Pursuant to 35 U.S.C. § 317 for U.S. Pat. No. 10,556,112—Inter Partes Review IPR2022-00511, *Boston Scientific Corporation and Boston Scientific Neuromodulation Corporation* (Petitioners) v. *Nevro Corporation* (Patent Owner), Filed May 24, 2022, 37 pages.
Joint Request that the Settlement Agreement be Treated as Business Confidential Information Pursuant to 35 U.S.C. § 317 for U.S. Pat. No. 10,556,112—Inter Partes Review IPR2022-00511, *Boston Scientific Corporation and Boston Scientific Neuromodulation Corporation* (Petitioners) v. *Nevro Corporation* (Patent Owner), Filed May 24, 2022, 37 pages.

Exhibit 2002: *Boston Scientific Corp.* v. *Nevro Corp.*, No. 18-644 (CFC), Dkt. 27, Answer, Affirmative Defenses, and Counterclaims to First Amended Complaint (D. Del. Dec. 9, 2019) Inter Partes Review for IPR2022-00512; U.S. Pat. No. 10,556,112—Inter Partes Review for IPR2022-00511—*Boston Scientific Corporation and Boston Scientific Neuromodulation Corporation* (Petitioners) v. *Nevro Corporation* (Patent Owner).
Exhibit 2003: *Boston Scientific Corp.* v. *Nevro Corp.*, No. 16-1163 (CFC)(Consolidated), Dkt. 551, Claim Construction Order (D. Del. Feb. 25, 2021) Inter Partes Review for IPR2022-00512; U.S. Pat. No. 10,556,112—Inter Partes Review for IPR2022-00511—*Boston Scientific Corporation and Boston Scientific Neuromodulation Corporation* (Petitioners) v. *Nevro Corporation* (Patent Owner).
Exhibit 2036: *Boston Scientific Neuromodulation Corporation* v. *Nevro Corp.*, IPR2015-01204, Paper 10, Decision Denying Institution of Inter Partes Review (PTAB Nov. 30, 2015) Inter Partes Review for IPR2022-00512; U.S. Pat. No. 10,556,112—Inter Partes Review for IPR2022-00511—*Boston Scientific Corporation and Boston Scientific Neuromodulation Corporation* (Petitioners) v. *Nevro Corporation* (Patent Owner).
Lee et al., "Predicted Effects of Pulse Width Programming in Spinal Cord Stimulation: A Mathematical Modeling Study," Medical & Biological Engineering & Computing, 2011, 10 pages.
FDA Summary of Safety and Effectiveness Data, PMA P130022, Senza Spinal Cord Stimulation (SCS) System, 56 pages.
Nevro Senza Spinal Cord Stimulator (SCS) System—Patient Manual, 2021, 94 pages.
Boston Scientific, "Precision™ Spinal Cord Stimulator System Clinician Manual," 9108273-04, 2017, 74 pages.
St. Jude Medical, "Eon Mini™ Rechargeable IPG" 2015, 5 pages.
Nevro, News Release: "Neurosurgery Selects the SENZA-RCT 24-Month Outcomes Publication as the Top Pain Paper of the Year" Jun. 15, 2017, 2 pages.
Morgan Stanely Research, "Nevro Corp, Fundamentals are Very Much Intact," Nov. 8, 2016, 12 pages.
Morgan Stanley—Research, "Medical Technology: Disrupting Neuromodulation Abbott & Nevro are the Winners," Feb. 22, 2017, 27 pages.
Mills et al., Nevro, "Initation of Coverage: Compelling growth engine with plenty of fuel in the tank; initiate at BUY, $120 target," Canaccord Genuity, Mar. 23, 2017, 57 pages.
"WaveWriter Alpha Spinal Cord Stimulator System wins Best Overall Medical Device Solution Award," 222 Shares, May 24, 2021, 2 pages.
Boston Scientific, "Boston Scientific Launches WaveWriter Alpha™ Spinal Cord Stimulator Systems in U.S.," Jan. 14, 2021, 3 pages.
Foletti et al., "Neurostimulation technology for the treatment of chronic pain: a focus on spinal cord stimulation," Future Drugs Ltd, 2007, 14 pages.
"EQ-5D-3L, About," available at https://euroqol.org/eq-5dinstruments/eq-5d-3l-about/ Mar. 31, 2022, 3 pages.
Kloth, Luther C., "Electrical Stimulation Technologies for Wound Healing," Wound Healthing Society, 2014, 11 pages.
Kathuroju et al., "Effect of Low Frequency Pulsed DC on Human Skin in Vivo: Resistance Studies in Reverse Iontophoresis," 104 Sensors & Transducers Journal 47-57 , 2009, 17 pages.
Bendel, Markus, "New Developments in Spinal Stimulation for Pain Management," Mayo Clinic,https://connect.mayoclinic.org/blog/adult-pain-medicine/newsfeed-post/new-developments-in-spinal-stimulation/ , Nov. 2018, 13 pages.
J.P. Morgan, "Nevro—Quarterly Results In-line with Preannouncement; Hiring in Focus for 2H18," North America Equity Research, Aug. 2, 2018, 8 pages.
Mironer et al., "Pain Tolernace Threshold: A Pilot Study of an Objective Measurement of Spinal Cord Stimulator Trial Results," Pain Medicine, vol. 1, No. 2, 2000, 6 pages.
Smits et al., "Spinal cord stimulation induces c-Fos expression in the dorsal horn in rats with neuropathic pain after partial sciatic nerve injury," Neuroscience Letters 450, 2009, 4 pages.
Struijk et al., "Paresthesia Thresholds in Spinal Cord Stimulation: A Comparison of Theoretical Results with Clinical Data," IEEE Transactions on Rehabilitation Engineering, vol. 1, No. 2, Jun. 1993, 8 pages.

(56) References Cited

OTHER PUBLICATIONS

Abejon et al., "Effects of Movement and Postural Positions in Spinal Cord Stimulation in the New Rechargeable Systems," Pain Physician, 2014, 8 pages.
Holsheimer et al., "Spinal Geometry and Paresthesia Coverage in Spinal Cord Stimulation," International Neuromodulation Society, 1998, 8 pages.
Kumar et al., "The use of spinal cord stimulation in pain management," Pain Management, 2012, 11 pages.
Kumar, Krishna, "Neuromodulation and Immortality," Neuromodulation, 2014, 3 pages.
Taylor et al., "Spinal cord stimulation in the treatment of refractory angina: systematic review and meta-analysis of randomised controlled trials," BioMed Central—BMC Cardiovascular Disorders, 2009, 13 pages.
Diedrichs et al., "Symptomatic Relief Precedes Improvement of Myocardial Blood Flow in Patients Under Spinal Cord Stimulation," Current Controlled Trials in Cardiovascular Medicine, 2005, 7 pages.
Wu et al., "Putative Mechanisms Behind Effects of Spinal Cord Stimulation on Vascular Diseases: A Review of Experimental Studies," Autonomic Neuroscience, 2008, 15 pages.
Webster's New World Medical Dictionary, pp. 317-318, Wiley Publishing, Inc., 3d edition, 2008, 5 pages.
Petition for Inter Partes Review of U.S. Pat. No. 9,333,357, Case No. IPR2021-01023, Petitioner: *Nalu Medical, Inc.*; Patent Owner: *Nevro Corporation*, May 27, 2021, 117 oages.
Exhibit 1002—"File History of U.S. Pat. No. 9,333,357," Petition for Inter Partes Review of U.S. Pat. No. 9,333,357, Case No. IPR2021-01023, Petitioner: *Nalu Medical, Inc.*; Patent Owner: *Nevro Corporation*, May 27, 2021, 454 pages.
Exhibit 1003—Declaration of Dr. Gerald E. Loeb, M.D. in Support of Petition for Inter Partes Review of U.S. Pat. No. 9,333,357, Case No. IPR2021-01023, Petitioner: *Nalu Medical, Inc.*; Patent Owner: *Nevro Corporation*, May 27, 2021, 166 pages.
Exhibit 1004—"Curriculum Vitae of Gerald E. Loeb, M.D.," in Support of Petition for Inter Partes Review of U.S. Pat. No. 9,333,357, Case No. IPR2021-01023, Petitioner: *Nalu Medical, Inc.*; Patent Owner: *Nevro Corporation*, May 27, 2021, 39 pages.
Exhibit 1007—Declaration of Thomas L. Yearwood M.D., Ph.D. in Support of Petition for Inter Partes Review of U.S. Pat. No. 9,333,357, Case No. IPR2021-01023, Petitioner: *Nalu Medical, Inc.*; Patent Owner: *Nevro Corporation*, May 27, 2021, 10 pages.
Exhibit 1008—"Curriculum Vitae of Thomas L. Yearwood M.D., Ph.D.—Apr. 16, 2021," in Support of Petition for Inter Partes Review of U.S. Pat. No. 9,333,357, Case No. IPR2021-01023, Petitioner: *Nalu Medical, Inc.*; Patent Owner: *Nevro Corporation*, May 27, 2021, 8 pages.
Exhibit 1009—"United States Food and Drug Administration Premarket Approval ("PMA") Documents for PMA No. P030017, Precisiontm Spinal Cord Stimulation (SCS) System, dated Apr. 27, 2004 ("Precision SCS PMA")—Apr. 27, 2004" in Support of Petition for Inter Partes Review of U.S. Pat. No. 9,333,357, Case No. IPR2021-01023, Petitioner: *Nalu Medical, Inc.*; Patent Owner: *Nevro Corporation*, May 27, 2021, 8 pages.
Exhibit 1016—"Nakamura, S., Takahashi, K., Takahashi, Y., Yamagata, M., Moriya, H., The Afferent Pathways of Discogenic Low-Back Pain, 1996." in Support of Petition for Inter Partes Review of U.S. Pat. No. 9,333,357, Case No. IPR2021-01023, Petitioner: *Nalu Medical, Inc.*; Patent Owner: *Nevro Corporation*, May 27, 2021, 7 pages.
Exhibit 1017—"DKT. 185-1 Sep. 21, 2017 Ex. A Nevro Proposed Claim Construction, No. 3:16-cv-06830-VC." in Support of Petition for Inter Partes Review of U.S. Pat. No. 9,333,357, Case No. IPR2021-01023, Petitioner: *Nalu Medical, Inc.*; Patent Owner: *Nevro Corporation*, May 27, 2021, 118 pages.
Exhibit 1018—"Villavicencio et al.—Laminectomy versus Percutaneous Electrode Placement for Spinal Cord Stimulation—2000" in Support of Petition for Inter Partes Review of U.S. Pat. No. 9,333,357, Case No. IPR2021-01023, Petitioner: *Nalu Medical, Inc.*; Patent Owner: *Nevro Corporation*, May 27, 2021, 8 pages.
Exhibit 1020—"Demand for Jury Trial—Nevro First Amended Complaint, DKT. 14, Nevro v. Nalu, Case No. C.A. No. 20-291—Jun. 1, 2020" in Support of Petition for Inter Partes Review of U.S. Pat. No. 9,333,357, Case No. IPR2021-01023, Petitioner: *Nalu Medical, Inc.*; Patent Owner: *Nevro Corporation*, May 27, 2021, 36 pages.
Exhibit 1021—"North et al.—History of Spinal Cord Stimulation—2018" in Support of Petition for Inter Partes Review of U.S. Pat. No. 9,333,357, Case No. IPR2021-01023, Petitioner: *Nalu Medical, Inc.*; Patent Owner: *Nevro Corporation*, May 27, 2021, 10 pages.
Exhibit 1026—"2006 Program of Annual Meeting of Congress of Neurological Surgeons, Oct. 7-12, 2006" in Support of Petition for Inter Partes Review of U.S. Pat. No. 9,333,357, Case No. IPR2021-01023, Petitioner: *Nalu Medical, Inc.*; Patent Owner: *Nevro Corporation*, May 27, 2021, 84 pages.
Exhibit 1027—"Medtronic—Itrel EZ Model 7434A Patient Programmer User Manual" in Support of Petition for Inter Partes Review of U.S. Pat. No. 9,333,357, Case No. IPR2021-01023, Petitioner: *Nalu Medical, Inc.*; Patent Owner: *Nevro Corporation*, May 27, 2021, 154 pages.
Exhibit 1028—"Federal Register / vol. 69, No. 189 / Sep. 30, 2004" in Support of Petition for Inter Partes Review of U.S. Pat. No. 9,333,357, Case No. IPR2021-01023, Petitioner: *Nalu Medical, Inc.*; Patent Owner: *Nevro Corporation*, May 27, 2021, 3 pages.
Exhibit 1029—"Erickson DL.—Percutaneous trial of stimulation for patient selection for implantable stimulating devices. J Neurosurg. 1975" in Support of Petition for Inter Partes Review of U.S. Pat. No. 9,333,357, Case No. IPR2021-01023, Petitioner: *Nalu Medical, Inc.*; Patent Owner: *Nevro Corporation*, May 27, 2021, 5 pages.
Exhibit 1030—"North et al.—Chronic stimulation via percutaneously inserted epidural electrodes. Neurosurgery. 1977" in Support of Petition for Inter Partes Review of U.S. Pat. No. 9,333,357, Case No. IPR2021-01023, Petitioner: *Nalu Medical, Inc.*; Patent Owner: *Nevro Corporation*, May 27, 2021, 4 pages.
Boston Scientific's Response to the Summons to Attend Oral Proceedings for European Patent No. 2207587, *Nevro Corp.* vs. *Boston Scientific Neuromodulation Corporation*, filed Sep. 6, 2018, 31 pages.
Brief for Plaintiff—*Appellant Nevro Corp., Nevro Corp.* vs. *Boston Scientific Corporation and Boston Scientific Neuromodulation Corporation*, Case No. 3:16-cv-06830-VC-MEJ, filed Nov. 8, 2018, 341 pages.
Notice of Opposition for European Patent No. 3156099, Proprietor of the Patent: *Nevro Corporation*; Opponent: *Boston Scientific Neuromodulation Corporation*, Aug. 2, 2018, 27 pages.
Declaration of Rafael Carbunaru in Support of Boston Scientific's Invalidity Contentions, *Nevro Corp.* (Plaintiff) vs. *Boston Scientific Corporation and Boston Scientific Neuromodulation Corporation*, Case No. 3:16-cv-06830-VC, executed Mar. 17, 2017, 5 pages.
Exhibit A of Declaration of Rafael Carbunaru: "Physician Implant Manual—Precision," in Support in Support of Defendants *Boston Scientific Corporation's and Boston Scientific Neuromodulation Corporation's* Invalidity Contentions, Advanced Bionics, 2004, 62 pages.
Exhibit B of Declaration of Rafael Carbunaru: "Physician Lead Manual—Precision," in Support in Support of Defendants *Boston Scientific Corporation's and Boston Scientific Neuromodulation Corporation's* Invalidity Contentions, Advanced Bionics, 2004, 62 pages.
Exhibit C of Declaration of Rafael Carbunaru: "Patient System Handbook—Precision," in Support in Support of Defendants *Boston Scientific Corporation's and Boston Scientific Neuromodulation Corporation's* Invalidity Contentions, Advanced Bionics, 2004, 93 pages.
Defendant's *Boston Scientific Corporation's and Boston Scientific Neuromodulation Corporation's* Preliminary Invalidity Contentions, Case No. 3:16-cv-06830-VC, filed Mar. 17, 2017, 159 pages.
Exhibit A1: Invalidity Chart v. MacDonald (U.S. Pat. No. 5,776,170), Boston Scientific Corporation's and Boston Scientific Neuromodulation Corporation's Invalidity Contentions, *Nevro Corp. v. Boston*

(56) References Cited

OTHER PUBLICATIONS

*Scientific Corporation and Boston Scientific Neuromodulation Corporation*, Case No. 3:16-cv-06830-VC (N.D. Cal.), Mar. 17, 2017, 294 pages.
Exhibit A2: Invalidity Chart v. Spinner (U.S. Patent Application Publication No. 2007/0213771), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Mar. 17, 2017, 235 pages.
Exhibit A3: Invalidity Chart v. Knudson (U.S. Patent Application Publication No. 2007/0073354), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Mar. 17, 2017, 301 pages.
Exhibit A4: Invalidity Chart v. Butukhanov (Soviet Union Publication No. 1512625), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Mar. 17, 2017, 233 pages.
Exhibit A5: Invalidity Chart v. Sluijter (U.S. Pat. No. 6,246,912), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Mar. 17, 2017, 226 pages.
Exhibit A6: Invalidity Chart v. Kilgore (U.S. Pat. No. 7,389,145), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Mar. 17, 2017, 219 pages.
Exhibit A7: Invalidity Chart v. Royle (U.S. Patent Application Publication No. 2006/0009820), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Mar. 17, 2017, 188 pages.
Exhibit A8: Invalidity Chart v. King (U.S. Patent Application Publication No. 2007/0149148), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Mar. 17, 2017, 222 pages.
Exhibit A9: Invalidity Chart v. DeRidder (U.S. Patent Application Publication No. 2011/0184488), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Mar. 17, 2017, 266 pages.
Exhibit A10: Invalidity Chart v. Fang (U.S. Patent Application Publication No. 2009/0204173), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Mar. 17, 2017, 191 pages.
Exhibit B1: Invalidity Chart v. Boston Scientific's Precision Spinal Cord Stimulation System, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Mar. 17, 2017, 337 pages.
Exhibit C1: 35 U.S.C. § 103(a) Invalidity Chart, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Mar. 17, 2017, 400 pages.

Boston Scientific's Answer to First Amended Complaint and Defense, *Nevro Corp. vs. Boston Scientific Corporation and Boston Scientific Neuromodulation Corporation*, Case No. 3:16-cv-06830-VC, Jul. 13, 2017, 22 pages.
Defendant's First Amended Preliminary Invalidity Contentions, *Nevro Corp. v. Boston Scientific Corporation and Boston Scientific Neuromodulation Corporation*, Case No. 3:16-cv-06830-VC, Jun. 17, 2017, 93 pages.
Amended Exhibit C1 (amendments redlined): 35 U.S.C. § 103(a) Invalidity Chart, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Jun. 13, 2017, 423 pages.
First Amended Complaint for Patent Infringement and Declaratory Judgment, *Nevro Corp. v. Boston Scientific Corporation and Boston Scientific Neuromodulation Corporation*, Case No. 3:16-cv-06830-VC, Jun. 29, 2017, 45 pages.
Plaintiff Nevro Corp's Motion to Strike Inequitable Conduct Allegations From Defendants' Twelfth Affirmative Defense; Memorandum of Points and Authorities, *Nevro Corp. vs. Boston Scientific Corporation and Boston Scientific Neuromodulation Corporation*, Case No. 3:16-cv-06830-VC, Aug. 3, 2017, 10 pages.
Boston Scientific's Opposition to Nevro's Motion to Strike Inequitable Conduct Allegations from Defendants' Twelfth Affirmative Defense (ECF No. 172), *Nevro Corp. vs. Boston Scientific Corporation and Boston Scientific Neuromodulation Corporation*, Case No. 3:16-cv-06830-VC, Aug. 17, 2017, 17 pages.
Defendant's Second Amended Preliminary Invalidity Contentions, *Nevro Corp. vs. Boston Scientific Corporation and Boston Scientific Neuromodulation Corporation*, Case No. 3:16-cv-06830-VC, Aug. 10, 2017, 108 pages.
Exhibit A1 for Defendant's Second Amended Preliminary Invalidity Contentions: Invalidity Chart v. MacDonald (U.S. Pat. No. 5,776,170), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Aug. 10, 2017, 168 pages.
Exhibit A2 for Defendant's Second Amended Preliminary Invalidity Contentions: Invalidity Chart v. Spinner (U.S. Patent Application Publication No. 2007/0213771), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Aug. 10, 2017, 129 pages.
Exhibit A3 for Defendant's Second Amended Preliminary Invalidity Contentions: Invalidity Chart v. Knudson (U.S. Patent Application Publication No. 2007/0073354), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Aug. 10, 2017, 173 pages.
Exhibit A5 for Defendant's Second Amended Preliminary Invalidity Contentions: Invalidity Chart v. Sluijter (U.S. Pat. No. 6,246,912), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Aug. 10, 2017, 135 pages.
Exhibit A6 for Defendant's Second Amended Preliminary Invalidity Contentions: Invalidity Chart v. Kilgore (U.S. Pat. No. 7,389,145), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Aug. 10, 2017, 110 pages.
Exhibit A7 for Defendant's Second Amended Preliminary Invalidity Contentions: Invalidity Chart v. Royle (U.S. Patent Application Publication No. 2006/0009820), Boston Scientific Corporation's and Boston Scientific Neuromodulation Corporation's Invalidity Contentions, *Nevro Corp. v. Boston Scientific Corporation and*

(56) References Cited

OTHER PUBLICATIONS

*Boston Scientific Neuromodulation Corporation*, Case No. 3:16-cv-06830-VC (N.D. Cal.), Aug. 10, 2017, 111 pages.

Exhibit A9 for Defendant's Second Amended Preliminary Invalidity Contentions: Invalidity Chart v. DeRidder (U.S. Patent Application Publication No. 2011/0184488), Boston Scientific Corporation's and Boston Scientific Neuromodulation Corporation's Invalidity Contentions, *Nevro Corp.* v. *Boston Scientific Corporation and Boston Scientific Neuromodulation Corporation*, Case No. 3:16-cv-06830-VC (N.D. Cal.), Aug. 10, 2017, 160 pages.

Exhibit A10 for Defendant's Second Amended Preliminary Invalidity Contentions: Invalidity Chart v. Fang (U.S. Patent Application Publication No. 2009/0204173), Boston Scientific Corporation's and Boston Scientific Neuromodulation Corporation's Invalidity Contentions, *Nevro Corp.* v. *Boston Scientific Corporation and Boston Scientific Neuromodulation Corporation*, Case No. 3:16-cv-06830-VC (N.D. Cal.), Aug. 10, 2017, 114 pages.

Exhibit A11 for Defendant's Second Amended Preliminary Invalidity Contentions: Invalidity Chart v. Alataris (U.S. Pat. No. 8,712,533), Boston Scientific Corporation's and Boston Scientific Neuromodulation Corporation's Invalidity Contentions, *Nevro Corp.* v. *Boston Scientific Corporation and Boston Scientific Neuromodulation Corporation*, Case No. 3:16-cv-06830-VC (N.D. Cal.), Aug. 10, 2017, 13 pages.

Exhibit A12 for Defendant's Second Amended Preliminary Invalidity Contentions: Invalidity Chart v. Gaunt (U.S. Patent Publication No. 2006/0184211), Boston Scientific Corporation's and Boston Scientific Neuromodulation Corporation's Invalidity Contentions, *Nevro Corp.* v. *Boston Scientific Corporation and Boston Scientific Neuromodulation Corporation*, Case No. 3:16-cv-06830-VC (N.D. Cal.), Aug. 10, 2017, 113 pages.

Exhibit B1 for Defendant's Second Amended Preliminary Invalidity Contentions: Invalidity Chart v. Boston Scientific's Precision Spinal Cord Stimulation System, Boston Scientific Corporation's and Boston Scientific Neuromodulation Corporation's Invalidity Contentions, *Nevro Corp.* v. *Boston Scientific Corporation and Boston Scientific Neuromodulation Corporation*, Case No. 3:16-cv-06830-VC (N.D. Cal.), Aug. 10, 2017, 180 pages.

Exhibit C1 for Defendant's Second Amended Preliminary Invalidity Contentions: 35 U.S.C. § 103(a) Invalidity Chart, Boston Scientific Corporation's and Boston Scientific Neuromodulation Corporation's Invalidity Contentions, *Nevro Corp.* v. *Boston Scientific Corporation and Boston Scientific Neuromodulation Corporation*, Case No. 3:16-cv-06830-VC (N.D. Cal.), Aug. 10, 2017, 174 pages.

Corrected Exhibit C1 for Defendant's Second Amended Preliminary Invalidity Contentions: 35 U.S.C. § 103(a) Invalidity Chart, Boston Scientific Corporation's and Boston Scientific Neuromodulation Corporation's Invalidity Contentions, *Nevro Corp.* v. *Boston Scientific Corporation and Boston Scientific Neuromodulation Corporation*, Case No. 3:16-cv-06830-VC (N.D. Cal.), Aug. 10, 2017, 171 pages.

Statement of Grounds of Appeal for the Opposition of European Patent No. 2421600 (Appeal No. T1450/17-3.4.01) by Boston Scientific Neuromodulation Corporation, Aug. 14, 2017, 17 pages.

Nevro's Notice of Appeal for Opposition by Medtronic, Inc., and Boston Scientific Neuromodulation Corporation for European Patent No. 2243510, mailed Aug. 3, 2017, 1 page.

Provision of Minutes in accordance with Rule 124(4) EPC for Opposition by Medtronic, Inc., and Boston Scientific Neuromodulation Corporation for European Patent No. 2243510, mailed Jul. 27, 2017, 23 pages.

Decision Revoking the European Patent for Opposition by Medtronic, Inc., and Boston Scientific Neuromodulation Corporation for European Patent No. 2243510, mailed Jul. 27, 2017, 37 pages.

Nevro's Reply of the Patentee to the Notices of Opposition filed by Medtronic, Inc., and Boston Scientific Neuromodulation Corporation for EP2853285, filed Nov. 3, 2017, 34 pages.

Corrected Rebuttal Expert Report of Ben Pless Regarding Validity on behalf of Plaintiff Nevro Corp., regarding Invalidity of U.S. Pat. No. 8,712,533, U.S. Pat. No. 9,327,125, U.S. Pat. No. 8,359,102, U.S. Pat. No. 9,480,842, U.S. Pat. No. 9,333,357, U.S. Pat. No. 8,792,988, and U.S. Pat. No. 8,768,472, *Nevro Corp.* vs. *Boston Scientific Corporation and Boston Scientific Neuromodulation Corporation*, Case No. 3:16-cv-06830-VC-MEJ, Mar. 5, 2018, 785 pages.

Expert Report of Richard T. Mihran, Ph.D., regarding Invalidity of U.S. Pat. No. 8,712,533, U.S. Pat. No. 9,327,125, U.S. Pat. No. 8,359,102, U.S. Pat. No. 9,480,842, U.S. Pat. No. 9,333,357, U.S. Pat. No. 8,792,988, and U.S. Pat. No. 8,768,472, *Nevro Corp.* vs. *Boston Scientific Corporation and Boston Scientific Neuromodulation Corporation*, Case No. 3:16-cv-06830-VC-MEJ, Jan. 18, 2018, 958 pages.

Nevro Observations and Response to Notice of Oppositions filed by Medtronic Inc., and Boston Scientific for European Patent No. 2586488, mailed May 18, 2018, 87 pages.

Opponents Boston Scientific Neuromodulation Corporation: Response to Appeal in Opposition for European Patent No. 2243510, mailed May 2, 2018, 31 pages.

Opponents Medtronic, Inc.: Response to Appeal in Opposition for European Patent No. 2243510, mailed Apr. 30, 2018, 23 pages.

Rebuttal Expert Report of Richard T. Mihran, Ph.D., regarding Invalidity of U.S. Pat. No. 8,712,533, U.S. Pat. No. 9,327,125, U.S. Pat. No. 8,359,102, U.S. Pat. No. 9,480,842, U.S. Pat. No. 9,333,357, U.S. Pat. No. 8,792,988, and U.S. Pat. No. 8,768,472, *Nevro Corp.* vs. *Boston Scientific Corporation and Boston Scientific Neuromodulation Corporation*, Case No. 3:16-cv-06830-VC-MEJ, Feb. 14, 2018, 195 pages.

Additional Arguments to Notice of Opposition of European Patent No. 2853285, filed by Medtronic, Inc., on May 17, 2017, 9 pages.

Nevro Observations and Response to Notice of Oppositions filed by Medtronic Inc., and Boston Scientific for European Patent No. 2207587, mailed Aug. 26, 2016, 16 pages.

Nevro Response to Notice of Oppositions filed by Boston Scientific for European Patent No. 2421600, mailed Jul. 22, 2015, 16 pages.

Nevro Response to Notice of Oppositions filed by Medtronic and Boston Scientific for European Patent No. 2630984, mailed Dec. 7, 2015, 26 pages.

Nevro Response to Opposition of Division's Comments and Summons to Oral Proceedings for European Patent No. 2630984, mailed Oct. 25, 2016, 8 pages.

Nevro Written Submissions and Response to Notice of Oppositions filed by Medtronic Inc., and Boston Scientific for European Patent No. 2243510, mailed Aug. 28, 2015, 17 pages.

Nevro's Response to Preliminary Opinion for Opposition by Medtronic, Inc., and Boston Scientific Neuromodulation Corporation for European Patent No. 2243510, mailed Feb. 3, 2017, 36 pages.

Nevro's Statement of Grounds of Appeal for EP2243510 (Appeal No. T 17484/17-3.4.01), filed Nov. 30, 2017, 16 pages.

Nevro's Response to Further Submission by Medtronic, Inc., and Boston Scientific Neuromodulation Corporation for European Patent No. 2243510, mailed Feb. 24, 2017, 9 pages.

Nevros Response to Opponent Submission of Declaration of Jonathan Miller in European Patent No. 2630984, mailed Nov. 18, 2016, 4 pages.

Notice of Opposition to a European Patent for European Patent No. 2853285, Proprietor of the Patent: *Nevro Corporation*, Opponent: *Medtronic, Inc.*, Apr. 19, 2017, 40 pages.

Notice of Opposition to a European Patent for European Patent No. 2853285, Proprietor of the Patent: *Nevro Corporation*, Opponent: *Boston Scientific Neuromodulation Corporation*, May 16, 2017, 18 pages.

Notice of Opposition to a European Patent for European Patent No. 2586488, Proprietor of the Patent: *Nevro Corporation*, Opponent: *Medtronic, Inc.*, Mar. 15, 2017, 7 pages.

Notice of Opposition to a European Patent, Argument and Facts for European Patent No. 2630984, Proprietor of the Patent: *Nevro Corporation*; Opponent: *Medtronic*, Mar. 17, 2015, 17 pages.

Notice of Opposition to a European Patent, Argument and Facts, and Annex for European Patent No. 2630984, Proprietor of the Patent: *Nevro Corporation*; Opponent: *Boston Scientific Neuromodulation Corporation*, Mar. 17, 2015, 21 pages.

Notice of Opposition to a European Patent, Argument and Facts, and Annex for European Patent No. 2421600, Proprietor of the Patent:

(56) References Cited

OTHER PUBLICATIONS

*Nevro Corporation*; Opponent: *Boston Scientific Neuromodulation Corporation*, Dec. 4, 2014, 22 pages.
Notice of Opposition to a European Patent, Argument and Facts, for European Patent No. 2243510, Proprietor of the Patent: *Nevro Corporation*, Opponent: *Medtronic*, Jan. 8, 2015, 22 pages.
Notice of Opposition to a European Patent, Argument and Facts, and Annex for European Patent No. 2243510, Proprietor of the Patent: *Nevro Corporation*; Opponent: *Boston Scientific Neuromodulation Corporation*, Jan. 8, 2015, 28 pages.
Notice of Opposition to a European Patent, Argument and Facts, for European Patent No. 2207587, Proprietor of the Patent: *Nevro Corporation*; Opponent: *Medtronic, Inc.*, Jan. 12, 2016, 22 pages.
Notice of Opposition to a European Patent, Argument and Facts, for European Patent No. 2207587, Proprietor of the Patent: *Nevro Corporation*; Opponent: *Boston Scientific Neuromodulation Corporation*, Jan. 8, 2016, 17 pages.
Notice of Opposition to a European Patent, Argument and Facts, for European Patent No. 2586488, Proprietor of the Patent: *Nevro Corporation*; Opponent: *Boston Scientific Neuromodulation Corporation*, Dec. 15, 2017, 35 pages.
Opponent Boston Scientific: Response to Attend Oral Proceedings for European Patent No. 2630984, mailed Oct. 25, 2016, 21 pages.
Opponent Response to Patent Proprietor Comments to Declaration of Dr. Jonathan Miller for European Patent No. 2630984, mailed Nov. 22, 2016, 3 pages.
Opponents Boston Scientific Neuromodulation Corp.: Additional Observations in view of Oral Proceedings for European Patent No. 2243510, mailed Feb. 3, 2017, 8 pages.
Opponents Boston Scientific Neuromodulation Corporation: Response to Nov. 9, 2017 Brief Communication in Opposition for European Patent No. 2853285, mailed Feb. 13, 2018, 9 pages.
Opponents Boston Scientific: Response to Summons to Attend Oral Proceedings for European Patent No. 2421600, mailed Jan. 2, 2017, 15 pages.
Opponents Medtronic, Inc.: Additional Observations in view of Oral Proceedings for European Patent No. 2243510, mailed Feb. 3, 2017, 10 pages.
Opponents Medtronic, Inc.: Facts and Arguments in Support of Opposition for European Patent No. 2586488, mailed Dec. 15, 2017, 18 pages.
Opponents Medtronic, Inc.: Response to Attend Oral Proceedings for European Patent No. 2630984, mailed Oct. 25, 2016, 26 pages.
Opponents Medtronic: Response to Nevro Requests and Submission for European Patent No. 22453510, mailed Mar. 29, 2017, 3 pages.
Opponents Response to Patentee's (Nevro) Written Submissions for European Patent No. 2243510, mailed Feb. 22, 2016, 21 pages.
Nevro's Motion for Summary Adjudication—Notice of Motion, Motion and Memorandum of Points and Authorities in the Support of Nevro's Motion for Summary Adjudication (Document 461), *Nevro Corp. vs. Boston Scientific Corporation and Boston Scientific Neuromodulation Corporation*, Case No. 3:16-cv-06830-VC-MEJ, filed Jul. 30, 2018, 50 pages.
Declaration of Konstantinos Alataris in Support of Nevro's Motion of Summary Adjudication (Document 342-1), *Nevro Corp. vs. Boston Scientific Corporation and Boston Scientific Neuromodulation Corporation*, Case No. 3:16-cv-06830-VC-MEJ, Apr. 11, 2018, 3 pages.
Exhibit 1 for Declaration of Konstantinos Alataris in Support of Nevro's Motion of Summary Adjudication (Document 342-2), Notes from NBI Mayo Physician Meeting Dec. 4, 2016, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Apr. 12, 2018, 3 pages.
Exhibit 2 for Declaration of Konstantinos Alataris in Support of Nevro's Motion of Summary Adjudication (Document 342-3), Notes from NBI Development—Mayo Clinic Dec. 4, 2016, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 11 pages.
Exhibit 3 for Declaration of Konstantinos Alataris in Support of Nevro's Motion of Summary Adjudication (Document 342-4), Sep. 2007 Email between O. Filho and Konstantinos Alataris, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 4 pages.
Exhibit 4 for Declaration of Konstantinos Alataris in Support of Nevro's Motion of Summary Adjudication (Document 342-5) NBI Development Inc., Jun. 12, 2007 Board Meeting, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 31 pages.
Declaration of Ben Pless in Support of Nevro's Motion for Summary Adjudication (Updated Redacted Version of EFC No. 347-24), *Nevro Corp. vs. Boston Scientific Corporation and Boston Scientific Neuromodulation Corporation*, Case No. 3:16-cv-06830-VC-MEJ, Apr. 11, 2018, 64 pages.
Exhibit A for Declaration of Ben Pless in Support of Nevro's Motion for Summary Adjudication (Document 342-7) Curriculum Vitae of Benjamin Pless, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Jul. 30, 2018, 15 pages.
Declaration of Eric C. Pai in Support of Nevro's Motion for Summary Adjudication (Document 343), *Nevro Corp. vs. Boston Scientific Corporation and Boston Scientific Neuromodulation Corporation*, Case No. 3:16-cv-06830-VC-MEJ, Apr. 12, 2018, 11 pages.
Exhibit 1 for Declaration of Eric C. Pai in Support of Nevro's Motion for Summary Adjudication (Document 343-1) Chart—Asserted Claims with Disputed Terms Underlined, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 5 pages.
Exhibit 2 for Declaration of Eric C. Pai in Support of Nevro's Motion for Summary Adjudication (Document 343-2) Certified Copy of U.S. Pat. No. 8,359,102, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 34 pages.
Exhibit 3 for Declaration of Eric C. Pai in Support of Nevro's Motion for Summary Adjudication (Document 343-3) Certified Copy of U.S. Pat. No. 8,712,533, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 37 pages.
Exhibit 4 for Declaration of Eric C. Pai in Support of Nevro's Motion for Summary Adjudication (Document 343-4) Certified Copy of U.S. Pat. No. 8,768,472, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 37 pages.
Exhibit 5 for Declaration of Eric C. Pai in Support of Nevro's Motion for Summary Adjudication (Document 343-5) Certified Copy of U.S. Pat. No. 8,792,988, Boston Scientific Corporation's and Boston Scientific Neuromodulation Corporation's Invalidity Contentions, *Nevro Corp. v. Boston Scientific Corporation and*

(56) References Cited

OTHER PUBLICATIONS

*Boston Scientific Neuromodulation Corporation*, Case No. 3:16-cv-06830-VC (N.D. Cal.), filed Apr. 12, 2018, 35 pages.
Exhibit 6 for Declaration of Eric C. Pai in Support of Nevro's Motion for Summary Adjudication (Document 343-6) Certified Copy of U.S. Pat. No. 9,327,125, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 40 pages.
Exhibit 7 for Declaration of Eric C. Pai in Support of Nevro's Motion for Summary Adjudication (Document 343-7) Certified Copy of U.S. Pat. No. 9,333,357, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 39 pages.
Exhibit 8 for Declaration of Eric C. Pai in Support of Nevro's Motion for Summary Adjudication (Document 343-8) Certified Copy of U.S. Pat. No. 9,480,842, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 38 pages.
Exhibit 9 for Declaration of Eric C. Pai in Support of Nevro's Motion for Summary Adjudication (Document 343-9) Article by Leonardo Kapural et al., Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 11 pages.
Exhibit 10 for Declaration of Eric C. Pai in Support of Nevro's Motion for Summary Adjudication (Document 343-10) Article by Antonio Foletti et al., Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 15 pages.
Exhibit 11 for Declaration of Eric C. Pai in Support of Nevro's Motion for Summary Adjudication (Document 343-11) Article by Leonardo Kapural et al., Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 12 pages.
Exhibit 12 for Declaration of Eric C. Pai in Support of Nevro's Motion for Summary Adjudication (Document 343-12) Poster by Mark Wallace et al., Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 2 pages.
Exhibit 13 for Declaration of Eric C. Pai in Support of Nevro's Motion for Summary Adjudication (Document 343-13) Summary of Safety and Effectiveness Data (SSED), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 6 pages.
Exhibit 14 for Declaration of Eric C. Pai in Support of Nevro's Motion for Summary Adjudication (Document 343-14) Nevro—Notes from Las Vegas and Our Survey of 50 US pain docs, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 19 pages.
Exhibit 15 for Declaration of Eric C. Pai in Support of Nevro's Motion for Summary Adjudication (Document 343-15) Apr. 2012 Email between K. Bradley and J. Cassidy, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 5 pages.
Exhibit 16 for Declaration of Eric C. Pai in Support of Nevro's Motion for Summary Adjudication (Document 343-16) Entire Document Sealed, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 1 page.
Exhibit 17 for Declaration of Eric C. Pai in Support of Nevro's Motion for Summary Adjudication (Document 343-17) Entire Document Sealed, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 1 page.
Exhibit 18 for Declaration of Eric C. Pai in Support of Nevro's Motion for Summary Adjudication (Document 343-18) Entire Document Sealed, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 1 page.
Exhibit 19 for Declaration of Eric C. Pai in Support of Nevro's Motion for Summary Adjudication (Document 343-19) Entire Document Sealed, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 1 page.
Exhibit 20 for Declaration of Eric C. Pai in Support of Nevro's Motion for Summary Adjudication (Document 343-20) Redacted Version of Document Sought to be Sealed—Excerpts from May 18, 2018 Deposition of R. Carbunaru, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 12 pages.
Exhibit 21 for Declaration of Eric C. Pai in Support of Nevro's Motion for Summary Adjudication (Document 343-21) Certified Copy of U.S. Pat. No. 8,792,988, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 9 pages.
Exhibit 22 for Declaration of Eric C. Pai in Support of Nevro's Motion for Summary Adjudication (Document 462) Updated Redacted Version of ECF No. 347-10—Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Jul. 30, 2018, 9 pages.
Exhibit 23 for Declaration of Eric C. Pai in Support of Nevro's Motion for Summary Adjudication (Document 463) Updated Redacted Version of ECF No. 347-12, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Jul. 30, 2018, 23 pages.
Exhibit 24 for Declaration of Eric C. Pai in Support of Nevro's Motion for Summary Adjudication (Document 343-24) Redacted Version of Document Sought to Be Sealed—BSC's Supplemental Responses and Objections to Nevro First Set of Interrogatory Request, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 11 pages.
Exhibit 25 for Declaration of Eric C. Pai in Support of Nevro's Motion for Summary Adjudication (Document 464) Updated Redacted Version of ECF No. 347-16—BSC's Second Supplemental Responses

(56) References Cited

OTHER PUBLICATIONS and Objections to Nevro First Set of Interrogatory Request, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 12 pages.
Exhibit 26 for Declaration of Eric C. Pai in Support of Nevro's Motion for Summary Adjudication (Document 343-26) Decision Denying Institution of Inter Partes Review 37 CFR § 42.108—IPR2015-01203 U.S. Pat. No. 8,359,102, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 21 pages.
Exhibit 27 for Declaration of Eric C. Pai in Support of Nevro's Motion for Summary Adjudication (Document 343-27) Decision Denying Institution of Inter Partes Review 37 CFR § 42.108—IPR2015-01204 U.S. Pat. No. 8,359,102, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 15 pages.
Exhibit 28 for Declaration of Eric C. Pai in Support of Nevro's Motion for Summary Adjudication (Document 343-28) Certified Copy of U.S. Pat. No. 9,333,357, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 13 pages.
Exhibit 29 for Declaration of Eric C. Pai in Support of Nevro's Motion for Summary Adjudication (Document 343-29) Rebuttal Expert Report and Declaration of Gene Fridman, Ph.D., regarding Claim Construction—Feb. 14, 2018, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 13 pages.
Exhibit 30 for Declaration of Eric C. Pai in Support of Nevro's Motion for Summary Adjudication (Document 343-30) Deposition of Dr. Gene Fridman on Mar. 7, 2018, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 49 pages.
Exhibit 31 for Declaration of Eric C. Pai in Support of Nevro's Motion for Summary Adjudication (Document 343-31) Rebuttal Expert Report and Declaration of Gene Fridman, Ph.D., regarding Claim Construction—Jan. 18, 2018, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 12 pages.
Exhibit 32 for Declaration of Eric C. Pai in Support of Nevro's Motion for Summary Adjudication (Document 343-32) Deposition of Kaoru Lee Adair—May 10, 2017, Entire Document Sought to be Sealed, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 1 page.
Exhibit 33 for Declaration of Eric C. Pai in Support of Nevro's Motion for Summary Adjudication (Document 343-33) Expert Report and Declaration of Adam Lipson, M.D., pursuant to Federal Rule of Civil Procedure 26(A)(2)(B) dated Jan. 18, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 4 pages.
Exhibit 34 for Declaration of Eric C. Pai in Support of Nevro's Motion for Summary Adjudication (Document 343-34) Stedman's Medical Dictionary 27th Edition, definition "paresthesia", Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 4 pages.
Exhibit 35 for Declaration of Eric C. Pai in Support of Nevro's Motion for Summary Adjudication (Document 343-35) Dorland's Illustrated Medical Dictionary, definition "paresthesia", Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 4 pages.
Exhibit 36 for Declaration of Eric C. Pai in Support of Nevro's Motion for Summary Adjudication (Document 343-36) Mosby's Medical Dictionary, definition "paresthesia", Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 5 pages.
Exhibit 37 for Declaration of Eric C. Pai in Support of Nevro's Motion for Summary Adjudication (Document 343-37) National Institute of Neurological Disorders and Stroke—Paresthesia Information Page, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 4 pages.
Exhibit 38 for Declaration of Eric C. Pai in Support of Nevro's Motion for Summary Adjudication (Document 343-38) Videotaped Deposition of Richard T. Mihran, Ph.D. on Mar. 12, 2018, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 10 pages.
Exhibit 39 for Declaration of Eric C. Pai in Support of Nevro's Motion for Summary Adjudication (Document 343-39) Boston Scientific—Precision Spinal Cord Stimulator System with MultiWave Technology Clinician Manual,, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 68 pages.
Exhibit 40 for Declaration of Eric C. Pai in Support of Nevro's Motion for Summary Adjudication (Document 343-40) BSC's Amended and Supplemental Responses and Objections to Nevro's Second Set of Interrogatories (Nos. 9, 10) dated Aug. 24, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 18 pages.
Exhibit 41 for Declaration of Eric C. Pai in Support of Nevro's Motion for Summary Adjudication (Document 343-41) Rebuttal Expert Report of Richard T. Mihran, Ph.D. dated Feb. 14, 2018, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 23 pages.
Exhibit 42 for Declaration of Eric C. Pai in Support of Nevro's Motion for Summary Adjudication (Document 343-42) Redacted Version of Document Sought to be Sealed—Videotaped Deposition of Nevro Corp. with designated corporate representative Jim Cassidy on May 17, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 5 pages.

(56) References Cited

OTHER PUBLICATIONS

Exhibit 43 for Declaration of Eric C. Pai in Support of Nevro's Motion for Summary Adjudication (Document 343-43) Entire Document Sought to be Sealed—Deposition of Kaoru Lee Adair taken on May 10, 2017, Boston Scientific Corporation's and Boston Scientific Neuromodulation Corporation's Invalidity Contentions, *Nevro Corp.* v. *Boston Scientific Corporation and Boston Scientific Neuromodulation Corporation*, Case No. 3:16-cv-06830-VC (N.D. Cal.), filed Apr. 12, 2018, 1 page.
Exhibit 44 for Declaration of Eric C. Pai in Support of Nevro's Motion for Summary Adjudication (Document 343-44) Entire Document Sought to be Sealed—Deposition of Kaoru Lee Adair taken on May 10, 2017, Boston Scientific Corporation's and Boston Scientific Neuromodulation Corporation's Invalidity Contentions, *Nevro Corp.* v. *Boston Scientific Corporation and Boston Scientific Neuromodulation Corporation*, Case No. 3:16-cv-06830-VC (N.D. Cal.), filed Apr. 12, 2018, 1 page.
Exhibit 45 for Declaration of Eric C. Pai in Support of Nevro's Motion for Summary Adjudication (Document 343-45) Entire Document Sought to be Sealed—Deposition of Kaoru Lee Adair taken on May 10, 2017, Boston Scientific Corporation's and Boston Scientific Neuromodulation Corporation's Invalidity Contentions, *Nevro Corp.* v. *Boston Scientific Corporation and Boston Scientific Neuromodulation Corporation*, Case No. 3:16-cv-06830-VC (N.D. Cal.), filed Apr. 12, 2018, 1 page.
Exhibit 46 for Declaration of Eric C. Pai in Support of Nevro's Motion for Summary Adjudication (Document 343-46) Entire Document Sought to be Sealed—Deposition of Kaoru Lee Adair taken on May 10, 2017, Boston Scientific Corporation's and Boston Scientific Neuromodulation Corporation's Invalidity Contentions, *Nevro Corp.* v. *Boston Scientific Corporation and Boston Scientific Neuromodulation Corporation*, Case No. 3:16-cv-06830-VC (N.D. Cal.), filed Apr. 12, 2018, 1 page.
Exhibit 47 for Declaration of Eric C. Pai in Support of Nevro's Motion for Summary Adjudication (Document 343-47) Entire Document Sought to be Sealed—Deposition of Kaoru Lee Adair taken on May 10, 2017, Boston Scientific Corporation's and Boston Scientific Neuromodulation Corporation's Invalidity Contentions, *Nevro Corp.* v. *Boston Scientific Corporation and Boston Scientific Neuromodulation Corporation*, Case No. 3:16-cv-06830-VC (N.D. Cal.), filed Apr. 12, 2018, 1 page.
Exhibit 48 for Declaration of Eric C. Pai in Support of Nevro's Motion for Summary Adjudication (Document 343-48) Defendant's Identification of 40 Prior Art Grounds for Invalidity dated Dec. 22, 2017, Boston Scientific Corporation's and Boston Scientific Neuromodulation Corporation's Invalidity Contentions, *Nevro Corp.* v. *Boston Scientific Corporation and Boston Scientific Neuromodulation Corporation*, Case No. 3:16-cv-06830-VC (N.D. Cal.), filed Apr. 12, 2018, 4 pages.
Exhibit 49 for Declaration of Eric C. Pai in Support of Nevro's Motion for Summary Adjudication (Document 343-49) Defendant's Second Amended Preliminary Invalidity Contentions dated Aug. 10, 2017, Boston Scientific Corporation's and Boston Scientific Neuromodulation Corporation's Invalidity Contentions, *Nevro Corp.* v. *Boston Scientific Corporation and Boston Scientific Neuromodulation Corporation*, Case No. 3:16-cv-06830-VC (N.D. Cal.), filed Apr. 12, 2018, 47 pages.
Exhibit 50 for Declaration of Eric C. Pai in Support of Nevro's Motion for Summary Adjudication (Document 343-50) Declaration of Rafael Carbunaru in Support of Boston Scientific's Invalidity Contentions dated Mar. 17, 2017, Boston Scientific Corporation's and Boston Scientific Neuromodulation Corporation's Invalidity Contentions, *Nevro Corp.* v. *Boston Scientific Corporation and Boston Scientific Neuromodulation Corporation*, Case No. 3:16-cv-06830-VC (N.D. Cal.), filed Apr. 12, 2018, 6 pages.
Exhibit 51 for Declaration of Eric C. Pai in Support of Nevro's Motion for Summary Adjudication (Document 343-51) Declaration of Kaoru Lee Adair in Support of Boston Scientific's Motion to Dismiss Nevro's Declaratory Judgment Claims dated Dec. 27, 2016, Boston Scientific Corporation's and Boston Scientific Neuromodulation Corporation's Invalidity Contentions, *Nevro Corp.* v. *Boston Scientific Corporation and Boston Scientific Neuromodulation Corporation*, Case No. 3:16-cv-06830-VC (N.D. Cal.), filed Apr. 12, 2018, 5 pages.
Exhibit 52 for Declaration of Eric C. Pai in Support of Nevro's Motion for Summary Adjudication (Document 343-52) Expert Report of Richard T. Mihran, Ph.D., regarding Invalidity of U.S. Pat. No. 8,712,533; U.S. Pat. No. 9,327,125; U.S. Pat. No. 8,359,102; U.S. Pat. No. 9,480,842; U.S. Pat. No. 9,333,357; U.S. Pat. No. 8,792,988; and U.S. Pat. No. 8,768,472 dated Jan. 18, 2018, Boston Scientific Corporation's and Boston Scientific Neuromodulation Corporation's Invalidity Contentions, *Nevro Corp.* v. *Boston Scientific Corporation and Boston Scientific Neuromodulation Corporation*, Case No. 3:16-cv-06830-VC (N.D. Cal.), filed Apr. 12, 2018, 78 pages.
Exhibit 53 for Declaration of Eric C. Pai in Support of Nevro's Motion for Summary Adjudication (Document 343-53) Redacted Version of Document Sought to be Sealed—Rebuttal Expert Report and Declaration of Daniel Lanovaz dated Feb. 14, 2017, Boston Scientific Corporation's and Boston Scientific Neuromodulation Corporation's Invalidity Contentions, *Nevro Corp.* v. *Boston Scientific Corporation and Boston Scientific Neuromodulation Corporation*, Case No. 3:16-cv-06830-VC (N.D. Cal.), filed Apr. 12, 2018, 6 pages.
Exhibit 54 for Declaration of Eric C. Pai in Support of Nevro's Motion for Summary Adjudication (Document 343-54) Certified Copy of U.S. Pat. No. 8,712,533, Boston Scientific Corporation's and Boston Scientific Neuromodulation Corporation's Invalidity Contentions, *Nevro Corp.* v. *Boston Scientific Corporation and Boston Scientific Neuromodulation Corporation*, Case No. 3:16-cv-06830-VC (N.D. Cal.), filed Apr. 12, 2018, 13 pages.
Exhibit 55 for Declaration of Eric C. Pai in Support of Nevro's Motion for Summary Adjudication (Document 343-55) U.S. Patent Application No. 2009/0204173 to Fang et al., Boston Scientific Corporation's and Boston Scientific Neuromodulation Corporation's Invalidity Contentions, *Nevro Corp.* v. *Boston Scientific Corporation and Boston Scientific Neuromodulation Corporation*, Case No. 3:16-cv-06830-VC (N.D. Cal.), filed Apr. 12, 2018, 33 pages.
Exhibit 56 for Declaration of Eric C. Pai in Support of Nevro's Motion for Summary Adjudication (Document 343-56) Deposition of Konstantinos Alataris dated Nov. 14, 2017, Boston Scientific Corporation's and Boston Scientific Neuromodulation Corporation's Invalidity Contentions, *Nevro Corp.* v. *Boston Scientific Corporation and Boston Scientific Neuromodulation Corporation*, Case No. 3:16-cv-06830-VC (N.D. Cal.), filed Apr. 12, 2018, 34 pages.
Exhibit 57 for Declaration of Eric C. Pai in Support of Nevro's Motion for Summary Adjudication (Document 343-57) Videotaped Deposition of Andre B. Walker dated Nov. 10, 2017, Boston Scientific Corporation's and Boston Scientific Neuromodulation Corporation's Invalidity Contentions, *Nevro Corp.* v. *Boston Scientific Corporation and Boston Scientific Neuromodulation Corporation*, Case No. 3:16-cv-06830-VC (N.D. Cal.), filed Apr. 12, 2018, 26 pages.
Exhibit 58 for Declaration of Eric C. Pai in Support of Nevro's Motion for Summary Adjudication (Document 343-58) Videotaped Deposition of Zi-Ping Fang dated Nov. 2, 2017, Boston Scientific Corporation's and Boston Scientific Neuromodulation Corporation's Invalidity Contentions, *Nevro Corp.* v. *Boston Scientific Corporation and Boston Scientific Neuromodulation Corporation*, Case No. 3:16-cv-06830-VC (N.D. Cal.), filed Apr. 12, 2018, 12 pages.
Exhibit 59 for Declaration of Eric C. Pai in Support of Nevro's Motion for Summary Adjudication (Document 343-59) Videotaped Deposition of Anthony Vincent Caparso dated Nov. 2, 2017, Boston Scientific Corporation's and Boston Scientific Neuromodulation Corporation's Invalidity Contentions, *Nevro Corp.* v. *Boston Scientific Corporation and Boston Scientific Neuromodulation Corporation*, Case No. 3:16-cv-06830-VC (N.D. Cal.), filed Apr. 12, 2018, 8 pages.
Exhibit 60 for Declaration of Eric C. Pai in Support of Nevro's Motion for Summary Adjudication (Document 343-60) Videotaped

(56) References Cited

OTHER PUBLICATIONS

Deposition of Brian Erickson dated Dec. 15, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 44 pages.

Exhibit 61 for Declaration of Eric C. Pai in Support of Nevro's Motion for Summary Adjudication (Document 343-61) Deposition of Yougandh Chitre dated Nov. 20, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 6 pages.

Exhibit 62 for Declaration of Eric C. Pai in Support of Nevro's Motion for Summary Adjudication (Document 343-62) Deposition of Jon Parker dated Nov. 27, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 8 pages.

Exhibit 63 for Declaration of Eric C. Pai in Support of Nevro's Motion for Summary Adjudication (Document 343-63) Deposition of Jon Parker dated Nov. 16, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 8 pages.

Exhibit 64 for Declaration of Eric C. Pai in Support of Nevro's Motion for Summary Adjudication (Document 343-64) Videotaped James Thacker dated Dec. 7, 2017 (vol. 1), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 10 pages.

Exhibit 65 for Declaration of Eric C. Pai in Support of Nevro's Motion for Summary Adjudication (Document 343-65) Sep. 2007 Email between O. Filho and K. Alataris, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 4 pages.

Exhibit 66 for Declaration of Eric C. Pai in Support of Nevro's Motion for Summary Adjudication (Document 343-66) Redacted Version of Document Sought to be Sealed—BSC's Dec. 1, 2017 Supplemental Responses and Objections to Nevro's Second Set of Interrogatories (Nos. 10 and 14), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 13 pages.

Exhibit 67 for Declaration of Eric C. Pai in Support of Nevro's Motion for Summary Adjudication (Document 343-67) Certified Copy of U.S. Appl. No. 60/985,353, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 63 pages.

Exhibit 68 for Declaration of Eric C. Pai in Support of Nevro's Motion for Summary Adjudication (Document 343-68) Certified Copy of U.S. Appl. No. 12/264,836, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 67 pages.

Exhibit 69 for Declaration of Eric C. Pai in Support of Nevro's Motion for Summary Adjudication (Document 343-69) Certified Copy for U.S. Appl. No. 12/264,836, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 119 pages.

Exhibit 70 for Declaration of Eric C. Pai in Support of Nevro's Motion for Summary Adjudication (Document 343-70) Request to Add to Originally Named Inventors for U.S. Appl. No. 12/264,836, filed Aug. 13, 2012, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 27 pages.

Exhibit 71 for Declaration of Eric C. Pai in Support of Nevro's Motion for Summary Adjudication (Document 343-71) Poster by Yearwood et al., Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 8 pages.

Exhibit 72 for Declaration of Eric C. Pai in Support of Nevro's Motion for Summary Adjudication (Document 343-72) Case Report by Yearwood et al., Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 3 pages.

Exhibit 73 for Declaration of Eric C. Pai in Support of Nevro's Motion for Summary Adjudication (Document 343-73) Entire Document Sought to be Sealed—Deposition of Rafael Carbunaru taken on Nov. 14, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 1 page.

Exhibit 74 for Declaration of Eric C. Pai in Support of Nevro's Motion for Summary Adjudication (Document 343-74) Deposition of David Caraway dated Nov. 14, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 9 pages.

Exhibit 75 for Declaration of Eric C. Pai in Support of Nevro's Motion for Summary Adjudication (Document 343-75) Boston Scientific document, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 5 pages.

Declaration of Carson D. Anderson in Support of Nevro's Administrative Motion to File under Seal Portions of Nevro's Motion for Summary Adjudication and Supporting Documents (Document 348), *Nevro Corp. vs. Boston Scientific Corporation and Boston Scientific Neuromodulation Corporation*, Case No. 3:16-cv-06830-VC-MEJ, Apr. 16, 2018, 10 pages.

Exhibit A for Declaration of Carson D. Anderson in Support of Nevro's Administrative Motion to File under Seal Portions of Nevro's Motion for Summary Adjudication and Supporting Documents (Document 347-1) Redacted Version of Document Sought to Be Filed under Seal—Nevro's Notice of Motion, *Nevro Corp. vs. Boston Scientific Corporation and Boston Scientific Neuromodulation Corporation*, Case No. 3:16-cv-06830-VC-MEJ, Apr. 16, 2018, 50 pages.

Exhibit A—Updated—for Declaration of Carson D. Anderson in Support of Nevro's Administrative Motion to File under Seal Portions of Nevro's Motion for Summary Adjudication and Supporting Documents (Document 347-2 / Document 461) Redacted Version of Document Sought to Be Filed under Seal—Nevro's Motion for Summary Adjudication, *Nevro Corp. vs. Boston Scientific Corporation and Boston Scientific Neuromodulation Corporation*, Case No. 3:16-cv-06830-VC-MEJ, Jul. 30, 2018, 50 pages.

Exhibit B for Declaration of Carson D. Anderson in Support of Nevro's Administrative Motion to File under Seal Portions of Nevro's Motion for Summary Adjudication and Supporting Documents (Document 347-3) Redacted Version of Document Sought to

(56) References Cited

OTHER PUBLICATIONS

Be Filed under Seal—Videotaped Deposition of Rafael Carbunaru, Ph.D., taken Nov. 15, 2017, *Nevro Corp. vs. Boston Scientific Corporation and Boston Scientific Neuromodulation Corporation*, Case No. 3:16-cv-06830-VC-MEJ, filed Apr. 16, 2018, 46 pages.
Exhibit C for Declaration of Carson D. Anderson in Support of Nevro's Administrative Motion to File under Seal Portions of Nevro's Motion for Summary Adjudication and Supporting Documents (Document 347-5) Boston Scientific Neuromodulation—Sprint High Rate—Product Opportunity Proposal, *Nevro Corp. vs. Boston Scientific Corporation and Boston Scientific Neuromodulation Corporation*, Case No. 3:16-cv-06830-VC-MEJ, filed Apr. 16, 2018, 14 pages.
Exhibit D for Declaration of Carson D. Anderson in Support of Nevro's Administrative Motion to File under Seal Portions of Nevro's Motion for Summary Adjudication and Supporting Documents (Document 347-7) Redacted Version of Document Sought to be Filed under Seal—Boston Scientific Neuromodulation—Sprint High Rate—Project Authorization Review, *Nevro Corp. vs. Boston Scientific Corporation and Boston Scientific Neuromodulation Corporation*, Case No. 3:16-cv-06830-VC-MEJ, filed Apr. 16, 2018, 7 pages.
Exhibit E for Declaration of Carson D. Anderson in Support of Nevro's Administrative Motion to File under Seal Portions of Nevro's Motion for Summary Adjudication and Supporting Documents (Document 347-9) Redacted Version of Document Sought to be Filed under Seal—Videotaped Deposition of Kaoru Lee Adair, *Nevro Corp. vs. Boston Scientific Corporation and Boston Scientific Neuromodulation Corporation*, Case No. 3:16-cv-06830-VC-MEJ, filed Apr. 16, 2018, 12 pages.
Exhibit E—Updated—for Declaration of Carson D. Anderson in Support of Nevro's Administrative Motion to File under Seal Portions of Nevro's Motion for Summary Adjudication and Supporting Documents (Document 347-10) Redacted Version of Document Sought to be Filed under Seal—Videotaped Deposition of Kaoru Lee Adair, taken Nov. 17, 2017, *Nevro Corp. vs. Boston Scientific Corporation and Boston Scientific Neuromodulation Corporation*, Case No. 3:16-cv-06830-VC-MEJ, filed Apr. 16, 2018, 12 pages.
Exhibit F for Declaration of Carson D. Anderson in Support of Nevro's Administrative Motion to File under Seal Portions of Nevro's Motion for Summary Adjudication and Supporting Documents (Document 347-11) Redacted Version of Document Sought to be Filed under Seal—Videotaped Deposition of Kaoru Lee Adair, taken May 10, 2017, *Nevro Corp. vs. Boston Scientific Corporation and Boston Scientific Neuromodulation Corporation*, Case No. 3:16-cv-06830-VC-MEJ, filed Apr. 16, 2018, 23 pages.
Exhibit F—Updated—for Declaration of Carson D. Anderson in Support of Nevro's Administrative Motion to File under Seal Portions of Nevro's Motion for Summary Adjudication and Supporting Documents (Document 347-12) Redacted Version of Document Sought to be Filed under Seal—Videotaped Deposition of Kaoru Lee Adair, taken May 10, 2017, *Nevro Corp. vs. Boston Scientific Corporation and Boston Scientific Neuromodulation Corporation*, Case No. 3:16-cv-06830-VC-MEJ, filed Apr. 16, 2018, 23 pages.
Exhibit G for Declaration of Carson D. Anderson in Support of Nevro's Administrative Motion to File under Seal Portions of Nevro's Motion for Summary Adjudication and Supporting Documents (Document 347-13) BSC's Supplemental Responses and Objections to Nevro's First Set of Interrogatory Requests (1-8), *Nevro Corp. vs. Boston Scientific Corporation and Boston Scientific Neuromodulation Corporation*, Case No. 3:16-cv-06830-VC-MEJ, filed Apr. 16, 2018, 12 pages.
Exhibit H for Declaration of Carson D. Anderson in Support of Nevro's Administrative Motion to File under Seal Portions of Nevro's Motion for Summary Adjudication and Supporting Documents (Document 347-15) Redacted Version of Document Sought to be Filed under Seal—BSC's Second Supplemental Responses and Objections to Nevro's First Set of Interrogatory Requests (1-8), *Nevro Corp. vs. Boston Scientific Corporation and Boston Scientific Neuromodulation Corporation*, Case No. 3:16-cv-06830-VC-MEJ, filed Apr. 16, 2018, 12 pages.
Exhibit H—Updated—for Declaration of Carson D. Anderson in Support of Nevro's Administrative Motion to File under Seal Portions of Nevro's Motion for Summary Adjudication and Supporting Documents (Document 347-16) Updated Redacted Version of Document Sought to be Filed under Seal—BSC's Second Supplemental Responses and Objections to Nevro's First Set of Interrogatory Requests (1-8), *Nevro Corp. vs. Boston Scientific Corporation and Boston Scientific Neuromodulation Corporation*, Case No. 3:16-cv-06830-VC-MEJ, filed Apr. 16, 2018, 12 pages.
Exhibit I for Declaration of Carson D. Anderson in Support of Nevro's Administrative Motion to File under Seal Portions of Nevro's Motion for Summary Adjudication and Supporting Documents (Document 347-17) Redacted Version of Document Sought to be Filed under Seal—Rebuttal Expert Report of Richard T. Mihran, Ph.D., *Nevro Corp. vs. Boston Scientific Corporation and Boston Scientific Neuromodulation Corporation*, Case No. 3:16-cv-06830-VC-MEJ, filed Apr. 16, 2018, 24 pages.
Exhibit J for Declaration of Carson D. Anderson in Support of Nevro's Administrative Motion to File under Seal Portions of Nevro's Motion for Summary Adjudication and Supporting Documents (Document 347-19) Redacted Version of Document Sought to be Filed under Seal—Oct. 24, 2016 Boston Scientific Letter to U.S. Food and Drug Administration, *Nevro Corp. vs. Boston Scientific Corporation and Boston Scientific Neuromodulation Corporation*, Case No. 3:16-cv-06830-VC-MEJ, filed Apr. 16, 2018, 5 pages.
Exhibit K for Declaration of Carson D. Anderson in Support of Nevro's Administrative Motion to File under Seal Portions of Nevro's Motion for Summary Adjudication and Supporting Documents (Document 347-21) Redacted Version of Document Sought to be Filed under Seal—Rebuttal Expert Report and Declaration of Daniel Lanovaz dated Feb. 14, 2017, *Nevro Corp. vs. Boston Scientific Corporation and Boston Scientific Neuromodulation Corporation*, Case No. 3:16-cv-06830-VC-MEJ, filed Apr. 16, 2018, 7 pages.
Exhibit L for Declaration of Carson D. Anderson in Support of Nevro's Administrative Motion to File under Seal Portions of Nevro's Motion for Summary Adjudication and Supporting Documents (Document 347-23) Redacted Version of Document Sought to be Filed under Seal—Declaration of Ben Pless in Support of Nevro's Motion of Summary Adjudication dated Apr. 12, 2018, *Nevro Corp. vs. Boston Scientific Corporation and Boston Scientific Neuromodulation Corporation*, Case No. 3:16-cv-06830-VC-MEJ, filed Apr. 16, 2018, 64 pages.
Exhibit L—Updated—for Declaration of Carson D. Anderson in Support of Nevro's Administrative Motion to File under Seal Portions of Nevro's Motion for Summary Adjudication and Supporting Documents (Document 347-24) Updated Redacted Version of Document Sought to be Filed under Seal—Declaration of Ben Pless in Support of Nevro's Motion of Summary Adjudication dated Apr. 12, 2018, *Nevro Corp. vs. Boston Scientific Corporation and Boston Scientific Neuromodulation Corporation*, Case No. 3:16-cv-06830-VC-MEJ, filed Apr. 16, 2018, 64 pages.
Declaration of Rafael Carbunaru in Support of Nevro's Administrative Motion to File under Seal Portions of Nevro's Motion for Summary Adjudication and Supporting Documents (Document 347-25), *Nevro Corp. vs. Boston Scientific Corporation and Boston Scientific Neuromodulation Corporation*, Case No. 3:16-cv-06830-VC-MEJ, filed Apr. 16, 2018, 13 pages.
[Proposed] Order Granting Administrative Motion to File under Seal Portions of Nevro's Administrative Motion to File under Seal Portions of Nevro's Motion for Summary Adjudication and Supporting Documents (ECF No. 341) (Document 347-26), *Nevro Corp. vs. Boston Scientific Corporation and Boston Scientific Neuromodulation Corporation*, Case No. 3:16-cv-06830-VC-MEJ, filed Apr. 16, 2018, 5 pages.
Boston Scientific's Responsive Claim Construction Brief, Opposition to Nevro's Motion for Summary Adjudication and Supporting Documents (Document 466), Updated Redacted Version of ECF No. 357-4, *Nevro Corp. vs. Boston Scientific Corporation and*

(56) References Cited

OTHER PUBLICATIONS

*Boston Scientific Neuromodulation Corporation*, Case No. 3:16-cv-06830-VC-MEJ, filed Jul. 30, 2018, 61 pages.

Expert Report and Declaration of Gene Fridman, Ph.D., regarding Claim Construction (Document 358-1), *Nevro Corp. vs. Boston Scientific Corporation and Boston Scientific Neuromodulation Corporation*, Case No. 3:16-cv-06830-VC-MEJ, filed Apr. 26, 2018, 18 pages.

Rebuttal Expert Report and Declaration of Gene Fridman, Ph.D., regarding Claim Construction (Document 358-2), *Nevro Corp. vs. Boston Scientific Corporation and Boston Scientific Neuromodulation Corporation*, Case No. 3:16-cv-06830-VC-MEJ, filed Apr. 26, 2018, 11 pages.

Declaration of Richard T. Mihran, Ph.D., regarding Claim Construction Brief (Document 358-3), *Nevro Corp. vs. Boston Scientific Corporation and Boston Scientific Neuromodulation Corporation*, Case No. 3:16-cv-06830-VC-MEJ, filed Apr. 26, 2018, 2 pages.

Exhibit A for Declaration of Richard T. Mihran, Ph.D., regarding Claim Construction Brief (Document 358-4), Expert Report of Richard T. Mihran, Ph.D. regarding Invalidity of U.S. Pat. No. 8,712,533; U.S. Pat. No. 9,327,125; U.S. Pat. No. 8,359,102; U.S. Pat. No. 9,480,842; U.S. Pat. No. 9,333,357; U.S. Pat. No. 8,792,988; and U.S. Pat. No. 8,768,472, *Nevro Corp. vs. Boston Scientific Corporation and Boston Scientific Neuromodulation Corporation*, Case No. 3:16-cv-06830-VC-MEJ, filed Apr. 26, 2018, 129 pages.

Exhibit B Declaration of Richard T. Mihran, Ph.D., regarding Claim Construction Brief (Document 358-5), Redacted Version of Document Sought to be Filed under Seal—Rebuttal Expert Report of Richard T. Mihran, Ph.D., *Nevro Corp. vs. Boston Scientific Corporation and Boston Scientific Neuromodulation Corporation*, Case No. 3:16-cv-06830-VC-MEJ, filed Apr. 26, 2018, 79 pages.

Declaration of Clara W. Wang in Support of Boston Scientific's Responsive regarding Claim Construction Brief; Opposition to Nevro's Motion for Summary Judgement and Opening Motion for Summary Judgement (Document 358-6), *Nevro Corp. vs. Boston Scientific Corporation and Boston Scientific Neuromodulation Corporation*, Case No. 3:16-cv-06830-VC-MEJ, filed Apr. 26, 2018, 8 pages.

Exhibit 1 for Declaration of Clara W. Wang in Support of Boston Scientific's Responsive regarding Claim Construction Brief; Opposition to Nevro's Motion for Summary Judgement and Opening Motion for Summary Judgement (Document 358-7), Sep. 2005 Email between K. Bradley and M. Moffitt, *Nevro Corp. vs. Boston Scientific Corporation and Boston Scientific Neuromodulation Corporation*, Case No. 3:16-cv-06830-VC-MEJ, filed Apr. 26, 2018, 2 pages.

Exhibit 2 for Declaration of Clara W. Wang in Support of Boston Scientific's Responsive regarding Claim Construction Brief; Opposition to Nevro's Motion for Summary Judgement and Opening Motion for Summary Judgement (Document 358-8), Filed under Seal—Document NEVRO_BSXCA0165810-52, *Nevro Corp. vs. Boston Scientific Corporation and Boston Scientific Neuromodulation Corporation*, Case No. 3:16-cv-06830-VC-MEJ, filed Apr. 26, 2018, 1 page.

Exhibit 3 for Declaration of Clara W. Wang in Support of Boston Scientific's Responsive regarding Claim Construction Brief; Opposition to Nevro's Motion for Summary Judgement and Opening Motion for Summary Judgement (Document 358-9), Filed under Seal—Document NEVRO_BSXCA0389050-100, *Nevro Corp. vs. Boston Scientific Corporation and Boston Scientific Neuromodulation Corporation*, Case No. 3:16-cv-06830-VC-MEJ, filed Apr. 26, 2018, 1 page.

Exhibit 4 for Declaration of Clara W. Wang in Support of Boston Scientific's Responsive regarding Claim Construction Brief; Opposition to Nevro's Motion for Summary Judgement and Opening Motion for Summary Judgement (Document 358-10), Summary of Safety and Effectiveness Data (SSED), *Nevro Corp. vs. Boston Scientific Corporation and Boston Scientific Neuromodulation Corporation*, Case No. 3:16-cv-06830-VC-MEJ, filed Apr. 26, 2018, 57 pages.

Exhibit 5 for Declaration of Clara W. Wang in Support of Boston Scientific's Responsive regarding Claim Construction Brief; Opposition to Nevro's Motion for Summary Judgement and Opening Motion for Summary Judgement (Document 358-11), Article by Andres et al., *Nevro Corp. vs. Boston Scientific Corporation and Boston Scientific Neuromodulation Corporation*, Case No. 3:16-cv-06830-VC-MEJ, filed Apr. 26, 2018, 22 pages.

Exhibit 6 for Declaration of Clara W. Wang in Support of Boston Scientific's Responsive regarding Claim Construction Brief; Opposition to Nevro's Motion for Summary Judgement and Opening Motion for Summary Judgement (Document 358-12), Article by Thomson et al., *Nevro Corp. vs. Boston Scientific Corporation and Boston Scientific Neuromodulation Corporation*, Case No. 3:16-cv-06830-VC-MEJ, filed Apr. 26, 2018, 11 pages.

Exhibit 7 for Declaration of Clara W. Wang in Support of Boston Scientific's Responsive regarding Claim Construction Brief; Opposition to Nevro's Motion for Summary Judgement and Opening Motion for Summary Judgement (Document 358-13), Filed under Seal—Document labeled NEVRO_BSXCA0053540-89, *Nevro Corp. vs. Boston Scientific Corporation and Boston Scientific Neuromodulation Corporation*, Case No. 3:16-cv-06830-VC-MEJ, filed Apr. 26, 2018, 1 page.

Exhibit 8 for Declaration of Clara W. Wang in Support of Boston Scientific's Responsive regarding Claim Construction Brief; Opposition to Nevro's Motion for Summary Judgement and Opening Motion for Summary Judgement (Document 358-14), Filed under Seal—Document labeled NEVRO_BSXCA0055766-70, *Nevro Corp. vs. Boston Scientific Corporation and Boston Scientific Neuromodulation Corporation*, Case No. 3:16-cv-06830-VC-MEJ, filed Apr. 26, 2018, 1 page.

Exhibit 9 for Declaration of Clara W. Wang in Support of Boston Scientific's Responsive regarding Claim Construction Brief; Opposition to Nevro's Motion for Summary Judgement and Opening Motion for Summary Judgement (Document 358-15), Filed under Seal—Document labeled NEVRO_BSXCA0049348-69, *Nevro Corp. vs. Boston Scientific Corporation and Boston Scientific Neuromodulation Corporation*, Case No. 3:16-cv-06830-VC-MEJ, filed Apr. 26, 2018, 1 page.

Exhibit 10 for Declaration of Clara W. Wang in Support of Boston Scientific's Responsive regarding Claim Construction Brief; Opposition to Nevro's Motion for Summary Judgement and Opening Motion for Summary Judgement (Document 358-16), Videotaped Deposition of Rafael Carbunaru, Ph.D., taken on Nov. 15, 2017, *Nevro Corp. vs. Boston Scientific Corporation and Boston Scientific Neuromodulation Corporation*, Case No. 3:16-cv-06830-VC-MEJ, filed Apr. 26, 2018, 9 pages.

Exhibit 11 for Declaration of Clara W. Wang in Support of Boston Scientific's Responsive regarding Claim Construction Brief; Opposition to Nevro's Motion for Summary Judgement (Document 358-17), Redacted Version of Document Sought to be Filed under Sealed—Videotaped Deposition of Jim Cassidy, taken on Nov. 29, 2017, *Nevro Corp. vs. Boston Scientific Corporation and Boston Scientific Neuromodulation Corporation*, Case No. 3:16-cv-06830-VC-MEJ, filed Apr. 26, 2018, 9 pages.

Exhibit 12 for Declaration of Clara W. Wang in Support of Boston Scientific's Responsive regarding Claim Construction Brief; Opposition to Nevro's Motion for Summary Judgement and Opening Motion for Summary Judgement (Document 467), Filed under Sealed—Videotaped Deposition of Kaoru Lee Adair, taken on Nov. 17, 2017, *Nevro Corp. vs. Boston Scientific Corporation and Boston Scientific Neuromodulation Corporation*, Case No. 3:16-cv-06830-VC-MEJ, filed Apr. 26, 2018, 10 pages.

Exhibit 13 for Declaration of Clara W. Wang in Support of Boston Scientific's Responsive regarding Claim Construction Brief; Opposition to Nevro's Motion for Summary Judgement and Opening Motion for Summary Judgement (Document 358-19), Redacted Version of Document Sought to be Filed under Seal—Videotaped Deposition of Jim Cassidy, taken on Nov. 30, 2017, *Nevro Corp. vs. Boston Scientific Corporation and Boston Scientific Neuromodulation Corporation*, Case No. 3:16-cv-06830-VC-MEJ, filed Apr. 26, 2018, 10 pages.

(56) References Cited

OTHER PUBLICATIONS

Exhibit 14 for Declaration of Clara W. Wang in Support of Boston Scientific's Responsive regarding Claim Construction Brief; Opposition to Nevro's Motion for Summary Judgement and Opening Motion for Summary Judgement (Document 358-20), Apr. 2018 Email between K. Carter and MoFo-NevroBSX, taken on Nov. 30, 2017, *Nevro Corp.* vs. *Boston Scientific Corporation and Boston Scientific Neuromodulation Corporation*, Case No. 3:16-cv-06830-VC-MEJ, filed Apr. 26, 2018, 2 pages.
Exhibit 15 for Declaration of Clara W. Wang in Support of Boston Scientific's Responsive regarding Claim Construction Brief; Opposition to Nevro's Motion for Summary Judgement and Opening Motion for Summary Judgement (Document 358-21), Boston Scientific Advancing Science for Life—Technical Sales Training, *Nevro Corp.* vs. *Boston Scientific Corporation and Boston Scientific Neuromodulation Corporation*, Case No. 3:16-cv-06830-VC-MEJ, filed Apr. 26, 2018, 3 pages.
Exhibit 16 for Declaration of Clara W. Wang in Support of Boston Scientific's Responsive regarding Claim Construction Brief; Opposition to Nevro's Motion for Summary Judgement and Opening Motion for Summary Judgement (Document 358-22), Product Specification for Ninja System, *Nevro Corp.* vs. *Boston Scientific Corporation and Boston Scientific Neuromodulation Corporation*, Case No. 3:16-cv-06830-VC-MEJ, filed Apr. 26, 2018, 3 pages.
Exhibit 17 for Declaration of Clara W. Wang in Support of Boston Scientific's Responsive regarding Claim Construction Brief; Opposition to Nevro's Motion for Summary Judgement and Opening Motion for Summary Judgement (Document 358-23), Deposition of Ben Pless, taken on Apr. 10, 2018, *Nevro Corp.* vs. *Boston Scientific Corporation and Boston Scientific Neuromodulation Corporation*, Case No. 3:16-cv-06830-VC-MEJ, filed Apr. 26, 2018, 3 pages.
Exhibit 18 for Declaration of Clara W. Wang in Support of Boston Scientific's Responsive regarding Claim Construction Brief; Opposition to Nevro's Motion for Summary Judgement and Opening Motion for Summary Judgement (Document 358-24), Merriam-Webster's Collegiate Dictionary, *Nevro Corp.* vs. *Boston Scientific Corporation and Boston Scientific Neuromodulation Corporation*, Case No. 3:16-cv-06830-VC-MEJ, filed Apr. 26, 2018, 5 pages.
Exhibit 19 for Declaration of Clara W. Wang in Support of Boston Scientific's Responsive regarding Claim Construction Brief; Opposition to Nevro's Motion for Summary Judgement and Opening Motion for Summary Judgement (Document 358-25), Merriam-Webster's Collegiate Dictionary, *Nevro Corp.* vs. *Boston Scientific Corporation and Boston Scientific Neuromodulation Corporation*, Case No. 3:16-cv-06830-VC-MEJ, filed Apr. 26, 2018, 5 pages.
Exhibit 20 for Declaration of Clara W. Wang in Support of Boston Scientific's Responsive regarding Claim Construction Brief; Opposition to Nevro's Motion for Summary Judgement and Opening Motion for Summary Judgement (Document 358-26), Concise Oxford Dictionary, *Nevro Corp.* vs. *Boston Scientific Corporation and Boston Scientific Neuromodulation Corporation*, Case No. 3:16-cv-06830-VC-MEJ, filed Apr. 26, 2018, 5 pages.
Exhibit 21 for Declaration of Clara W. Wang in Support of Boston Scientific's Responsive regarding Claim Construction Brief; Opposition to Nevro's Motion for Summary Judgement and Opening Motion for Summary Judgement (Document 358-27), Final Office Action for U.S. Appl. No. 15/134,285, issued Nov. 28, 2017, *Nevro Corp.* vs. *Boston Scientific Corporation and Boston Scientific Neuromodulation Corporation*, Case No. 3:16-cv-06830-VC-MEJ, filed Apr. 26, 2018, 22 pages.
Exhibit 22 for Declaration of Clara W. Wang in Support of Boston Scientific's Responsive regarding Claim Construction Brief; Opposition to Nevro's Motion for Summary Judgement and Opening Motion for Summary Judgement (Document 358-28), U.S. Pat. No. 8,355,797 by Caparso et al., *Nevro Corp.* vs. *Boston Scientific Corporation and Boston Scientific Neuromodulation Corporation*, Case No. 3:16-cv-06830-VC-MEJ, filed Apr. 26, 2018, 21 pages.
Exhibit 23 for Declaration of Clara W. Wang in Support of Boston Scientific's Responsive regarding Claim Construction Brief; Opposition to Nevro's Motion for Summary Judgement and Opening Motion for Summary Judgement (Document 358-29), Redacted Version of the Document Sought to be Filed under Seal—Deposition of Jon Parker dated Nov. 16, 2017, *Nevro Corp.* vs. *Boston Scientific Corporation and Boston Scientific Neuromodulation Corporation*, Case No. 3:16-cv-06830-VC-MEJ, filed Apr. 26, 2018, 12 pages.
Exhibit 24 for Declaration of Clara W. Wang in Support of Boston Scientific's Responsive regarding Claim Construction Brief; Opposition to Nevro's Motion for Summary Judgement and Opening Motion for Summary Judgement (Document 358-30), Redacted Version of the Document Sought to be Filed under Seal—Corrected Rebuttal Expert Report of Ben Plesss regarding Validity dated Mar. 5, 2018, *Nevro Corp.* vs. *Boston Scientific Corporation and Boston Scientific Neuromodulation Corporation*, Case No. 3:16-cv-06830-VC-MEJ, filed Apr. 26, 2018, 55 pages.
Exhibit 25 for Declaration of Clara W. Wang in Support of Boston Scientific's Responsive regarding Claim Construction Brief; Opposition to Nevro's Motion for Summary Judgement and Opening Motion for Summary Judgement (Document 358-31), Deposition of Dr. Gene Fridman dated Mar. 7, 2018, *Nevro Corp.* vs. *Boston Scientific Corporation and Boston Scientific Neuromodulation Corporation*, Case No. 3:16-cv-06830-VC-MEJ, filed Apr. 26, 2018, 14 pages.
Exhibit 26 for Declaration of Clara W. Wang in Support of Boston Scientific's Responsive regarding Claim Construction Brief; Opposition to Nevro's Motion for Summary Judgement and Opening Motion for Summary Judgement (Document 358-32), Redacted Version of Document Sought to be Filed under Seal—Opening Expert Report of Ben Pless regarding Infringement dated Jan. 18, 2018, *Nevro Corp.* vs. *Boston Scientific Corporation and Boston Scientific Neuromodulation Corporation*, Case No. 3:16-cv-06830-VC-MEJ, filed Apr. 26, 2018, 23 pages.
Exhibit 27 for Declaration of Clara W. Wang in Support of Boston Scientific's Responsive regarding Claim Construction Brief; Opposition to Nevro's Motion for Summary Judgement and Opening Motion for Summary Judgement (Document 358-33), U.S. Patent Application Publication No. 2017/0050021 to Cosman Sr., *Nevro Corp.* vs. *Boston Scientific Corporation and Boston Scientific Neuromodulation Corporation*, Case No. 3:16-cv-06830-VC-MEJ, filed Apr. 26, 2018, 32 pages.
Exhibit 28 for Declaration of Clara W. Wang in Support of Boston Scientific's Responsive regarding Claim Construction Brief; Opposition to Nevro's Motion for Summary Judgement and Opening Motion for Summary Judgement (Document 358-34), Expert Report of William S. Rosenberg, MD, Faans, dated Jan. 18, 2018, *Nevro Corp.* vs. *Boston Scientific Corporation and Boston Scientific Neuromodulation Corporation*, Case No. 3:16-cv-06830-VC-MEJ, filed Apr. 26, 2018, 4 pages.
Exhibit 29 for Declaration of Clara W. Wang in Support of Boston Scientific's Responsive regarding Claim Construction Brief; Opposition to Nevro's Motion for Summary Judgement and Opening Motion for Summary Judgement (Document 358-35), Declaration of David Caraway, M.D. Ph.D., dated Feb. 16, 2016, *Nevro Corp.* vs. *Boston Scientific Corporation and Boston Scientific Neuromodulation Corporation*, Case No. 3:16-cv-06830-VC-MEJ, filed Apr. 26, 2018, 8 pages.
Exhibit 30 for Declaration of Clara W. Wang in Support of Boston Scientific's Responsive regarding Claim Construction Brief; Opposition to Nevro's Motion for Summary Judgement and Opening Motion for Summary Judgement (Document 358-36), Filed under Seal—Document NEVRO_BSXCA0073295-300, *Nevro Corp.* vs. *Boston Scientific Corporation and Boston Scientific Neuromodulation Corporation*, Case No. 3:16-cv-06830-VC-MEJ, filed Apr. 26, 2018, 1 page.
Exhibit 31 for Declaration of Clara W. Wang in Support of Boston Scientific's Responsive regarding Claim Construction Brief; Opposition to Nevro's Motion for Summary Judgement and Opening Motion for Summary Judgement (Document 358-37), Article by Alexander J.R. Macdonald et al., *Nevro Corp.* vs. *Boston Scientific Corporation and Boston Scientific Neuromodulation Corporation*, Case No. 3:16-cv-06830-VC-MEJ, filed Apr. 26, 2018, 10 pages.
Exhibit 32 for Declaration of Clara W. Wang in Support of Boston Scientific's Responsive regarding Claim Construction Brief; Oppo-

(56) References Cited

OTHER PUBLICATIONS sition to Nevro's Motion for Summary Judgement and Opening Motion for Summary Judgement (Document 358-38), U.S. Pat. No. 5,776,170 to MacDonald et al., *Nevro Corp. vs. Boston Scientific Corporation and Boston Scientific Neuromodulation Corporation*, Case No. 3:16-cv-06830-VC-MEJ, filed Apr. 26, 2018, 12 pages.
Exhibit 33 for Declaration of Clara W. Wang in Support of Boston Scientific's Responsive regarding Claim Construction Brief; Opposition to Nevro's Motion for Summary Judgement and Opening Motion for Summary Judgement (Document 358-39), File History for U.S. Appl. No. 14/525,134, issued Mar. 12, 2015, *Nevro Corp. vs. Boston Scientific Corporation and Boston Scientific Neuromodulation Corporation*, Case No. 3:16-cv-06830-VC-MEJ, filed Apr. 26, 2018, 34 pages.
Exhibit 34 for Declaration of Clara W. Wang in Support of Boston Scientific's Responsive regarding Claim Construction Brief; Opposition to Nevro's Motion for Summary Judgement and Opening Motion for Summary Judgement (Document 358-40), Filed under Seal—Document NEVRO_BSXCA0108347-8, *Nevro Corp. vs. Boston Scientific Corporation and Boston Scientific Neuromodulation Corporation*, Case No. 3:16-cv-06830-VC-MEJ, filed Apr. 26, 2018, 1 page.
Exhibit 35 for Declaration of Clara W. Wang in Support of Boston Scientific's Responsive regarding Claim Construction Brief; Opposition to Nevro's Motion for Summary Judgement and Opening Motion for Summary Judgement (Document 358-41), Non-Final Office Action for U.S. Appl. No. 14/503,259, issued Dec. 3, 2015, *Nevro Corp. vs. Boston Scientific Corporation and Boston Scientific Neuromodulation Corporation*, Case No. 3:16-cv-06830-VC-MEJ, filed Apr. 26, 2018, 11 pages.
Exhibit 36 for Declaration of Clara W. Wang in Support of Boston Scientific's Responsive regarding Claim Construction Brief; Opposition to Nevro's Motion for Summary Judgement and Opening Motion for Summary Judgement (Document 358-42), Documents from File History for U.S. Appl. No. 14/261,369, *Nevro Corp. vs. Boston Scientific Corporation and Boston Scientific Neuromodulation Corporation*, Case No. 3:16-cv-06830-VC-MEJ, filed Apr. 26, 2018, 59 pages.
Exhibit 37 for Declaration of Clara W. Wang in Support of Boston Scientific's Responsive regarding Claim Construction Brief; Opposition to Nevro's Motion for Summary Judgement and Opening Motion for Summary Judgement (Document 358-43), Final Office Action for U.S. Appl. No. 15/134,285, issued Nov. 28, 2017, *Nevro Corp. vs. Boston Scientific Corporation and Boston Scientific Neuromodulation Corporation*, Case No. 3:16-cv-06830-VC-MEJ, filed Apr. 26, 2018, 22 pages.
Exhibit 38 for Declaration of Clara W. Wang in Support of Boston Scientific's Responsive regarding Claim Construction Brief; Opposition to Nevro's Motion for Summary Judgement and Opening Motion for Summary Judgement (Document 358-44), U.S. National Library of Medicine—ClinicalTrials.gov, *Nevro Corp. vs. Boston Scientific Corporation and Boston Scientific Neuromodulation Corporation*, Case No. 3:16-cv-06830-VC-MEJ, filed Apr. 26, 2018, 6 pages.
Exhibit 39 for Declaration of Clara W. Wang in Support of Boston Scientific's Responsive regarding Claim Construction Brief; Opposition to Nevro's Motion for Summary Judgement and Opening Motion for Summary Judgement (Document 358-45), Redacted Version of Document Sought to be Filed under Seal—Jan. 23, 2014 Correspondence to Boston Scientific Corporation, *Nevro Corp. vs. Boston Scientific Corporation and Boston Scientific Neuromodulation Corporation*, Case No. 3:16-cv-06830-VC-MEJ, filed Apr. 26, 2018, 10 pages.
Exhibit 40 for Declaration of Clara W. Wang in Support of Boston Scientific's Responsive regarding Claim Construction Brief; Opposition to Nevro's Motion for Summary Judgement and Opening Motion for Summary Judgement (Document 358-46), Redacted Version of Document Sought to be Filed under Seal—Nov. 23, 2016 Email and Correspondence to Kaoru Adair, *Nevro Corp. vs. Boston Scientific Corporation and Boston Scientific Neuromodulation Corporation*, Case No. 3:16-cv-06830-VC-MEJ, filed Apr. 26, 2018, 8 pages.
Exhibit 41 for Declaration of Clara W. Wang in Support of Boston Scientific's Responsive regarding Claim Construction Brief; Opposition to Nevro's Motion for Summary Judgement and Opening Motion for Summary Judgement (Document 358-47), Boston Scientific—Investigational Device Exemption (IDE) Application, submission date Feb. 21, 2013, *Nevro Corp. vs. Boston Scientific Corporation and Boston Scientific Neuromodulation Corporation*, Case No. 3:16-cv-06830-VC-MEJ, filed Apr. 26, 2018, 5 pages.
Exhibit 42 for Declaration of Clara W. Wang in Support of Boston Scientific's Responsive regarding Claim Construction Brief; Opposition to Nevro's Motion for Summary Judgement and Opening Motion for Summary Judgement (Document 358-48), Redacted Version of Document Sought to be Filed under Seal—Boston Scientific—A Randomized Controlled Study to Evaluate the Safety and Effectiveness of the Precision Spinal Cord Stimulator System Adapted for High-Rate Spinal Cord Stimulation, *Nevro Corp. vs. Boston Scientific Corporation and Boston Scientific Neuromodulation Corporation*, Case No. 3:16-cv-06830-VC-MEJ, filed Apr. 26, 2018, 5 pages.
Exhibit 43 for Declaration of Clara W. Wang in Support of Boston Scientific's Responsive regarding Claim Construction Brief; Opposition to Nevro's Motion for Summary Judgement and Opening Motion for Summary Judgement (Document 358-49), World Medical Association—WMA Declaration of Helsinki—Ethical Principles for Medical Research Involving Human Subjects, *Nevro Corp. vs. Boston Scientific Corporation and Boston Scientific Neuromodulation Corporation*, Case No. 3:16-cv-06830-VC-MEJ, filed Apr. 26, 2018, 3 pages.
Exhibit 44 for Declaration of Clara W. Wang in Support of Boston Scientific's Responsive regarding Claim Construction Brief; Opposition to Nevro's Motion for Summary Judgement and Opening Motion for Summary Judgement (Document 358-50), U.S. Patent Application Publication No. 2007/0073354 to Knudson et al., *Nevro Corp. vs. Boston Scientific Corporation and Boston Scientific Neuromodulation Corporation*, Case No. 3:16-cv-06830-VC-MEJ, filed Apr. 26, 2018, 15 pages.
Exhibit 45 for Declaration of Clara W. Wang in Support of Boston Scientific's Responsive regarding Claim Construction Brief; Opposition to Nevro's Motion for Summary Judgement and Opening Motion for Summary Judgement (Document 358-51), U.S. Patent Application Publication No. 2007/0060954 to Cameron et al., *Nevro Corp. vs. Boston Scientific Corporation and Boston Scientific Neuromodulation Corporation*, Case No. 3:16-cv-06830-VC-MEJ, filed Apr. 26, 2018, 21 pages.
Exhibit 46 for Declaration of Clara W. Wang in Support of Boston Scientific's Responsive regarding Claim Construction Brief; Opposition to Nevro's Motion for Summary Judgement and Opening Motion for Summary Judgement (Document 358-52), Documents from File History for U.S. Appl. No. 12/765,747, *Nevro Corp. vs. Boston Scientific Corporation and Boston Scientific Neuromodulation Corporation*, Case No. 3:16-cv-06830-VC-MEJ, filed Apr. 26, 2018, 57 pages.
Exhibit 47 for Declaration of Clara W. Wang in Support of Boston Scientific's Responsive regarding Claim Construction Brief; Opposition to Nevro's Motion for Summary Judgement and Opening Motion for Summary Judgement (Document 358-53), Response to Final Office Action for U.S. Appl. No. 14/292,671, filed Jan. 17, 2017, *Nevro Corp. vs. Boston Scientific Corporation and Boston Scientific Neuromodulation Corporation*, Case No. 3:16-cv-06830-VC-MEJ, filed Apr. 26, 2018, 12 pages.
Exhibit 48 for Declaration of Clara W. Wang in Support of Boston Scientific's Responsive regarding Claim Construction Brief; Opposition to Nevro's Motion for Summary Judgement and Opening Motion for Summary Judgement (Document 358-54), Response to Non-Final Office Action for U.S. Appl. No. 14/503,259, filed Mar. 16, 2015, *Nevro Corp. vs. Boston Scientific Corporation and Boston Scientific Neuromodulation Corporation*, Case No. 3:16-cv-06830-VC-MEJ, filed Apr. 26, 2018, 30 pages.
Exhibit 49 for Declaration of Clara W. Wang in Support of Boston Scientific's Responsive regarding Claim Construction Brief; Oppo-

(56) References Cited

OTHER PUBLICATIONS sition to Nevro's Motion for Summary Judgement and Opening Motion for Summary Judgement (Document 358-55), Redacted Version of Document Sought to be Filed under Seal—Deposition of Konstantinos Alataris dated Nov. 14, 2017, *Nevro Corp. vs. Boston Scientific Corporation and Boston Scientific Neuromodulation Corporation*, Case No. 3:16-cv-06830-VC-MEJ, filed Apr. 26, 2018, 21 pages.

Exhibit 50 for Declaration of Clara W. Wang in Support of Boston Scientific's Responsive regarding Claim Construction Brief; Opposition to Nevro's Motion for Summary Judgement and Opening Motion for Summary Judgement (Document 358-56), Chart for Asserted Claims by Limitation Category, *Nevro Corp. vs. Boston Scientific Corporation and Boston Scientific Neuromodulation Corporation*, Case No. 3:16-cv-06830-VC-MEJ, filed Apr. 26, 2018, 12 pages.

Exhibit 51 for Declaration of Clara W. Wang in Support of Boston Scientific's Responsive regarding Claim Construction Brief; Opposition to Nevro's Motion for Summary Judgement and Opening Motion for Summary Judgement (Document 358-57), U.S. Patent Application Publication No. 2009/0204173 to Fang et al., *Nevro Corp. vs. Boston Scientific Corporation and Boston Scientific Neuromodulation Corporation*, Case No. 3:16-cv-06830-VC-MEJ, filed Apr. 26, 2018, 33 pages.

Exhibit 52 for Declaration of Clara W. Wang in Support of Boston Scientific's Responsive regarding Claim Construction Brief; Opposition to Nevro's Motion for Summary Judgement and Opening Motion for Summary Judgement (Document 358-58), Applicant-Initiated Interview Summary for U.S. Appl. No. 14/037,262, issued Feb. 25, 2014, *Nevro Corp. vs. Boston Scientific Corporation and Boston Scientific Neuromodulation Corporation*, Case No. 3:16-cv-06830-VC-MEJ, filed Apr. 26, 2018, 5 pages.

Exhibit 53 for Declaration of Clara W. Wang in Support of Boston Scientific's Responsive regarding Claim Construction Brief; Opposition to Nevro's Motion for Summary Judgement and Opening Motion for Summary Judgement (Document 358-59), Redacted Version of Document Sought to be Filed under Seal—Videotaped Deposition of Zi-Ping Fang dated Nov. 2, 2017, *Nevro Corp. vs. Boston Scientific Corporation and Boston Scientific Neuromodulation Corporation*, Case No. 3:16-cv-06830-VC-MEJ, filed Apr. 26, 2018, 16 pages.

Exhibit 54 for Declaration of Clara W. Wang in Support of Boston Scientific's Responsive regarding Claim Construction Brief; Opposition to Nevro's Motion for Summary Judgement and Opening Motion for Summary Judgement (Document 358-60), Handwritten Figure, *Nevro Corp. vs. Boston Scientific Corporation and Boston Scientific Neuromodulation Corporation*, Case No. 3:16-cv-06830-VC-MEJ, filed Apr. 26, 2018, 3 pages.

Exhibit 55 for Declaration of Clara W. Wang in Support of Boston Scientific's Responsive regarding Claim Construction Brief; Opposition to Nevro's Motion for Summary Judgement and Opening Motion for Summary Judgement (Document 358-61), Handwritten Figure, *Nevro Corp. vs. Boston Scientific Corporation and Boston Scientific Neuromodulation Corporation*, Case No. 3:16-cv-06830-VC-MEJ, filed Apr. 26, 2018, 3 pages.

Exhibit 56 for Declaration of Clara W. Wang in Support of Boston Scientific's Responsive regarding Claim Construction Brief; Opposition to Nevro's Motion for Summary Judgement and Opening Motion for Summary Judgement (Document 358-62), Declaration of Rafael Cabunaru in Support of Boston Scientific's Invalidity Contentions, *Nevro Corp. vs. Boston Scientific Corporation and Boston Scientific Neuromodulation Corporation*, Case No. 3:16-cv-06830-VC-MEJ, filed Apr. 26, 2018, 132 pages.

Exhibit 57 for Declaration of Clara W. Wang in Support of Boston Scientific's Responsive regarding Claim Construction Brief; Opposition to Nevro's Motion for Summary Judgement and Opening Motion for Summary Judgement (Document 358-63), Deposition of David Caraway, M.D., Ph.D., dated Nov. 14, 2017, *Nevro Corp. vs. Boston Scientific Corporation and Boston Scientific Neuromodulation Corporation*, Case No. 3:16-cv-06830-VC-MEJ, filed Apr. 26, 2018, 15 pages.

Exhibit 58 for Declaration of Clara W. Wang in Support of Boston Scientific's Responsive regarding Claim Construction Brief; Opposition to Nevro's Motion for Summary Judgement and Opening Motion for Summary Judgement (Document 358-64), Filed under Seal—Document NEVRO_BSXCA0209790-812, *Nevro Corp. vs. Boston Scientific Corporation and Boston Scientific Neuromodulation Corporation*, Case No. 3:16-cv-06830-VC-MEJ, filed Apr. 26, 2018, 1 page.

Exhibit 59 for Declaration of Clara W. Wang in Support of Boston Scientific's Responsive regarding Claim Construction Brief; Opposition to Nevro's Motion for Summary Judgement and Opening Motion for Summary Judgement (Document 358-65), Videotaped Deposition of Dr. James North taken on Nov. 18, 2017, *Nevro Corp. vs. Boston Scientific Corporation and Boston Scientific Neuromodulation Corporation*, Case No. 3:16-cv-06830-VC-MEJ, filed Apr. 26, 2018, 11 pages.

Exhibit 60 for Declaration of Clara W. Wang in Support of Boston Scientific's Responsive regarding Claim Construction Brief; Opposition to Nevro's Motion for Summary Judgement and Opening Motion for Summary Judgement (Document 358-66), Videotaped Deposition of Robert Nathan taken on Nov. 15, 2017, *Nevro Corp. vs. Boston Scientific Corporation and Boston Scientific Neuromodulation Corporation*, Case No. 3:16-cv-06830-VC-MEJ, filed Apr. 26, 2018, 11 pages.

Exhibit 61 for Declaration of Clara W. Wang in Support of Boston Scientific's Responsive regarding Claim Construction Brief; Opposition to Nevro's Motion for Summary Judgement and Opening Motion for Summary Judgement (Document 358-67), Case Report by Yearwood et al., *Nevro Corp. vs. Boston Scientific Corporation and Boston Scientific Neuromodulation Corporation*, Case No. 3:16-cv-06830-VC-MEJ, filed Apr. 26, 2018, 3 pages.

Exhibit 62 for Declaration of Clara W. Wang in Support of Boston Scientific's Responsive regarding Claim Construction Brief; Opposition to Nevro's Motion for Summary Judgement and Opening Motion for Summary Judgement (Document 358-68), Videotaped Deposition of Dr. William S. Rosenberg dated Mar. 21, 2018, *Nevro Corp. vs. Boston Scientific Corporation and Boston Scientific Neuromodulation Corporation*, Case No. 3:16-cv-06830-VC-MEJ, filed Apr. 26, 2018, 11 pages.

Exhibit 63 for Declaration of Clara W. Wang in Support of Boston Scientific's Responsive regarding Claim Construction Brief; Opposition to Nevro's Motion for Summary Judgement and Opening Motion for Summary Judgement (Document 358-69), Document by Yearwood et al., *Nevro Corp. vs. Boston Scientific Corporation and Boston Scientific Neuromodulation Corporation*, Case No. 3:16-cv-06830-VC-MEJ, filed Apr. 26, 2018, 8 pages.

Exhibit 64 for Declaration of Clara W. Wang in Support of Boston Scientific's Responsive regarding Claim Construction Brief; Opposition to Nevro's Motion for Summary Judgement and Opening Motion for Summary Judgement (Document 358-70), Redacted Version of Document Sought to be Filed under Seal—Videotaped Deposition of James Thacker (vol. I) dated Dec. 7, 2017, *Nevro Corp. vs. Boston Scientific Corporation and Boston Scientific Neuromodulation Corporation*, Case No. 3:16-cv-06830-VC-MEJ, filed Apr. 26, 2018, 35 pages.

Exhibit 65 for Declaration of Clara W. Wang in Support of Boston Scientific's Responsive regarding Claim Construction Brief; Opposition to Nevro's Motion for Summary Judgement and Opening Motion for Summary Judgement (Document 358-71), Filed under Seal—Document NEVRO_BSXCA0118164-203, *Nevro Corp. vs. Boston Scientific Corporation and Boston Scientific Neuromodulation Corporation*, Case No. 3:16-cv-06830-VC-MEJ, filed Apr. 26, 2018, 1 page.

Exhibit 66 for Declaration of Clara W. Wang in Support of Boston Scientific's Responsive regarding Claim Construction Brief; Opposition to Nevro's Motion for Summary Judgement and Opening Motion for Summary Judgement (Document 358-72), Videotaped Deposition of Kerry Bradley dated Nov. 8, 2017, *Nevro Corp. vs.*

(56) References Cited

OTHER PUBLICATIONS

*Boston Scientific Corporation and Boston Scientific Neuromodulation Corporation*, Case No. 3:16-cv-06830-VC-MEJ, filed Apr. 26, 2018, 10 pages.
Exhibit 67 for Declaration of Clara W. Wang in Support of Boston Scientific's Responsive regarding Claim Construction Brief; Opposition to Nevro's Motion for Summary Judgement and Opening Motion for Summary Judgement (Document 358-73), Response to Final Office Action for U.S. Appl. No. 12/765,685, filed Sep. 19, 2013, *Nevro Corp. vs. Boston Scientific Corporation and Boston Scientific Neuromodulation Corporation*, Case No. 3:16-cv-06830-VC-MEJ, filed Apr. 26, 2018, 15 pages.
Exhibit 68 for Declaration of Clara W. Wang in Support of Boston Scientific's Responsive regarding Claim Construction Brief; Opposition to Nevro's Motion for Summary Judgement and Opening Motion for Summary Judgement (Document 358-74), Response to Non-Final Office Action for U.S. Appl. No. 13/830,992, filed Feb. 24, 2014, *Nevro Corp. vs. Boston Scientific Corporation and Boston Scientific Neuromodulation Corporation*, Case No. 3:16-cv-06830-VC-MEJ, filed Apr. 26, 2018, 15 pages.
Rebuttal Expert Report and Declaration of Daniel Lanovaz (Document 359), *Nevro Corp. vs. Boston Scientific Corporation and Boston Scientific Neuromodulation Corporation*, Case No. 3:16-cv-06830-VC-MEJ, filed Apr. 26, 2018, 10 pages.
Nevro's Reply in Support of its Motion for Summary Adjudication and Opposition to BSC's Motion for Summary Judgement (Document 468), Updated Redacted Version of ECF No. 382-2, *Nevro Corp. vs. Boston Scientific Corporation and Boston Scientific Neuromodulation Corporation*, Case No. 3:16-cv-06830-VC-MEJ, filed Jul. 30, 2018, 40 pages.
Declaration of Joshua Goshorn in Support of Nevro's Reply in Support of Motion for Summary Adjudication and Opposition to BSC's Motion for Summary Judgement (Document 375), *Nevro Corp. vs. Boston Scientific Corporation and Boston Scientific Neuromodulation Corporation*, Case No. 3:16-cv-06830-VC-MEJ, filed May 10, 2018, 2 pages.
Exhibit A for Declaration of Joshua Goshorn in Support of Nevro's Reply in Support of Motion for Summary Adjudication and Opposition to BSC's Motion for Summary Judgement (Document 375-1), Entire Document Sought—Joshua Goshorn opening Expert Report, *Nevro Corp. vs. Boston Scientific Corporation and Boston Scientific Neuromodulation Corporation*, Case No. 3:16-cv-06830-VC-MEJ, filed May 10, 2018, 1 page.
Declaration of Ben Pless in Support of Nevro's Reply in Support of Motion for Summary Adjudication and Opposition to BSC's Motion for Summary Judgement (Document 376), *Nevro Corp. vs. Boston Scientific Corporation and Boston Scientific Neuromodulation Corporation*, Case No. 3:16-cv-06830-VC-MEJ, filed May 10, 2018, 2 pages.
Exhibit A for Declaration of Ben Pless in Support of Nevro's Reply in Support of Motion for Summary Adjudication and Opposition to BSC's Motion for Summary Judgement (Document 376-1), Redacted Version of Document Sought to be Sealed—Opening Expert Report of Ben Pless, *Nevro Corp. vs. Boston Scientific Corporation and Boston Scientific Neuromodulation Corporation*, Case No. 3:16-cv-06830-VC-MEJ, filed May 10, 2018, 151 pages.
Exhibit B for Declaration of Ben Pless in Support of Nevro's Reply in Support of Motion for Summary Adjudication and Opposition to BSC's Motion for Summary Judgement (Document 376- 2), Redacted Version of Document Sought to be Sealed—Corrected Rebuttal Expert Report of Ben Pless regarding Validity, dated Mar. 5, 2018, *Nevro Corp. vs. Boston Scientific Corporation and Boston Scientific Neuromodulation Corporation*, Case No. 3:16-cv-06830-VC-MEJ, filed May 10, 2018, 116 pages.
Declaration of William Sanford Rosenberg in Support of Nevro's Reply in Support of Motion for Summary Adjudication and Opposition to BSC's Motion for Summary Judgement (Document 377), *Nevro Corp. vs. Boston Scientific Corporation and Boston Scientific Neuromodulation Corporation*, Case No. 3:16-cv-06830-VC-MEJ, filed May 10, 2018, 2 pages.

Exhibit A for Declaration of William Sanford Rosenberg in Support of Nevro's Reply in Support of Motion for Summary Adjudication and Opposition to BSC's Motion for Summary Judgement (Document 377-1), Curriculum Vitae of William Sanford Rosenberg, M.D., *Nevro Corp. vs. Boston Scientific Corporation and Boston Scientific Neuromodulation Corporation*, Case No. 3:16-cv-06830-VC-MEJ, filed May 10, 2018, 21 pages.
Exhibit B for Declaration of William Sanford Rosenberg in Support of Nevro's Reply in Support of Motion for Summary Adjudication and Opposition to BSC's Motion for Summary Judgement (Document 377-2), Redacted Version of Document Sought to be Sealed—Deposition of William Sanford Rosenberg, M.D. Faams, *Nevro Corp. vs. Boston Scientific Corporation and Boston Scientific Neuromodulation Corporation*, Case No. 3:16-cv-06830-VC-MEJ, filed May 10, 2018, 40 pages.
Declaration of Robert Schiff in Support of Nevro's Reply in Support of Motion for Summary Adjudication and Opposition to BSC's Motion for Summary Judgement (Document 378), *Nevro Corp. vs. Boston Scientific Corporation and Boston Scientific Neuromodulation Corporation*, Case No. 3:16-cv-06830-VC-MEJ, filed May 10, 2018, 2 pages.
Exhibit A—Updated—for Declaration of Robert Schiff in Support of Nevro's Reply in Support of Motion for Summary Adjudication and Opposition to BSC's Motion for Summary Judgement (Document 410), Redacted Version of ECF No. 382-10—Exhibit A to the May 9, 2018 Declaration of Robert Schiff, *Nevro Corp. vs. Boston Scintific Corporation and Boston Scientific Neuromodulation Corporation*, Case No. 3:16-cv-06830-VC-MEJ, filed May 10, 2018, 72 pages.
Declaration of Nicholas Fung in Support of Nevro's Reply in Support of Motion for Summary Adjudication and Opposition to BSC's Motion for Summary Judgement (Document 379), *Nevro Corp. vs. Boston Scientific Corporation and Boston Scientific Neuromodulation Corporation*, Case No. 3:16-cv-06830-VC-MEJ, filed May 10, 2018, 5 pages.
Exhibit 1 for Declaration of Nicholas Fung in Support of Nevro's Reply in Support of Motion for Summary Adjudication and Opposition to BSC's Motion for Summary Judgement (Document 379-1), Claims Chart, *Nevro Corp. vs. Boston Scientific Corporation and Boston Scientific Neuromodulation Corporation*, Case No. 3:16-cv-06830-VC-MEJ, filed May 10, 2018, 3 pages.
Exhibit 2 for Declaration of Nicholas Fung in Support of Nevro's Reply in Support of Motion for Summary Adjudication and Opposition to BSC's Motion for Summary Judgement (Document 379-2), Entire Document Sought to be Sealed—Document BSC-NVRO_00713169-172, *Nevro Corp. vs. Boston Scientific Corporation and Boston Scientific Neuromodulation Corporation*, Case No. 3:16-cv-06830-VC-MEJ, filed May 10, 2018, 1 page.
Exhibit 3 for Declaration of Nicholas Fung in Support of Nevro's Reply in Support of Motion for Summary Adjudication and Opposition to BSC's Motion for Summary Judgement (Document 379-3), Redacted Version of Document Sought to be Sealed—BSC's Second Supplemental Responses and Objections to Nevro's First Set of Interrogatory Request (1-8), *Nevro Corp. vs. Boston Scientific Corporation and Boston Scientific Neuromodulation Corporation*, Case No. 3:16-cv-06830-VC-MEJ, filed May 10, 2018, 13 pages.
Exhibit 4 for Declaration of Nicholas Fung in Support of Nevro's Reply in Support of Motion for Summary Adjudication and Opposition to BSC's Motion for Summary Judgement (Document 379-4), Redacted Version of Document Sought to be Sealed—Videotaped Deposition of Sridhar Kothandaraman, *Nevro Corp. vs. Boston Scientific Corporation and Boston Scientific Neuromodulation Corporation*, Case No. 3:16-cv-06830-VC-MEJ, filed May 10, 2018, 14 pages.
Exhibit 5 for Declaration of Nicholas Fung in Support of Nevro's Reply in Support of Motion for Summary Adjudication and Opposition to BSC's Motion for Summary Judgement (Document 379-5), Videotaped Deposition of Brian Erickson dated Dec. 15, 2017, *Nevro Corp. vs. Boston Scientific Corporation and Boston Scientific Neuromodulation Corporation*, Case No. 3:16-cv-06830-VC-MEJ, filed May 10, 2018, 7 pages.
Exhibit 6 for Declaration of Nicholas Fung in Support of Nevro's Reply in Support of Motion for Summary Adjudication and Oppo-

(56) References Cited

OTHER PUBLICATIONS sition to BSC's Motion for Summary Judgement (Document 379-6), Plaintiff's Brief regarding Claim Construction of the "Adapted to" Claim Term, *Nevro Corp.* vs. *Boston Scientific Corporation and Boston Scientific Neuromodulation Corporation*, Case No. 3:16-cv-06830-VC-MEJ, filed May 10, 2018, 7 pages.
Exhibit 7 for Declaration of Nicholas Fung in Support of Nevro's Reply in Support of Motion for Summary Adjudication and Opposition to BSC's Motion for Summary Judgement (Document 379-7), Plaintiff's Response Brief regarding Claim Construction of the "Adapted to" Claim Term, *Nevro Corp.* vs. *Boston Scientific Corporation and Boston Scientific Neuromodulation Corporation*, Case No. 3:16-cv-06830-VC-MEJ, filed May 10, 2018, 6 pages.
Exhibit 8 for Declaration of Nicholas Fung in Support of Nevro's Reply in Support of Motion for Summary Adjudication and Opposition to BSC's Motion for Summary Judgement (Document 379-8), Deposition of Ben Pless dated Apr. 10, 2018, *Nevro Corp.* vs. *Boston Scientific Corporation and Boston Scientific Neuromodulation Corporation*, Case No. 3:16-cv-06830-VC-MEJ, filed May 10, 2018, 31 pages.
Exhibit 9 for Declaration of Nicholas Fung in Support of Nevro's Reply in Support of Motion for Summary Adjudication and Opposition to BSC's Motion for Summary Judgement (Document 379-9), Deposition of Dr. Gene Fridman dated Mar. 7, 2018, *Nevro Corp.* vs. *Boston Scientific Corporation and Boston Scientific Neuromodulation Corporation*, Case No. 3:16-cv-06830-VC-MEJ, filed May 10, 2018, 62 pages.
Exhibit 10 for Declaration of Nicholas Fung in Support of Nevro's Reply in Support of Motion for Summary Adjudication and Opposition to BSC's Motion for Summary Judgement (Document 379-10), Expert Report and Declaration of Gene Fridman, Ph.D., regarding Claim Construction, *Nevro Corp.* vs. *Boston Scientific Corporation and Boston Scientific Neuromodulation Corporation*, Case No. 3:16-cv-06830-VC-MEJ, filed May 10, 2018, 6 pages.
Exhibit 11 for Declaration of Nicholas Fung in Support of Nevro's Reply in Support of Motion for Summary Adjudication and Opposition to BSC's Motion for Summary Judgement (Document 379-11), Article by Tan et al., *Nevro Corp.* vs. *Boston Scientific Corporation and Boston Scientific Neuromodulation Corporation*, Case No. 3:16-cv-06830-VC-MEJ, filed May 10, 2018, 8 pages.
Exhibit 12 for Declaration of Nicholas Fung in Support of Nevro's Reply in Support of Motion for Summary Adjudication and Opposition to BSC's Motion for Summary Judgement (Document 379-12), Decision Denying Institution of Inter Partes Review for U.S. Pat. No. 8,359,102 (Case IPR2015-01203), *Nevro Corp.* vs. *Boston Scientific Corporation and Boston Scientific Neuromodulation Corporation*, Case No. 3:16-cv-06830-VC-MEJ, filed May 10, 2018, 21 pages.
Exhibit 13 for Declaration of Nicholas Fung in Support of Nevro's Reply in Support of Motion for Summary Adjudication and Opposition to BSC's Motion for Summary Judgement (Document 379-13), Certified Copy of U.S. Pat. No. 9,327,125, *Nevro Corp.* vs. *Boston Scientific Corporation and Boston Scientific Neuromodulation Corporation*, Case No. 3:16-cv-06830-VC-MEJ, filed May 10, 2018, 66 pages.
Exhibit 14 for Declaration of Nicholas Fung in Support of Nevro's Reply in Support of Motion for Summary Adjudication and Opposition to BSC's Motion for Summary Judgement (Document 379-14), U.S. Pat. No. 9,492,664, *Nevro Corp.* vs. *Boston Scientific Corporation and Boston Scientific Neuromodulation Corporation*, Case No. 3:16-cv-06830-VC-MEJ, filed May 10, 2018, 25 pages.
Exhibit 15 for Declaration of Nicholas Fung in Support of Nevro's Reply in Support of Motion for Summary Adjudication and Opposition to BSC's Motion for Summary Judgement (Document 379-15), U.S. Pat. No. 9,339,655, *Nevro Corp.* vs. *Boston Scientific Corporation and Boston Scientific Neuromodulation Corporation*, Case No. 3:16-cv-06830-VC-MEJ, filed May 10, 2018, 23 pages.
Exhibit 16 for Declaration of Nicholas Fung in Support of Nevro's Reply in Support of Motion for Summary Adjudication and Opposition to BSC's Motion for Summary Judgement (Document 379-16), Redacted Version of Document Sought to be Sealed—Videotaped Deposition of Richard T. Mihran, Ph.D., dated Mar. 12, 2018, *Nevro Corp.* vs. *Boston Scientific Corporation and Boston Scientific Neuromodulation Corporation*, Case No. 3:16-cv-06830-VC-MEJ, filed May 10, 2018, 29 pages.
Exhibit 17 for Declaration of Nicholas Fung in Support of Nevro's Reply in Support of Motion for Summary Adjudication and Opposition to BSC's Motion for Summary Judgement (Document 379-17), Redacted Version of Document Sought to be Sealed—Videotaped Deposition of Jim Cassidy, dated May 17, 2017, *Nevro Corp.* vs. *Boston Scientific Corporation and Boston Scientific Neuromodulation Corporation*, Case No. 3:16-cv-06830-VC-MEJ, filed May 10, 2018, 13 pages.
Exhibit 18 for Declaration of Nicholas Fung in Support of Nevro's Reply in Support of Motion for Summary Adjudication and Opposition to BSC's Motion for Summary Judgement (Document 379-18), Redacted Version of Document Sought to be Sealed—Deposition of Adam Lipson, M.D., dated Apr. 12, 2018, *Nevro Corp.* vs. *Boston Scientific Corporation and Boston Scientific Neuromodulation Corporation*, Case No. 3:16-cv-06830-VC-MEJ, filed May 10, 2018, 10 pages.
Exhibit 19 for Declaration of Nicholas Fung in Support of Nevro's Reply in Support of Motion for Summary Adjudication and Opposition to BSC's Motion for Summary Judgement (Document 379-19), Redacted Version of Document Sought to be Sealed—BSC's Nov. 10, 2017 Supplemental Responses and Objections to Nevro's Interrogatory Requests Nos. 2, 4, 5, and 7, *Nevro Corp.* vs. *Boston Scientific Corporation and Boston Scientific Neuromodulation Corporation*, Case No. 3:16-cv-06830-VC-MEJ, filed May 10, 2018, 9 pages.
Exhibit 20 for Declaration of Nicholas Fung in Support of Nevro's Reply in Support of Motion for Summary Adjudication and Opposition to BSC's Motion for Summary Judgement (Document 379-20), Entire Document Sought to be Sealed—Deposition of Kaoru Adair, *Nevro Corp.* vs. *Boston Scientific Corporation and Boston Scientific Neuromodulation Corporation*, Case No. 3:16-cv-06830-VC-MEJ, filed May 10, 2018, 1 page.
Exhibit 21—Updated—for Declaration of Nicholas Fung in Support of Nevro's Reply in Support of Motion for Summary Adjudication and Opposition to BSC's Motion for Summary Judgement (Document 471), Redacted Version of ECF No. 382-24—Videotaped Deposition of Kaoru Adair dated May 10, 2017, *Nevro Corp.* vs. *Boston Scientific Corporation and Boston Scientific Neuromodulation Corporation*, Case No. 3:16-cv-06830-VC-MEJ, filed May 10, 2018, 18 pages.
Exhibit 22 Declaration of Nicholas Fung in Support of Nevro's Reply in Support of Motion for Summary Adjudication and Opposition to BSC's Motion for Summary Judgement (Document 379-22), Redacted Version of Document Sought to be Sealed—Nevro Corp.'s First Amended Disclosure of Asserted Claims and Infringement Contentions, *Nevro Corp.* vs. *Boston Scientific Corporation and Boston Scientific Neuromodulation Corporation*, Case No. 3:16-cv-06830-VC-MEJ, filed May 10, 2018, 6 pages.
Exhibit 23 for Declaration of Nicholas Fung in Support of Nevro's Reply in Support of Motion for Summary Adjudication and Opposition to BSC's Motion for Summary Judgement (Document 379-23), Entire Document Sought to be Sealed—Document BSC-NVRO_00720938-940, *Nevro Corp.* vs. *Boston Scientific Corporation and Boston Scientific Neuromodulation Corporation*, Case No. 3:16-cv-06830-VC-MEJ, filed May 10, 2018, 1 page.
Exhibit 24 for Declaration of Nicholas Fung in Support of Nevro's Reply in Support of Motion for Summary Adjudication and Opposition to BSC's Motion for Summary Judgement (Document 379-24), Redacted Version of Document Sought to be Sealed—Deposition of Joshua Goshorn, dated Mar. 23, 2018, *Nevro Corp.* vs. *Boston Scientific Corporation and Boston Scientific Neuromodulation Corporation*, Case No. 3:16-cv-06830-VC-MEJ, filed May 10, 2018, 15 pages.
Exhibit 25 for Declaration of Nicholas Fung in Support of Nevro's Reply in Support of Motion for Summary Adjudication and Opposition to BSC's Motion for Summary Judgement (Document 379-25), Redacted Version of Document Sought to be Sealed—Videotaped Deposition of Daniel Lanovaz, dated Mar. 21, 2018,

(56) References Cited

OTHER PUBLICATIONS

*Nevro Corp.* vs. *Boston Scientific Corporation and Boston Scientific Neuromodulation Corporation*, Case No. 3:16-cv-06830-VC-MEJ, filed May 10, 2018, 11 pages.
Exhibit 26 for Declaration of Nicholas Fung in Support of Nevro's Reply in Support of Motion for Summary Adjudication and Opposition to BSC's Motion for Summary Judgement (Document 379-26), Redacted Version of Document Sought to be Sealed—Rebuttal Expert Report of Richard T. Mihran, Ph.D. dated Feb. 14, 2018, *Nevro Corp.* vs. *Boston Scientific Corporation and Boston Scientific Neuromodulation Corporation*, Case No. 3:16-cv-06830-VC-MEJ, filed May 10, 2018, 23 pages.
Exhibit 27 for Declaration of Nicholas Fung in Support of Nevro's Reply in Support of Motion for Summary Adjudication and Opposition to BSC's Motion for Summary Judgement (Document 379-27), Expert Report of Richard T. Mihran, Ph.D., regarding Invalidity of U.S. Pat. No. 8,712,533; U.S. Pat. No. 9,327,125; U.S. Pat. No. 8,359,102; U.S. Pat. No. 9,480,842; U.S. Pat. No. 9,333,357; U.S. Pat. No. 8,792,988, and U.S. Pat. No. 8,768,472, *Nevro Corp.* vs. *Boston Scientific Corporation and Boston Scientific Neuromodulation Corporation*, Case No. 3:16-cv-06830-VC-MEJ, filed May 10, 2018, 6 pages.
Exhibit 28 for Declaration of Nicholas Fung in Support of Nevro's Reply in Support of Motion for Summary Adjudication and Opposition to BSC's Motion for Summary Judgement (Document 379-28), Declaration of Rafael Carbunaru in Support of Boston Scientific's Invalidity Contentions, *Nevro Corp.* vs. *Boston Scientific Corporation and Boston Scientific Neuromodulation Corporation*, Case No. 3:16-cv-06830-VC-MEJ, filed May 10, 2018, 13 pages.
Exhibit 29 for Declaration of Nicholas Fung in Support of Nevro's Reply in Support of Motion for Summary Adjudication and Opposition to BSC's Motion for Summary Judgement (Document 379-29), Redacted Version of Document Sought to be Sealed—Videotaped Deposition of Nevro Corp., with designated corporate representative Rafael Carbunaru, dated May 18, 2017, *Nevro Corp.* vs. *Boston Scientific Corporation and Boston Scientific Neuromodulation Corporation*, Case No. 3:16-cv-06830-VC-MEJ, filed May 10, 2018, 8 pages.
Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 382), *Nevro Corp.* vs. *Boston Scientific Corporation and Boston Scientific Neuromodulation Corporation*, Case No. 3:16-cv-06830-VC-MEJ, filed May 14, 2018, 13 pages.
Exhibit A—Updated—for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 468), Redacted Version of ECF No. 382-2—Nevro's Reply in Support of its Motion for Summary Adjudication and Opposition to BSC's Motion for Summary Judgment, *Nevro Corp.* vs. *Boston Scientific Corporation and Boston Scientific Neuromodulation Corporation*, Case No. 3:16-cv-06830-VC-MEJ, filed May 14, 2018, 40 pages.
Exhibit B for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 382-3), Redacted Version of Document Sought to be Filed under Seal—Expert Report of Joshua Goshorn, *Nevro Corp.* vs. *Boston Scientific Corporation and Boston Scientific Neuromodulation Corporation*, Case No. 3:16-cv-06830-VC-MEJ, filed May 14, 2018, 15 pages.
Exhibit C for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 382-5), Redacted Version of Document Sought to be Filed under Seal—Expert Report of William S. Rosenberg, M.D., Faans, *Nevro Corp.* vs. *Boston Scientific Corporation and Boston Scientific Neuromodulation Corporation*, Case No. 3:16-cv-06830-VC-MEJ, filed May 14, 2018, 41 pages.
Exhibit D—Updated—for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 469), Redacted Version of ECF No. 382-8—Opening Expert Report of Ben Pless regarding Infringement, dated Jan. 18, 2018, *Nevro Corp.* vs. *Boston Scientific Corporation and Boston Scientific Neuromodulation Corporation*, Case No. 3:16-cv-06830-VC-MEJ, filed May 14, 2018, 152 pages.
Exhibit E—Updated—for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 470), Redacted Version of ECF No. 382-10—Expert Report of Robert Schiff, Ph.D., RAC, CQA, FRAPS, *Nevro Corp.* vs. *Boston Scientific Corporation and Boston Scientific Neuromodulation Corporation*, Case No. 3:16-cv-06830-VC-MEJ, filed May 14, 2018, 72 pages.
Exhibit F for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 382-11), Redacted Version of Document Sought to be Filed under Seal—Cross-Border HCP Arrangement Request, *Nevro Corp.* vs. *Boston Scientific Corporation and Boston Scientific Neuromodulation Corporation*, Case No. 3:16-cv-06830-VC-MEJ, filed May 14, 2018, 6 pages.
Exhibit G for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 382-13), Redacted Version of Document Sought to be Filed under Seal—BSC's Second Supplemental Responses and Objections to Nevro's First Set of Interrogatory Request (1-8), *Nevro Corp.* vs. *Boston Scientific Corporation and Boston Scientific Neuromodulation Corporation*, Case No. 3:16-cv-06830-VC-MEJ, filed May 14, 2018, 14 pages.
Exhibit H for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 382-15), Redacted Version of Document Sought to be Filed under Seal—Videotaped Deposition of Sridhar Kothandaraman, dated Nov. 17, 2017, *Nevro Corp.* vs. *Boston Scientific Corporation and Boston Scientific Neuromodulation Corporation*, Case No. 3:16-cv-06830-VC-MEJ, filed May 14, 2018, 15 pages.
Exhibit I for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 382-17), Redacted Version of Document Sought to be Filed under Seal—Videotaped Deposition of Richard T. Mihran, dated Mar. 12, 2018, *Nevro Corp.* vs. *Boston Scientific Corporation and Boston Scientific Neuromodulation Corporation*, Case No. 3:16-cv-06830-VC-MEJ, filed May 14, 2018, 30 pages.
Exhibit J for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 382-19), Redacted Version of Document Sought to be Filed under Seal—BSC's Nov. 10, 2017 Supplemental Responses and Objections to Nevro's Interrogatory Requests Nos. 2, 4, 5, and 7, *Nevro Corp.* vs. *Boston Scientific Corporation and Boston Scientific Neuromodulation Corporation*, Case No. 3:16-cv-06830-VC-MEJ, filed May 14, 2018, 10 pages.
Exhibit K for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 382-21), Redacted Version of Document Sought to be Filed

(56) References Cited

OTHER PUBLICATIONS under Seal—Dec. 14, 2016 Correspondence between Boston Scientific and U.S. Food and Drug Administration, *Nevro Corp. vs. Boston Scientific Corporation and Boston Scientific Neuromodulation Corporation*, Case No. 3:16-cv-06830-VC-MEJ, filed May 14, 2018, 23 pages.
Exhibit L—Updated for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 471), Updated Redacted Version of ECF No. 382-24—Videotaped Deposition of Kaoru Lee Adair, dated May 10, 2017, *Nevro Corp. vs. Boston Scientific Corporation and Boston Scientific Neuromodulation Corporation*, Case No. 3:16-cv-06830-VC-MEJ, filed May 14, 2018, 18 pages.
Exhibit M for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 382-25), Redacted Version of Document Sought to be Filed under Seal—Nevro Corp.'s First Amended Disclosure of Asserted Claims and Infringement Contentions, *Nevro Corp. vs. Boston Scientific Corporation and Boston Scientific Neuromodulation Corporation*, Case No. 3:16-cv-06830-VC-MEJ, filed May 14, 2018, 7 pages.
Exhibit N for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 382-27), Redacted Version of Document Sought to be Filed under Seal—Feb. 2016 Email regarding Precision 10K Training Follow-up, *Nevro Corp. vs. Boston Scientific Corporation and Boston Scientific Neuromodulation Corporation*, Case No. 3:16-cv-06830-VC-MEJ, filed May 14, 2018, 5 pages.
Exhibit O for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 382-29), Redacted Version of Document Sought to be Filed under Seal—Deposition of Joshua Goshorn dated Mar. 23, 2018, *Nevro Corp. vs. Boston Scientific Corporation and Boston Scientific Neuromodulation Corporation*, Case No. 3:16-cv-06830-VC-MEJ, filed May 14, 2018, 16 pages.
Exhibit P for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 382-31), Redacted Version of Document Sought to be Filed under Seal—Videotaped Deposition of Daniel Lanovaz dated Mar. 21, 2018, *Nevro Corp. vs. Boston Scientific Corporation and Boston Scientific Neuromodulation Corporation*, Case No. 3:16-cv-06830-VC-MEJ, filed May 14, 2018, 12 pages.
[Proposed] Order Granting Administrative Motion to File under Seal Portions of Nevro's Reply in Support of It's Motion for Summary Adjudication and Opposition to BSC's Motion for Summary Judgement and Supporing Documents (Document 382-33), *Nevro Corp. vs. Boston Scientific Corporation and Boston Scientific Neuromodulation Corporation*, Case No. 3:16-cv-06830-VC-MEJ, filed May 14, 2018, 7 pages.
Updated Boston Scientific's Reply in Support of Motion for Summary Judgement (Document 473), Updated Redacted Version of ECF No. 397-3, *Nevro Corp. vs. Boston Scientific Corporation and Boston Scientific Neuromodulation Corporation*, Case No. 3:16-cv-06830-VC-MEJ, filed Jul. 30, 2018, 27 pages.
Declaration of Carson D. Anderson in Support of Boston Scientific's Reply in Support of Motion for Summary Judgement (Document 398-1), Redacted Version of Document Sought to be Filed under Seal—Cross-Border HCP Arrangement Request, *Nevro Corp. vs. Boston Scientific Corporation and Boston Scientific Neuromodulation Corporation*, Case No. 3:16-cv-06830-VC- MEJ, filed May 24, 2018, 3 pages.
Exhibit 1 for Declaration of Carson D. Anderson in Support of Boston Scientific's Reply in Support of Motion for Summary Judgement (Document 398-2), Redacted Version of Document Sought to be Filed under Seal—May 2004 Email regarding Post-Market Studies for AB SCS System, *Nevro Corp. vs. Boston Scientific Corporation and Boston Scientific Neuromodulation Corporation*, Case No. 3:16-cv-06830-VC-MEJ, filed May 24, 2018, 5 pages.
Exhibit 2 for Declaration of Carson D. Anderson in Support of Boston Scientific's Reply in Support of Motion for Summary Judgement (Document 398-3), Redacted Version of Document Sought to be Filed under Seal—Corrected Rebuttal Expert Report of Ben Pless regarding Validity, dated Mar. 5, 2018, *Nevro Corp. vs. Boston Scientific Corporation and Boston Scientific Neuromodulation Corporation*, Case No. 3:16-cv-06830-VC-MEJ, filed May 24, 2018, 4 pages.
Exhibit 3 for Declaration of Carson D. Anderson in Support of Boston Scientific's Reply in Support of Motion for Summary Judgement (Document 398-4), U.S. Pat. No. 7,389,145 by Kilgore et al., *Nevro Corp. vs. Boston Scientific Corporation and Boston Scientific Neuromodulation Corporation*, Case No. 3:16-cv-06830-VC-MEJ, filed May 24, 2018, 12 pages.
Exhibit 4 for Declaration of Carson D. Anderson in Support of Boston Scientific's Reply in Support of Motion for Summary Judgement (Document 398-5), Redacted Version of Document Sought to be Filed under Seal—Videotaped Deposition of Robert Schiff, dated Mar. 15, 2018, *Nevro Corp. vs. Boston Scientific Corporation and Boston Scientific Neuromodulation Corporation*, Case No. 3:16-cv-06830-VC-MEJ, filed May 24, 2018, 19 pages.
Exhibit 5 for Declaration of Carson D. Anderson in Support of Boston Scientific's Reply in Support of Motion for Summary Judgement (Document 398-6), Filed under Seal—Document NEVRO_BSXCA0093092-109, *Nevro Corp. vs. Boston Scientific Corporation and Boston Scientific Neuromodulation Corporation*, Case No. 3:16-cv-06830-VC-MEJ, filed May 24, 2018, 1 page.
Exhibit 6 for Declaration of Carson D. Anderson in Support of Boston Scientific's Reply in Support of Motion for Summary Judgement (Document 398-7), Filed under Seal—Document NEVRO_BSXCA0067869-75, *Nevro Corp. vs. Boston Scientific Corporation and Boston Scientific Neuromodulation Corporation*, Case No. 3:16-cv-06830-VC-MEJ, filed May 24, 2018, 1 page.
Exhibit 7 for Declaration of Carson D. Anderson in Support of Boston Scientific's Reply in Support of Motion for Summary Judgement (Document 398-8), Filed under Seal—Document NEVRO_BSXCA0147580-86, *Nevro Corp. vs. Boston Scientific Corporation and Boston Scientific Neuromodulation Corporation*, Case No. 3:16-cv-06830-VC-MEJ, filed May 24, 2018, 1 page.
Exhibit 8 for Declaration of Carson D. Anderson in Support of Boston Scientific's Reply in Support of Motion for Summary Judgement (Document 398-9), Filed under Seal—Opening Expert Report of Ben Pless regarding Infringement, dated Jan. 18, 2018, *Nevro Corp. vs. Boston Scientific Corporation and Boston Scientific Neuromodulation Corporation*, Case No. 3:16-cv-06830-VC-MEJ, filed May 24, 2018, 7 pages.
Exhibit 9 for Declaration of Carson D. Anderson in Support of Boston Scientific's Reply in Support of Motion for Summary Judgement (Document 398-10), Filed under Seal—Expert Report of W. Todd Schoettelkotte Relating to Damages, dated Jan. 18, 2018, *Nevro Corp. vs. Boston Scientific Corporation and Boston Scientific Neuromodulation Corporation*, Case No. 3:16-cv-06830-VC-MEJ, filed May 24, 2018, 1 page.
Exhibit 10 for Declaration of Carson D. Anderson in Support of Boston Scientific's Reply in Support of Motion for Summary Judgement (Document 398-11), Redacted Version of Document Sought to be Filed under Seal—Design Change Analysis Form (DCAF), *Nevro Corp. vs. Boston Scientific Corporation and Boston Scientific Neuromodulation Corporation*, Case No. 3:16-cv-06830-VC-MEJ, filed May 24, 2018, 2 pages.
Exhibit 11 for Declaration of Carson D. Anderson in Support of Boston Scientific's Reply in Support of Motion for Summary

(56) References Cited

OTHER PUBLICATIONS

Judgement (Document 398-12), Redacted Version of Document Sought to be Filed under Seal—Videotaped Deposition of Rafael Carbunaru, Ph.D., dated Nov. 14, 2017, *Nevro Corp. vs. Boston Scientific Corporation and Boston Scientific Neuromodulation Corporation*, Case No. 3:16-cv-06830-VC-MEJ, filed May 24, 2018, 9 pages.
Exhibit 12 for Declaration of Carson D. Anderson in Support of Boston Scientific's Reply in Support of Motion for Summary Judgement (Document 398-13), Declaration of James Thacker under 37 CFR 1.1.32, dated Jun. 6, 2013, *Nevro Corp. vs. Boston Scientific Corporation and Boston Scientific Neuromodulation Corporation*, Case No. 3:16-cv-06830-VC-MEJ, filed May 24, 2018, 9 pages.
Exhibit 13 for Declaration of Carson D. Anderson in Support of Boston Scientific's Reply in Support of Motion for Summary Judgement (Document 398-14), Information Disclosure Statement SB-08 Form for U.S. Appl. No. 14/525,134, *Nevro Corp. vs. Boston Scientific Corporation and Boston Scientific Neuromodulation Corporation*, Case No. 3:16-cv-06830-VC-MEJ, filed May 24, 2018, 13 pages.
Exhibit 14 for Declaration of Carson D. Anderson in Support of Boston Scientific's Reply in Support of Motion for Summary Judgement (Document 398-15), Amendment in Response to Final Office Action for U.S. Appl. No. 12/765,685, filed Sep. 19, 2013, *Nevro Corp. vs. Boston Scientific Corporation and Boston Scientific Neuromodulation Corporation*, Case No. 3:16-cv-06830-VC-MEJ, filed May 24, 2018, 15 pages.
Exhibit 15 for Declaration of Carson D. Anderson in Support of Boston Scientific's Reply in Support of Motion for Summary Judgement (Document 398-16), Amendment in Response to Non-Final Office Action for U.S. Appl. No. 13/830,992, filed Feb. 24, 2014, *Nevro Corp. vs. Boston Scientific Corporation and Boston Scientific Neuromodulation Corporation*, Case No. 3:16-cv-06830-VC-MEJ, filed May 24, 2018, 15 pages.
Exhibit 16 for Declaration of Carson D. Anderson in Support of Boston Scientific's Reply in Support of Motion for Summary Judgement (Document 398-17), Amendment in Response to Final Office Action for U.S. Appl. No. 14/292,671, filed Jan. 17, 2017, *Nevro Corp. vs. Boston Scientific Corporation and Boston Scientific Neuromodulation Corporation*, Case No. 3:16-cv-06830-VC-MEJ, filed May 24, 2018, 12 pages.
Declaration of J. Lawrence Stevens in Support of Boston Scientific's Reply in Support of Motion for Summary Judgement (Document 398-18), *Nevro Corp. vs. Boston Scientific Corporation and Boston Scientific Neuromodulation Corporation*, Case No. 3:16-cv-06830-VC-MEJ, filed May 24, 2018, 34 pages.
Boston Scientific's Responsive Claim Construction Brief, Opposition to in Nevro's Motion for Summary Judgment and Opening Motion for Summary Judgment (Document 358), *Nevro Corp. vs. Boston Scientific Corporation and Boston Scientific Neuromodulation Corporation*, Case No. 3:16-cv-06830-VC-MEJ, filed Apr. 26, 2018, 60 pages.
Declaration of Rafael Carbunaru in Support of Boston Scientific Administrative Motion to File under Seal Portions of Boston Scientific's Opposition to Nevro's Motion to Strike BSC's Undisclosed Invalidity Theories (Dkt No. 340) and Supporting Documents (Document 355-2), *Nevro Corp. vs. Boston Scientific Corporation and Boston Scientific Neuromodulation Corporation*, Case No. 3:16-cv-06830-VC-MEJ, filed Apr. 26, 2018, 3 pages.
Declaration of Sridhar Kothandaraman (Document 356-1), *Nevro Corp. vs. Boston Scientific Corporation and Boston Scientific Neuromodulation Corporation*, Case No. 3:16-cv-06830-VCMEJ, filed Apr. 26, 2018, 4 pages.
Exhibit B to the Declaration of Clara W. Wang in Support of Nevro's Administrative Motion to File under Seal Portions of Nevro's Reply to Strike BSC's Invalidity Positions and Supporting Documents (Dkt No. 366) (Document 368-4), *Nevro Corp. vs. Boston Scientific Corporation and Boston Scientific Neuromodulation Corporation*, Case No. 3:16-cv-06830-VC-MEJ, filed May 7, 2018, 10 pages.
Order Re: Claim Construction and Cross-Motions for Summary Judgement (Document 449), *Nevro Corp. vs. Boston Scientific Corporation and Boston Scientific Neuromodulation Corporation*, Case No. 3:16-cv-06830-VC-MEJ, filed Jul. 24, 2018, 9 pages.
Tentative Ruling (Document 422), *Nevro Corp. vs. Boston Scientific Corporation and Boston Scientific Neuromodulation Corporation*, Case No. 3:16-cv-06830-VC-MEJ, filed Jul. 5, 2018, 3 pages.
Nevro Written Submissions for European Patent No. 2207587, Opponents: *Medtronic Inc., and Boston Scientific Neuromodulation Corporation*, mailed Jul. 24, 2018, 9 pages.
Notice of Opposition for European Patent No. 3156099, Proprietor of the Patent: *Nevro Corporation*; Opponent: *Boston Scientific Neuromodulation Corporation*, Dec. 15, 2017, 27 pages.
Thomson et al., "Effects of Rate on Analgesia in Kilohertz Frequency Spinal Cord Stimulation: Results of the PROCO Randomized Controlled Trial," Neuromodulation: Technology at the Neural Interface, 2017, 10 pages.
"The Need for Mechanism-Based Medicine in Neuromodulation," Neuromodulation: Technology at the Neural Interface, 2012, 7 pages.
Abejon et al., "Is Impedance a Parameter to be Taken into Account in Spinal Cord Stimulation?" Pain Physician, 2007, 8 pages.
Acticare.com website, http://web.archive.org/web/*/acticare.com, Internet Archive Way Back Machine, 2012, 22 pages.
Advanced Neuromodulation Systems, Compustim SCS Systems, Clinical Manual, 1997, 52 pages.
Agnew et al., "Considerations for safety with chronically implanted nerve electrodes," Epilepsia, 31.s2, 1990, 6 pages.
Al-Kaisy et al., "10 KHz High-Frequency Spinal Cord Stimulation for Chronic Axial Low Back Pain in Patients With No History of Spinal Surgery: A Preliminary, Prospective, Open Label and Proof-of-Concept Study," Neuromodulation: Technology at the Neural Interface, 2016, 8 pages.
Al-Kaisy et al., "Prospective, Randomized, Sham-Control, Double Blind, Crossover Trial of Subthreshold Spinal Cord Stimulation at Various Kilohertz Frequencies in Subjects Suffering from Failed Back Surgery Syndrome," International Neuromodulation Society, 2018, 9 pages.
Al-Kaisy et al., "Sustained Effectiveness of 10kHz High-Frequency Spinal Cord Stimulation for Patients with Chronic, Low Back Pain: 24-month Results of Prospective Multicenter Study," Pain Medicine, 2014, 8 pages.
Al-Kaisy et al., "The Use of 10-Kilohertz Spinal Cord Stimulation in a Cohort of Patients with Chronic Neuropathic Limb Pain Refractory to Medical Management," Neuromodulation Technology at the Neural, Interface, 2015, 6 pages.
Al-Kaisy et al., Poster: "High-Frequency Spinal Cord Stimulation at 10 KHz for the Treatment of Chronic Back Pain Patients without Prior Back Surgery," 1 page.
Alo et al., "Factors Affecting Impedance of Percutaneous Leads in Spinal Cord Stimulation," International Neuromodulation Society, vol. 9, No. 2, 2006, 8 pages.
Alo et al., "New Trends in Neuromodulation for the Management of Neuropathic Pain," Neurosurgery, vol. 50, No. 4, Apr. 2002, 15 pages.
Amendment in Response to Ex Parte Office Action for U.S. Appl. No. 13/446,970, First Named Inventor: Konstantinos Alataris, Mailed: Nov. 28, 2012, 14 pages.
Amendment in Response to Non-Final Office Action for U.S. Appl. No. 13/245,450, First Named Inventor: Konstantinos Alataris, filed: Feb. 7, 2012, 15 pages.
Amendment in Response to Non-Final Office Action for U.S. Appl. No. 12/765,747, First Named Inventor: Konstantinos Alataris, Mailed: Jan. 24, 2014, 21 pages.
Applicant-Initiated Interview Summary for U.S. Appl. No. 13/245,450, First Named Inventor: Konstantinos Alataris, Mailed: Feb. 1, 2012, 2 pages.
Applicant-Initiated Interview Summary for U.S. Appl. No. 13/725,770, First Named Inventor: Konstantinos Alataris, Mailed: Apr. 5, 2013, 3 pages.

(56) References Cited

OTHER PUBLICATIONS

Applicant-Initiated Interview Summary for U.S. Appl. No. 12/765,747, First Named Inventor: Konstantinos Alataris, Mailed: Sep. 11, 2013, 3 pages.
Application Data Sheet for U.S. Appl. No. 13/446,970 (U.S. Pat. No. 8,359,102), First Named Inventor: Konstantinos Alataris, Filed: Apr. 13, 2012, 6 pages.
Augustinsson et al., "Spinal Cord Stimulation in Cardiovascular Disease," Functional Neurosurgery, vol. 6, No. 1, Jan. 1995, 10 pages.
Bahdra et al., Stimulation of High-Frequency Sinusoidal Electrical Block of Mammalian Myelinated Axons, J Comput Neurosco, 22:313-326, 2007.
Bara et al., Poster re: High Frequency Spinal Cord Stimulation for Dominant Back Pain—1 year follow up, 2013, 1 page.
Barolat et al., "Multifactorial Analysis of Epidural Spinal Cord Stimulation," Sterotactic and Functional Neurosurgery, 1991; 56: 77-103.
Barolat et al., "Spinal Cord Stimulation for Chronic Pain Management," Seminars in Neurosurgery, vol. 15, Nos. 2/3, 2004, 26 pages.
Barolat et al., "Surgical Management of Pain—Spinal Cord Stimulation: Equipment and Implantation Techniques," Chapter 41, Thieme Medical Publishers, New York, 2002, 11 pages.
Bennett et al., "Spinal Cord Stimulation for Complex regional pain syndrome I [RSD]: a Retrospective Multicenter Experience from 1995 to 1998 of 101 patients." Neuromodulation, vol. 2, No. 3, 1999, 9 pages.
Benyamin et al., "A Case of Spinal Cord Stimulation in Raynaud's Phenomenon: Can Subthreshold Sensory Stimulation Have an Effect?" Pain Physician www.painphysicianjournal.com, 2007, 6 pages.
Bhadra et al., "High Frequency electrical conduction block of the pudendal nerve," Journal of Neural Engineering—Institute of Physics Publishing, ; 2006, 8 pages.
Bhadra MD, Niloy et al., "High-Frequency Electrical Conduction Block of Mammalian Peripheral Motor Nerve," Muscle and Nerve, Dec. 2005, 9 pages.
BionicNavigator Software Guide, Part MP9055261-001, 2004, 58 pages.
Boger et al., "Bladder Voiding by Combined High Frequency Electrical Pudendal Nerve Block and Sacral Root Stimulation," Neurourology and Urodynamics, 27, 2008, 5 pages.
Boston Scientific "Precision™ Spinal Cord Stimulator System Clinician Manual—Directions for Use," 2015, 74 pages.
Boston Scientific, News Release: "New Data Presented at NANS 2014 Demonstrate Long-Term, Low Back Pain Relief with Boston Scientific Precision Spectra™ Spinal Cord Stimulator System," Dec. 12, 2014, 8 pages.
Bowman and McNeal, Response of Single Alpha Motoneurons to High-Frequency Pulse Trains, Appl. Neurophysiol. 49, p. 121-138, 1986, 10 pages.
Bronstein et al., "The Rationale Driving the Evolution of Deep Brain Stimulation of Constant-Current Devices," International Neuromodulation Society 2014, 5 pages.
Broseta et al., "High-Frequency cervical spinal cord stimulation in spasticity and motor disorders," Advances in Stereotactic and Functional Neurosurgery 7. Springer Verlag 1987, 6 pages.
Burton, Charles, "Dorsal Column Stimulation: Optimization of Application," Surgical Neurology, vol. 4, No. 1, Jul. 1975, 10 pages.
Butt et al., "Histological Findings Using Novel Stimulation Parameters in a Caprine Model," European Journal of Pain Supplements, 2011, 2 pages.
Cahana et al., "Acute Differential Modulation of Synaptic Transmission and Cell Survival During Exposure to Pulsed and Continuous Radiofrequency Energy," Journal of Pain, vol. 4, No. 4, May 2003, 6 pages.
Cameron et al., "Effects of posture on stimulation parameters in spinal cord stimulation," Neuromodulation: Technology at the Neural Interface 1.4, 1998, 8 pages.

Camilleri et al., "Intra-abdominal vagal blocking (VBLOC therapy): clinical results with a new implantable medical device," Surgery 143.6, 2008, 9 pages.
ClinicalTrials.gov, "Safety and Effectiveness Study of the Precision SCS System Adapted for High-Rate Spinal Cord Stimulation (Accelerate)," https://clinicaltrials.gov/ct2/show/NCT02093793?term=boston+scientific&recr=Open&cond=%22Pain%22&rank=3, Feb. 2015, 3 pages.
Crapanzano et al., "High Frequency Spinal Cord Stimulation for Complex Regional Pain Syndrome: A Case Report," Pain Physician, 2017, 6 pages.
Crosby et al., "Stimulation Parameters Define the Effectiveness of Burst Spinal Cord Stimulation in a Rat Model of Neuropathic Pain," Neuromodulation Technology at the Neural Interface, International Neurmodulation Society, 2014, 8 pages.
Cuellar et al., "Effect of High Frequency Alternating Current ; on Spinal Afferent Nociceptive Transmission," Neuromodulation: Technology at the Neural Interface, 2012, 10 pages.
Curriculum Vitae and Declaration of Dr. Ganesan Baranidharan, 4 pages, 2016.
Curriculum Vitae and Declaration of Dr. Jonathan Miller, 20 pages, Oct. 25, 2016.
Curriculum Vitae and Declaration of Dr. Simon James Thomson, Oct. 24, 2016, 2 pages.
Curriculum Vitae and Declaration of Prof. Bengt Linderoth, Oct. 21, 2016, 3 pages.
Curriculum Vitae of Michael A. Moffitt, 2015, 2 pages.
De Carolis et al., Poster: "Efficacy of Spinal Cord Stimulation (SCS) in the Treatment of Failed Back Surgery Syndrome (FBSS): a comparative study," 2013, 1 page.
De Ridder et al., U.S. Appl. No. 60/895,061, Applicant: Dirk De Ridder, filed Mar. 15, 2007, 47 pages.
Decision and Minutes: Opposition of European Patent No. 2421600 by Boston Scientific Neuromodulation Corporation, Apr. 3, 2017, 28 pages.
Declaration of Cameron C. McIntyre, Ph.D., May 6, 2015, 88 pages.
Declaration of Cameron C. McIntyre, Ph.D., May 6, 2015, 57 pages.
Declaration of Dr. Jonathan Miller on behalf of European Patent No. 2853285, 26 pages, May 16, 2017.
Declaration of M. Jason D. Rahn for European Patent No. 2243510, dated Feb. 2, 2017, 2 pages.
Declaration of M. Jason D. Rahn, Jan. 7, 2015, 7 pages.
Declaration of Prof. Bengt Linderoth for European Patent No. 2421600, dated Dec. 16, 2016 2 pages.
DeRidder et al., "Are Paresthesias necessary for pain suppression in SCS—Burst Stimulation," Brain, Brain Research Center Antwerp of Innovative and Interdisciplinary Neuromodulation, 2010, 27 pages.
DeRidder et al., "Burst Spinal Cord Stimulation: Toward Paresthesia-Free Pain Suppression," www.neurosurgery-online.com, vol. 66, Nos. 5, May 2010, 5 pages.
Dorland's Illustrated Medical Dictionary, Twenty-sixth Edition, "Paresthesia," 1981, 4 pages.
Doug Atkins of Medtronic Neurological, "Medtronic Neurostimulation Leads, 510(k) Summary," Submission Prepared: Feb. 27, 2004, 6 pages.
Duyvendak et al., "Spinal Cord Stimulation With a Dual Quadripolar Surgical Lead Placed in General Anesthesia is Effective in Treating Intractable Low Back and Leg Pain," Neuromodulation: Technology at the Neural Interface, vol. 10, No. 2, 2007, 7 pages.
Eddicks et al., "Thoracic Spinal Cord Stimulation Improves Functional Status and Relieves Symptoms in Patients with Refractory Angina Pectoris: The First Placebo-Controlled Randomised Study," Heart Journal, 2007, 6 pages.
European Extended Search Report for European Patent Application No. 17154846.4, Applicant: Nevro Corporation, mailed Jul. 11, 2017, 6 pages.
European Search Report for European Application No. 10160641.6, Applicant: Nevro Corporation, mailed Apr. 12, 2011, 7 pages.
European Search Report, European Application No. EP10160569, Applicant: Nevro Corporation, mailed Jun. 9, 2010, 7 pages.
Ex Parte Office Action for U.S. Appl. No. 13/446,970, First Inventor Named: Konstantinos Alataris, Mailed: Oct. 15, 2012, 9 pages.

(56) References Cited

OTHER PUBLICATIONS

Feeling vs. Function Poster, Mager and Associates Consulting, 2009, 1 page.
First Preliminary Amendment for U.S. Appl. No. 13/446,970, First Named Inventor: Konstantinos Alataris, Mailed: May 18, 2012, 7 pages.
Geddes, "A Short History of the electrical stimulation of excitable tissue—Including Electrotherapeutic Applications," The Physiologist, vol. 27, No. 1, Feb. 1984, 51 pages.
Grill, Warren et al., "Stimulus Waveforms for Selective Neural Stimulation," IEEE Engineering in Medicine and Biology, Jul./Aug. 1995, pp. 375-385.
Gulve et al., Poster: "10kHz High Frequency Spinal Cord Stimulation: Middlesbrough Experience," 2013, 1 page.
Guo et al., "Design and Implement of a Mini-Instrument for Rehabilitation with Transcutaneous Electrical Nerve Stimulation," School of Medical Instrument and Food Engineering, University of Shanghai for Science and Technology, Shanghai China, Mar. 31, 2007, 5 pages.
Hefferman et al., "Efficacy of Transcutaneous Spinal Electroanalgesia in Acute Postoperative Pain Management," Anesthesiology, 2001, 2 pages.
Higuchi et al., "Exposure of the Dorsal Root Ganglion in Rats to Pulsed Radiofrequency Currents Activates Dorsal Horn Lamina I and II Neurons," Neurosurgery, vol. 50, No. 4, Apr. 2002, 7 pages.
Hilberstadt et al., "The Effect of Transcutaneous Spinal Electroanalgesia upon Chronic Pain: A single case study," Physiotherapy, vol. 86 No. 3, Mar. 2000, 2 pages.
Holsheimer—Effectiveness of Spinal Cord Stimulation in the Management of Chronic Pain: Analysis of Technical Drawbacks and Solutions, Neurosurgery, vol. 40, No. 5, May 1997, pp. 990-999.
Hopp et al., "Effect of anodal blockade of myelinated fibers on vagal c-fiber afferents," American Journal Physiological Society, Nov. 1980; 239(5), 9 pages.
Hoppenstein, Reuben, "Electrical Stimulation of the Ventral and Dorsal Columns of the Spinal Cord for Relief of Chronic Intractable Pain: Preliminary Report," Surgical Neurology, vol. 4, No. 1, Jul. 1975, 9 pages.
House et al., "Safety and Efficacy of the House/3M Cochlear Implant in Profoundly Deaf Adults," Otolaryngologic Clinics of North America, vol. 19, No. 2, May 1986, 12 pages.
Huxely et al., "Excitation and Conduction in Nerve: Quantitative Analysis," Science, Sep. 11, 1964; 145: 1154-9.
International Neuromodulation Society 10th World Congress, Neuromodulation: Technology that Improves Patient Care, London, England, May 21-26, 2011, 385 pages.
International Search Report and Written Opinion, International Application ; No. PCT/US10/32124, Applicant: Nevro Corporation, European Patent Office, mailed Jun. 16, 2010, 28 pages.
J.P. Morgan North America Equity Research, "Nevro—Let the Launch Begin: Senza Approved, Raising PT to $54," www.jpmorganmarkets.com, May 10, 2015, 8 pages.
J.P. Morgan North America Equity Research, "Nevro—Welcome to the Future of Spinal Cord Stimulation Initiating at OW with $34 Price Target," www.jpmorganmarkets.com, Dec. 1, 2014, 39 pages.
Jacques et al., "Development of a New Implantable Bio-Telestimulator," Surg. Neurol., vol. 13, May 1980, 2 pages.
Jain et al., Abstract—"Accelerate: A Prospective Multicenter Trial Evaluating the Use of High-Rate Spinal Cord Stimulation in the Management of Chronic Intractable Pain," The American Academy of Pain Medicine, 2015, 1 page.
Jang et al., "Analysis of Failed Spinal Cord Stimulation Trails in the Treatment of Intractable Chronic Pain," J. Korean Neurosurg Soc 43, 2008, 5 pages.
Jezernik et al., "Electrical Stimulation for the Treatment of Bladder Dysfunction: Current Status and Future Possibilities," Neurological Research, vol. 24, Jul. 2002, 18 pages.
JMP Securities, "Nevro Corp. (NVRO) Initiating Coverage on Nevro Corp. with a Market Outperform Rating—Investment Highlights," Dec. 1, 2014, 42 pages.

Kapural et al., "Comparison of 10-kHz High Frequency and Traditional Low-Frequency Spinal Cord Stimulation for the Treatment of Chronic Back and Leg Pain: 24-Month Results From a Multicenter, Randomized, Controlled Pivotal Trial," Neurosurgery, vol. 79, No. 5, Nov. 2016, 11 pages.
Kapural et al., "Novel 10-Khz High Frequency Therapy (HF10 Therapy) is Superior to Traditional Low-Frequency Spinal Cord Stimulation for Treatment of Chronic Back and Leg Pain," Anesthesiology the Journal of American Society of Anesthesiologists, Inc., 2015, 11 pages.
Kilgore et al. "Nerve Conduction Block Utilizing High-Frequency Alternating Current" Medical & Biology Engineering and Computing, 2004, vol. 24, pp. 394-406.
Kilgore et al. "Reversible Nerve Conduction Block Using Kilohertz Frequency Alternating Current," Neuromodulation Technology at the Neural Interface, International Neuromodulation Society, 2013, 13 pages.
Kreitler et al., "Chapter 15: Implantable Devices and Drug Delivery Systems—The Handbook for Chronic Pain," NOVA Biomedical Books, New York, 2007, 17 pages.
Krista Oakes of Neuromed, Inc., "Implanted Spinal Cord Stimulator Lead 510(k) Summary of Safety and Effectiveness," Submission Prepared Feb. 21, 1996, 3 pages.
Kuechmann et al., Abstract #853: "Could Automatic Position Adaptive Stimulation Be Useful in Spinal Cord Stimulation?" Medtronic, Inc., Minneapolis, MN, European Journal of Pain 13, 2009, 1 page.
Kumar et al., "Spinal Cord Stimulation in Treatment of Chronic Benign Pain: Challenges in Treatment Planning and Present Status, a 22-Year Experience," Neurosurgery, vol. 58, No. 3, Mar. 2006, 16 pages.
Kumar et al., "The Effects of Spinal Cord Stimulation in Neuropathic Pain Are Sustained: A 24-month Follow-Up of the Prospective Randomized Controlled Multicenter Trial of the Effectiveness of Spinal Cord Stimulation," www.neurosurgery-online.com, vol. 63, No. 4, Oct. 2008, 9 pages.
Lambru et al., "Safety and Efficacy of Cervical 10 KHz Spinal Cord Stimulation in Chronic Refractory Primary Headaches: A Retrospective Case Series," The Journal of Headache and Pain, 2016, 8 pages.
Lempka et al., "Computational Analysis of Kilohertz Frequency Spinal Cord Stimulation for Chronic Pain Management," Anesthesiology, vol. 122, No. 6, Jun. 2015, 15 pages.
Linderoth et al., "Mechanisms of Spinal Cord Stimulation in Neuropathic and Ischemic Pain Syndromes," Neuromodulation, Chapter 25, 2009, 19 pages.
Linderoth et al., "Mechanisms of Spinal Cord Stimulation in Painful Syndromes: Role of Animal Models," Pain Medicine, vol. 7, No. S1, 2006, 13 pages.
Linderoth et al., "Physiology of Spinal Cord Stimulation: Review and Update," Neuromodulation, vol. 2, No. 3, 1999, 15 pages.
MacDonald, Alexander J. R, and Coates, Tim W., "The Discovery of Transcutaneous Spinal Electroanalgesia and Its Relief of Chronic Pain," Physiotherapy, vol. 81. No. 11, Nov. 1995, 9 pages.
Manola et al., "Technical Performance of Percutaneous Leads for Spinal Cord Stimulation: A Modeling Study," International Neuromodulation Society, 2005, 12 pages.
Mavoori et al., "An Autonomous implantable computer for neural recording and stimulation in unrestrained primates," Journal of Neuroscience Methods, 2005, 7 pages.
McCreery et al., "Charge Density and Charge Per Phase as Cofactors in Neural Injury Induced by Electrical Stimulation," IEEE Transactions on Biomedical Engineering, vol. 37, No. 10, Oct. 1990.
McCreery et al., "Damage in Peripheral Nerve from Continuous Electrical Stimulation: Comparison of Two Stimulus Waveforms," Medical and Biological Engineering and Computing, Jan. 1992, 6 pages.
McCreery et al., "Relationship between Stimulus Amplitude, Stimulus Frequency and Neural Damage During Electrical Stimulation of Sciatic Nerve of a Cat," Medical and Biological Engineering and Computing, May 1995, 4 pages.
Mediati, R.D., "Mechanisms of Spinal Cord Stimulation," Florence, Oct. 2, 2002, 31 pages.

(56) References Cited

OTHER PUBLICATIONS

Medtronic—Neurological Division, QuadPlus, Model 3888, Lead Kit for Spinal Cord Stimulation (SCS) Implant Manual, 1996, 33 pages.
Medtronic—Neurological Division, Resume II, Model 3587A, Lead Kit for Spinal Cord Stimulation (SCS) and Peripheral Nerve Stimulation (PNS), Implant Manual, 1996, 32 pages.
Medtronic—Neurological Division, Resume TL, Model 3986, Lead Kit for Spinal Cord Stimulation (SCS) and Peripheral Nerve Stimulation (PNS), Implant Manual, 1996, 27 pages.
Medtronic—Neurostimulation Systems: Expanding the Array of Pain Control Solutions, 1999, 6 pages.
Medtronic commercial leaflet entitled: Surgical Lead Comparison, 1999, 4 pages.
Medtronic, "Medtronic Pain Therapy—Using Neurostimulation for Chronic Pain, Information for Prescribers" 2007, 29 pages.
Medtronic, Pain Therapy Product Guide, Dec. 2008, 31 pages.
Medtronic, Pisces Quad 3487A, Pisces Quad Compact model 3887, Pisces Quad Plus 3888 Lead Kit, Implant Manual, 2008, 16 pages.
Medtronic: Spinal Cord Stimulation Systems, 2013, 4 pages.
Melzack, Ronald et al., "Pain Mechanisms: A New Theory," Science, vol.; 150, No. 3699, Nov. 19, 1965, 9 pages.
Merriam Webster's Collegiate Dictionary, Tenth Edition, definition of "Implantable," 1995, 3 pages.
Meyerson et al., Mechanisms of spinal cord stimulation in neuropathic pain, Neurological Research, vol. 22, Apr. 2000, 5 pages.
Miller, Jonathan, "Neurosurgery Survival Guide—A Comprehensive Guide to Neurosurgical Diagnosis and Treatment," http://d3jonline.tripod.com/neurosurgery/, Nov. 14, 2016, 4 pages.
Miller, Jonathan, "Parameters of Spinal Cord Stimulation and Their Role in Electrical Charge Delivery: A Review," Neuromodulation: Technology at the Neural Interface, 2016, 12 pages.
Morgan Stanley Research North America, "Nevro Corp—There's Something Happening Here," Dec. 15, 2014, 12 pages.
Mosby's Medical Dictionary, 8th Edition, "Paresthesia," 2009, 3 pages.
Mounaïm et al., "New Neurostimulation Strategy and Corresponding Implantable Device to Enhance Bladder Functions," Biomedical Engineering Trends in Electronics, Communications and Software, Chapter 5, 2011, 15 pages.
Mueller et al., "The Med-El Sonatati 100 Cochlear Implant: An evaluation of its safety in adults and children," Acta Oto-Laryngologica, vol. 131, No. 5, 2011, 8 pages.
Muller and Hunsperger, "Helvetica Physiologica Acta—Reversible Blockierung der Erregungsleitung im Nerven durch Mittelfrequenz-Daverstrom," Schwabe & Co. Basel, vol. 25, Fasc. 1, 1967, 4 pages.
Munglani, Rajesh, "The Longer Term Effect of Pulsed Radiofrequency for Neuropathic Pain," Pain 80, 1999, 3 pages.
Nashold et al., "Dorsal Column Stimulation for Control Pain—Preliminary Report on 30 Patients," J. Neurosurg., vol. 36, May 1972, 8 pages.
Nevro—Chronic Pain and Treatments, http://www.nevro.com/English/Patients/Chronic-Pain-and-Treatments/default.aspx; 2016, 3 pages.
Nevro—Clinical Evidence, www.nevro.com/English/Physicians/Clinical-Evidence/default.aspx, 2016, 2 pages.
Nevro—HF10™ Therapy Fact Sheet, http://www.nevro.com/English/Newsroom/Resources/default.aspx, 2015, 4 pages.
Nevro—Leadership Through Innovation, J. P. Morgan 36th Annual Healthcare Conference, Jan. 8, 2018, 21 pages.
Nevro—Physician Overview www.nevro.com/English/Physicians/Physician-Overview/default.aspx, 2016, 5 pages.
Nevro—Senza System http://www.nevro.com/English/Physicians/Senza-System/default.aspx, 2016, 3 pages.
Nevro HF10 Therapy—New Hope for Chronic Back Pain and Leg Pain Sufferers, http://s21.q4cdn.com/478267292/files/doc_downloads/HF10-Therapy-New-Hope-for-Chronic-Pain.pdf, 2016, 2 pages.
Nevro Senza Patient Manual, Jan. 16, 2015, 53 pages.
Nevro Senza Physician Implant Manual, Jan. 16, 2015, 31 pages.
Nevro website: HF10 Therapy Advantages, www.nevro.com/English/Patients/HF10-Therapy-Advantages/default.aspx, 2016, 3 pages.
Nevro, PMA Approval Letter and Referenced Summary of Safety and Effectiveness Data (SSED) May 8, 2015, 60 pages.
Nevro's presentation of HF10 therapy on Nevro's website, http://www.nevro.com/English/Home/default.aspx, 2016, 2 pages.
News Release Details, "Nevro Corp. Announces Pricing of Initial Public Offering," 2014, 1 page.
NIDCD-NIH 2011, Cochlear Implant Brochure, http://www.nidcd.nih.gov/health/hearing/pages/coch.aspx, Jun. 29, 2012, 2 pages.
Non-Final Office Action for U.S. Appl. No. 12/765,747, First Named Inventor: Konstantinos Alataris, Mailed: Jul. 25, 2013, 7 pages.
Non-Final Office Acton for U.S. Appl. No. 13/245,450, First Named Inventor: Konstantinos Alataris, Mailed Nov. 18, 2011, 11 pages.
North American Neuromodulation Society—14th Annual Meeting, "Neuromodulation: Vision 2010," Dec. 2-5, 2010, 9 pages.
North American Neuromodulation Society—16th Annual Meeting, "From Innovation to Reality Syllabus," Dec. 6-9, 2012, 198 pages.
North American Neuromodulation Society—Celebrating 20 years, 18th Annual Meeting Program Book, Dec. 11-14, 2014, 28 pages.
North American Neuromodulation Society, "Today's Vision, Tomorrow's Reality—17th Annual Meeting," Dec. 5-8, 2013, 12 pages.
North American Neuromodulation, "15th Annual Meeting, Our Crystal Anniversary," Dec. 8-11, 2011, 8 pages.
North et al., "Failed Back Surgery Syndrome: 5-year Follow-Up after Spinal; Cord Stimulator Implantation," Neurosurgery, Official Journal of thogress of Neurological Surgeons, vol. 28, No. 5, May 1991, 9 pages.
North et al., "Spinal Cord Stimulation for Axial Low Back Pain," Spine, vol. 30, No. 12, 2005, 7 pages.
North et al., "Spinal Cord Stimulation for Chronic, Intractable Pain: Experience over Two Decades," Neurosurgery, vol. 32, No. 2, Mar. 1993, 12 pages.
North et al., "Spinal Cord Stimulation With Interleaved Pulses: A Randomized, Controlled Trial," vol. 10, No. 4, 2007, 9 pages.
Notice of Allowance for U.S. Appl. No. 13/245,450, First Named Inventor: Konstantinos Alataris, Mailed: Mar. 14, 2012, 8 pages.
Oakley et al., "A New Spinal Cord Stimulation System Effectively Relieves Chronic, Intractable Pain: A Multicenter Prospective Clinical Study," Neuromodulation: Technology at the Neural Interface, vol. 10, No. 3, 2007, 17 pages.
Oakley et al., "Spinal Cord Stimulation in Axial Low Back Pain: Solving the Dilemma," Pain Medicine, vol. 7, No. S1, 2006, 6 pages.
Oakley, John C., "Spinal Cord Stimulation Mechanisms of Action,"; Spine vol. 27, No. 22, copyright 2002, 10 pages.
OHSIPP Summer Newsletter, The Official Newsletter for the Ohio Society of Interventional Pain Physicians, vol. 1 Ed. 2, Summer 2010, 8 pages.
Paicius et al., "Peripheral Nerve Field Stimulation for the Treatment of Chronic Low Back Pain: Preliminary Results of Long-Term Follow-up: A Case Series," Neuromodulation: Technology at the Neural Interface, vol. 10, No. 3, 2007, 12 pages.
Palmer et al., "Transcutaneous electrical nerve stimulation and ; transcutaneous spinal electroanalgesia: A preliminary efficacy and mechanisms-based investigation," Physiotherapy, 95, 2009, 7 pages.
Partial European Search Report, European Application No. EP10160641, Applicant: Nevro Corporation, mailed Aug. 30, 2010, 3 pages.
Patent Owner's Preliminary Response for Inter Partes Review for U.S. Pat. No. 8,359,102, Case No. IPR2015-01203, Petitioner: *Boston Scientific Neuromodulation Corporation*, Patent Owner: *Nevro Corporation*, mailed Sep. 1, 2015, 70 pages.
Patent Owner's Preliminary Response for Inter Partes Review for U.S. Pat. No. 8,359,102, Case No. IPR2015-01204, Petitioner: *Boston Scientific Neuromodulation Corporation*, Patent Owner: *Nevro Corporation*, mailed Sep. 1, 2015, 63 pages.
Perruchoud et al., "Analgesic Efficacy of High-Frequency Spinal Cord Stimulation: A Randomized Double-Blind Placebo-Controlled Study," Neuromodulation: Technology at Neural Interface, International Neuromodulation Society, 2013, 7 pages.
Petition for Inter Partes Review of Claims 1, 2, 11-15, 17-23, 25 and 26 for U.S. Pat. No. 8,359,102, Petitioner: *Boston Scientific Neuromodulation Corporation*, Patent Owner: *Nevro Corporation*, May 14, 2015, 45 pages.

(56) References Cited

OTHER PUBLICATIONS

Petition for Inter Partes Review of Claims 1, 2, 11-15, 17-23, 25 and 26 for U.S. Pat. No. 8,359,102, Petitioner: *Boston Scientific Neuromodulation Corporation*, Patent Owner: *Nevro Corporation*, May 14, 2015, 67 pages.
Prausnitz et al., "The Effects of Electric Current Applied to Skin: A Review for Transdermal Drug Delivery," Advanced Drug Delivery Reviews 18, ; 1996, 31 pages.
Precision—Physician System Handbook, Advanced Bionic Corporation, Part 9055253-0001, 2005, 92 pages.
Precision—Physician Trail Kit Insert, Advanced Bionic Corporation, Part 9055258-0001, 2005, 2 pages.
Precision Spinal Cord Stimulation—Charging System Insert, Advanced Bionic Corporation, Part 9055074-0001, 2004, 2 pages.
Precision Spinal Cord Stimulation—Charging System, Advanced Bionic Corporation, Part 9055259-0001, 2004, 2 pages.
Precision Spinal Cord Stimulation—Patient System Handbook, Advanced Bionic Corporation, Part 9055072-0001, 2004, 93 pages.
Precision Spinal Cord Stimulation—Patient Trial Journal, Advanced Bionic Corporation, Part 9055260-0001, 2004, 10 pages.
Precision Spinal Cord Stimulation—Physician Implant Manual, Advanced Bionic Corporation, Part 9055255-0001, 2005, 70 pages.
Precision Spinal Cord Stimulation—Physician Implant Manual, Advanced Bionic Corporation, Part 9055100, 2004, 62 pages.
Precision Spinal Cord Stimulation—Physician Lead Manual, Advanced Bionic Corporation, Part No. 9055183-001, May 2004, 31 pages.
Precision Spinal Cord Stimulation—Physician Lead Manual, Advanced Bionic Corporation, Part 9055095, 2004, 62 pages.
Precision Spinal Cord Stimulation—Physician Lead Manual, Advanced Bionic Corporation, Part 9055256-0001, 2005, 56 pages.
Precision Spinal Cord Stimulation—Physician Trail Handbook, Advanced Bionic Corporation, Part 9055254-0001, 2005, 66 pages.
Precision Spinal Cord Stimulation—Physician Trail Kit Model SC-7005, Part 9055066-001, Advanced Bionic Corporation, 2004, 2 pages.
Precision Spinal Cord Stimulation—Remote Control Model SC-5200, Part 9055107-001, 2004, Advanced Bionic Corporation, 2 pages.
Precision Spinal Cord Stimulation—Remote Control Model SC-5210, Advanced Bionic Corporation, Part 9055257-001, 2005, 2 pages.
Precision Spinal Cord Stimulation System—Patient System Handbook, Advanced Bionic Corporation, Part No. 9055184-001, May 2004, 86 pages.
Precision Spinal Cord Stimulation System, Patient Trial Handbook, Part 9055078, 2004, 74 pages.
Pudenz et al., "Development of an Implantable Telestimulator," Proc. 4th Ann. Nat'l Conf. Neuroelectric Soc., Mar. 10-12, 1971, 111-12 (Wulfsohn, Norman L. and Anthony Sances, Jr. (eds.) 1971, 4 pages.
Pudenz et al., "Neural Stimulation: Clinical and Laboratory Experiences", Surg. Neurol, 39:235-242 (1993).
Rapcan et al., Clinical Study, "High-Frequency—Spinal Cord Stimulation," Indexed and Abstracted in Science Citation Index Expanded and in Journal Citation Reports, 2015, 3 pages.
Reddy et al., "Comparison of Conventional and Kilohertz Frequency Epidural Stimulation in Patients Undergoing Trailing for Spinal Cord Stimulation: Clinical Considerations," World Neurosurgery, www.sciencedirect.com, 6 pages, 2015.
Remedi Pain Relief—ENM (Electronic Nerve Modulation), https://web.archive.org/web/20050906181041/http://www.remediuk.com/trials.htm, 2005, 5 pages.
Renew Neurostimulation System—Clinician's Manual—Advanced Neuromodulation Systems, Life Gets Better, 2000, 77 pages.
Resume of Jason D. Rahn, Jan. 7, 2015, 2 pages.
Robb et al., "Transcutaneous Electrical Nerve Stimulation vs. Transcutaneous Spinal Electroanalgesia for Chronic Pain Associated with ; Breast Cancer Treatments," Journal of Pain and Symptom Management, vol. 33, No. 4, Apr. 2007, 10 pages.
Rosenblueth et al., "The Blocking and Deblocking Effects of Alternating Currents on Nerve," Department of Physiology in Harvard Medical School, Nov. 1938, 13 pages.

Royle, John., "Transcutaneous Spinal Electroanalgesia and Chronic Pain," Physiotherapy, vol. 86, No. 5, May 2000, 1 page.
Schulman et al., "Battery Powered BION FES Network," Proceedings of the 26th Annual Conference of the IEEE EMBS, San Francisco, CA., Sep. 1-5, 2004, 4 pages.
Science Daily, "Chronic Pain Costs U.S. up to $635 billion, study shows," www.sciencedaily.com/releases/2012/09/120911091100.htm, Sep. 11, 2012, 2 pages.
Senza Spinal Cord Stimulation (SCS) System—P130022, http://www.fda.gov/MedicalDevices/ProductsandMedicalProcedures/DeviceApprovalsandClearances/Recently-ApprovedDevices/ucm449963.htm Oct. 14, 2016, 2 pages.
Sharan et al., "Evolving Patterns of Spinal Cord Stimulation in Patients Implanted for Intractable Low Back and Leg Pain," International Neuromodulation Society, vol. 5, No. 3, 2002, 13 pages.
Shealy et al., "Dorsal Column Electrohypalgesia," Jul. 1969, 8 pages.
Shealy MD, C. Norman et al., "Electrical Inhibition of Pain by Stimulation of the Dorsal Columns: Preliminary Clinical Report," Anesthesia and Analgesia Current Researches, vol. 446, No. 4, Jul.-Aug. 1967, 3 pages.
Shelden et al., "Depolarization in the Treatment of Trigeminal Neuralgia," Evaluation of Compression and Electrical Methods, Clinical Concept of Neurophysiological Mechanism, 1966, 8 pages.
Shelden et al., "Development and Clinical Capabilities of a New Implantable Biostimulator," The American J. of Surgery, vol. 124, Aug. 1972, 6 pages.
Shelden et al., Electrical Control of Facial Pain, Am. J. of Surgery, vol. 114, Aug. 1967, 6 pages.
Shelden et al., "Electrical stimulation of the nervous system," Surg. Neurol. vol. 4, No. 1, Jul. 1975, 6 pages.
Simpson et al., "A Randomized, Double-Blind, Crossover Study of the Use of Transcutaneous Spinal Electroanalgesia in Patients with Pain from ; Chronic Critical Limb Ischemia," Journal of Pain and Symptom Management, vol. 28, No. 5, Nov. 2004, 6 pages.
Simpson, BA, "Spinal Cord Stimulation in 60 cases of Intractable Pain." Journal of Neurology, Neurosurgery and Psychiatry, 1991; 54 pp. 196-199.
Simpson, BA, "Spinal Cord Stimulation." British Journal of Neurosurgery, Feb. 11, 1997 (1), 5-11, 7 pages.
Sluijter et al., "The Effects of Pulsed Radiofrequency Fields Applied to the Dorsal Root Ganglion—A Preliminary Report," The Pain Clinic, vol. 11, No. 2, 1998, 12 pages.
Smet et al.,., "Successful Treatment of Low Back Pain with a Novel Neuromodulation Device," AZ Nikolaas, 12 pages.
Smet et al., Poster: "High-Frequency Spinal Cord Stimulation at 10 KHz after Failed Traditional Spinal Cord Stimulation," NANS, 2013, 1 page.
Solomonow et al., "Control of Muscle Contractile Force through Indirect High-Frequency Stimulation," AM Journal of Physical Medicine, 1983, vol. 62, No. 3, pp. 71-82.
St. Jude Medical, "Clinician's Manual—Percutaneous Lead Kit, Models 3143, 3146, 3149, 3153, 3156, 3159, 3183, 3186, 3189," 2016, 24 pages.
St. Jude Medical, "Eon Mini™ Rechargeable IPG," Apr. 29, 2013, 3 pages.
St. Jude Medical, "Individualized Therapy through Diverse Lead Options," 2008, 6 pages.
Stimwave, News Release: "Stimwave Receives FDA Approval for High Frequency IDE," http://stimwave.com/newsroom/latest-news, Jun. 9, 2015, 2 pages.
Struijk et al., "Recruitment of Dorsal Column Fibers in Spinal Cord Stimulation: Influence of Collateral Branching," IEEE Transactions on Biomedical Engineering, vol. 39, No. 9, Sep. 1992, 10 pages.
Summons to Attend Oral Proceedings pursuant to Rule 115(1) EPC for European Patent No. 2207587, Applicant: Nevro Corporation, mailed Mar. 9, 2018, 15 pages.
Sweet et al., "Paresthesia-Free High Density Spinal Cord Stimulation for Postlaminectomy Syndrome in a Prescreened Population: A Prospective Case Series," Neuromodulation: Technology at the Neural Interface, 2015, 7 pages.

(56) References Cited

OTHER PUBLICATIONS

Swigris et al., "Implantable Spinal Cord Stimulator to Treat the Ischemic Manifestations of Thromboangiitis Obliterans (Buerger's disease)," Journal of Vascular Surgery, vol. 29, No. 5, 1998, 8 pages.
Tan et al., "Intensity Modulation: A Novel Approach to Percept Control in Spinal Cord Stimulation," Neuromodulation Technology at the Neural Interface, International Neuromodulation Society 2015, 6 pages.
Tanner, J.A., "Reversible blocking of nerve conduction by alternating-current; excitation," Nature, 1962, Aug. 18; 195: 712-3.
Taylor et al., "The Cross Effectiveness of Spinal Cord Stimulation in the Treatment of Pain: A Systematic Review of the Literature," Journal of Pain and Symptom Management, vol. 27, No. 4., Apr. 2001, 9 pages.
Tesfaye et al., "Electrical Spinal Cord Stimulation for Painful Diabetic Peripheral Neuropathy," The Lancet, vol. 348, Dec. 21-28, 1996, 4 pages.
Thompson et al., "A double blind randomised controlled clinical trial on the effect of transcutaneous spinal electroanalgesia (TSE) on low back pain," European Journal of Pain, vol. 12, Issue 3, Apr. 2008, 6 pages.
Tiede et al., "Novel Spinal Cord Stimulation Parameters in Patients with Predominate Back Pain," Neuromodulation: Technology at the Neural Interface, 2013, 6 pages.
Tollison et al., "Practical Pain Management; Neurostimulation Techniques," Chapter 12, Lippincott Williams and Wilkins, Third Edition, 2002, 13 pages.
Towell et al., "High Frequency non-invasive stimulation over the spine: Effects on mood and mechanical pain tolerance in normal subjects," Behavioral Neurology, vol. 10, 1997, 6 pages.
Urban et al., "Percutaneous epidural stimulation of the spinal cord for relief of pain—Long Term Results," Journal of Neurosurgery, vol. 48, ; Mar. 1978, 7 pages.
Van Butyen et al., "High Frequency Spinal Cord Stimulation for the Treatment of Chronic Back Pain Patients: Results of a Prospective Multicenter European Clinical Study," Neuromodulation Technology at the ; Neural Interface, International Neuromodulation Society, 2012, 8 pages.
Van Buyten et al., "Pain Relief for Axial Back Pain Patients," INS Meeting Poster, 1 page.
Van Den Honert et al. "Generation of Unidirectionally Propagated Action Potentials Nerve by Brief Stimuli" Science, vol. 26, pp. 1311-1312.
Van Den Honert, Mortimer JT, "A Technique for Collision Block of Peripheral; Nerve: Frequency Dependence," MP-11 IEEE Trans. Biomed, Eng. 28: 379-382, 1981.
Van Havenbergh et al., "Spinal Cord Stimulation for the Treatment of Chronic Back Pain Patients: 500-Hz vs. 1000-Hz Burst Stimulation," Neuromodulation: Technology at the Neural Interface, International Neurmodulation Society, 2014, 4 pages.
Verrills et al., "Peripheral Nerve Field Stimulation for Chronic Pain: 100 Cases and Review of the Literature," Pain Medicine, 2011, 11 pages.
Verrills et al., "Salvaging Failed Neuromodulation Implants with Nevro High Frequency Spinal Cord System," NANS Poster, 2013, 1 page.
Von Korff et al., "Assessing Global Pain Severity by Self-Report in Clinical and Health Services Research," Spine, vol. 25, No. 24, 2000, 12 pages.
Wallace et al., Poster: "Accelerate: A Prospective Multicenter Trial Evaluating the Use of High-Rate Spinal Cord Stimulation in the Management of Chronic Intractable Pain," Boston Scientific Corporation, 2015, 1 page.
Ward et al., "Electrical Stimulation Using Kilohertz-Frequency Alternating Current," Journal of the American Physical Therapy Association, vol. 89, No. 2, Feb. 2009, 12 pages.
Ward et al., "Variation in Motor Threshold with Frequency Using KHz Frequency Alternating Current," Muscle and Nerve, Oct. 2001, 9 pages.

Webster's Third New International Dictionary of the English Language Unabridged, "Paresthesia," 1993, 3 pages.
Weinberg et al., "Increasing the oscillation frequency of strong magnetic fields above 101 kHz significantly raises peripheral nerve excitation thresholds," Medical Physics Letter, May 2012, 6 pages.
Wesselink et al., Analysis of Current Density and Related Parameters in Spinal Cord Stimulation, IEEE Transaction on Rehabilitation Engineering vol. 6, No. 2, Jun. 1998, 8 pages.
Wolter et al., "Continuous Versus Intermittent Spinal Cord Stimulation: An Analysis of Factors Influencing Clinical Efficacy," Neuromodulation: Technology at Neural Interface, www.neuromodulationjournal.com, 2011, 8 pages.
Woo MY, Campbell B. "Asynchronous Firing and Block of Peripheral Nerve Conduction by 20KC Alternating Current," Los Angeles Neuro Society, Jun. 1964; 87-94, 5 pages.
Yearwood et al., "A Prospective Comparison of Spinal Cord Stimulation (SCS) Using Dorsal Column Stimulation (DCS), Intraspinal Nerve Root Stimulation (INRS), and Varying Pulse Width in the Treatment of Chronic Low Back Pain," Congress of Neurological Surgeons 56th Annual Meeting, Oct. 7-12, 2006, 2 pages.
Yearwood et al., "Pulse Width Programming in Spinal Cord Stimulation: A Clinical Study," Pain Physician Journal, Jul./Aug. 2010, 16 pages.
Yearwood et al., Case Reports: "A Prospective Comparison of Spinal Cord Stimulation (SCS) Using Dorsal Column Stimulation (DCS), Intraspinal Nerve Root Stimulation (INRS), and Varying Pulse Width in the Treatment of Chronic Low Back Pain," Presented at the Congress of Neurological Surgeons 56th Annual Meeting, Oct. 7-12, 2006, 7 pages.
Zhang et al., "Simulation Analysis of Conduction Block in Myelinated Axons Induced by High-Frequency Biphasic Rectangular Pulses," IEEE Transactions on Biomedical Engineering, vol. 53., No. 7, Jul. 2006, 4 pages.
Zhang et al., Changes Across Time in Spike Rate and Spike Amplitude of Auditory Nerve Fibers Stimulated by Electric Pulse Trains, Journal of the Association for Research of Otolaryngology, 2007, 17 pages.
Non-Confidential Opening Brief of Appellant Stimwave Technologies, Inc. for Plaintiff-Appellee: *Nevro Corp* vs. Defendant-Appellant: *Stimwave Technologies, Inc.*, United States Court of Appeals for Federal Circuit, Case 19-CV-325, filed Sep. 24, 2019, 156 pages.
Principal and Response Brief for Defendants-Cross-Appellants Boston Scientific Corporation's and Boston Scientific Neuromodulation Corporation's, *Nevro Corp.* v. *Boston Scientific Corporation and Boston Scientific Neuromodulation Corporation*, Case No. 3:16-cv-06830-VC (N.D. Cal.), Jan. 17, 2019, 71 pages.
Reply Brief for Defendants-Cross-Appellants Boston Scientific Corporation's and Boston Scientific Neuromodulation Corporation's, *Nevro Corp.* v. *Boston Scientific Corporation and Boston Scientific Neuromodulation Corporation*, Case No. 3:16-cv-06830-VC (N.D. Cal.), Jun. 3, 2019, 26 pages.
Response and Reply Brief for Plaintiff-Appellant *Nevro Corp., Nevro Corp.* v. *Boston Scientific Corporation and Boston Scientific Neuromodulation Corporation*, Case No. 3:16-cv-06830-VC (N.D. Cal.), Apr. 12, 2019, 68 pages.
Memorandum Opinion, Plaintiff: *Nevro Corp.* vs. Defendant-Appellant: *Stimwave Technologies, Inc.*, United States Court for the District of Delaware, Civil Action No. 19-325-CFC, Case 19-CV-325, filed Jul. 24, 2019, 46 pages.
Medtronic's Response to the Summons to Attend Oral Proceedings for European Patent No. 2853285, *Nevro Corp.* vs. *Boston Scientific Neuromodulation Corporation and Medtronic, Inc.*, filed Nov. 30, 2018, 8 pages.
Boston Scientific's Response to the Summons to Attend Oral Proceedings for European Patent No. 2853285, *Nevro Corp.* vs. *Boston Scientific Neuromodulation Corporation and Medtronic, Inc*, filed Nov. 30, 2018, 5 pages.
Decision Rejecting the Opposition (Art. 101(2) EPC) for European Patent No. 2207587, *Nevro Corp.* vs. *Boston Scientific Neuromodulation Corporation and Medtronic, Inc.*, Jan. 4, 2019, 18 pages.

(56) References Cited

OTHER PUBLICATIONS

Provision of Minutes in accordance with Rule 124(4) EPC for Opposition by Medtronic, Inc., and Boston Scientific Neuromodulation Corporation for European Patent No. 2207587, mailed Jan. 4, 2019, 10 pages.
Medtronic's Submissions Commenting on the Auxiliary Requests for European Patent No. 2853285, *Nevro Corp.* vs. *Boston Scientific Neuromodulation Corporation and Medtronic, Inc*, filed Jan. 11, 2019, 13 pages.
Medtronic—Spinal Cord Stimulation (SCS) Patient Management Guidelines for Clinicians, 1999, 114 pages.
Nevro—Leadership Through Innovation, J. P. Morgan 36th Annual Healthcare Conference, Jan. 24, 2019, 2 pages.
Notice of Opposition for European Patent No. 3156099, Proprietor of the Patent: *Nevro Corporation*; Opponent: *Medtroni, Inc.*, Mar. 11, 2019, 31 pages.
Opponent Response to Patent Proprietor Comments to Declaration of Dr. Baranidharan for European Patent No. 2630984, mailed Nov. 8, 2016, 3 pages.
Opponents Medtronic, Inc.: Response to Grounds of Appeal for European Patent No. 2630984, mailed Dec. 19, 2017, 23 pages.
Opponents Boston Scientific Neuromodulation Corporation.: Statement Setting Out the Grounds of Appeal for European Patent No. 2207587, mailed May 2, 2019, 12 pages.
Opponents Medtronic, Inc.: Statement Setting Out the Grounds of Appeal for European Patent No. 2207587, mailed May 19, 2019, 21 pages.
Non-Final Office Action for U.S. Appl. No. 16/048,138, Applicant: Nevro Corp., issued Sep. 24, 2018, 7 pages.
Response to Non-Final Office Action for U.S. Appl. No. 16/048,138, Applicant: Nevro Corp., filed Dec. 21, 2018, 5 pages.
Final Office Action for U.S. Appl. No. 16/048,138, Applicant: Nevro Corp., issued Feb. 28, 2019, 6 pages.
Response to Final Office Action for U.S. Appl. No. 16/048,138, Applicant: Nevro Corp., filed May 28, 2019, 9 pages.
Non-Final Office Action for U.S. Appl. No. 16/048,148, Applicant: Nevro Corp., issued Oct. 4, 2018, 7pages.
Response to Non-Final Office Action for U.S. Appl. No. 16/048,148, Applicant: Nevro Corp., filed Dec. 21, 2018, 5 pages.
Final Office Action for U.S. Appl. No. 16/048,148, Applicant: Nevro Corp., issued Apr. 19, 2019, 7 pages.
Response to Final Office Action for U.S. Appl. No. 16/048,148, Applicant: Nevro Corp., filed May 28, 2019, 6 pages.
Patentee: Nevro Corporation reply to Statement Grounds of Appeal in Support to the Notice of Appeal on May 17, 2019 for European Patent No. 2853285, mailed Aug. 9, 2019, 24 pages.
Patentee: Nevro Corporation reply to Summons to Oral Proceedings for European Patent No. 2853285, mailed Nov. 30, 2018, 6 pages.
Provision of the Minutes in accordance with Rule 124(4) EPC, *Nevro Corp.* vs. *Boston Scientific Neuromodulation Corporation and Medtronic, Inc.*, for European Patent No. 2853285, mailed Apr. 1, 2019, 10 pages.
Decision Revoking for European Patent (Art. 101(2) and 101(3)(b) EPC) for European Patent No. 2853285, *Nevro Corp.* vs. *Boston Scientific Neuromodulation Corporation and Medtronic, Inc.*, mailed Apr. 1, 2019, 54 pages.
Patentee: *Nevro Corporation* reply to Notice of Opposition filed by *Boston Science Neuromodulation* on May 9, 2022 and Medtronic, Inc., on Mar. 3, 2019 for European Patent No. 3156099, mailed Aug. 7, 2019, 104 pages.
Reply of the Patent Proprietor, Nevro Corporation for European Patent No. 2207587, Opponent 1: *Medtronic, Inc.*, and Opponent 2: *Boston Scientific Neuromodulation Corporation*, mailed Sep. 25, 2019.
Summons to Attend Oral Proceedings pursuant to Rule 115(1) EPC for European Patent No. 3156099, Applicant: Nevro Corporation, mailed Nov. 22, 2019, 21 pages.
Siegel et al., "Prospective Randomized Feasibility Study Assessing the Effect of Cyclic Sacral Neuromodulation on Urinary Urge Incontinence in Women," Female Pelvic Med Reconstr Surg. 2018, 5 pages.
Cadish, "Stimulation Latency and Comparison of Cycling Regimens in Women Using Sacral Neuromodulation," Feb. 1, 2016, 4 pages.
Hofmann et al., "Modified Pulse Shapes for Effective Neural Stimulation," Frontiers in Neuroengineering, Sep. 28, 2011, 10 pages.
Cappaert et al., "Efficacy of a New Charge-Balanced Biphasic Electrical Stimulus in the Isolated Sciatic Nerve and the Hippocampal Slice," International Journal of Neural Systems, vol. 23, No. 1, 2013, 16 pages.
Milligan et al., "Pathological and Protective Roles of Glia in Chronic Pain," Nat Rev Neurosci. 2009, pages.
Vallejo et al., "The Role of Glia and the Immune System in the Development and Maintenance of Neuropathic Pain," Pain Pract. 2010, pages.
De Leo et al., "The Tetrapartite Synapse: Path to CNS centralization and Chronic Pain," Pain. 2006, pages.

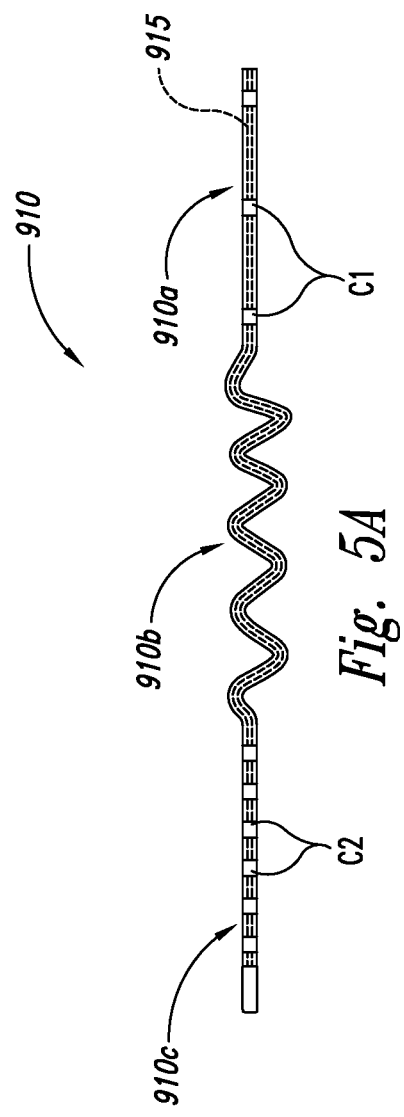
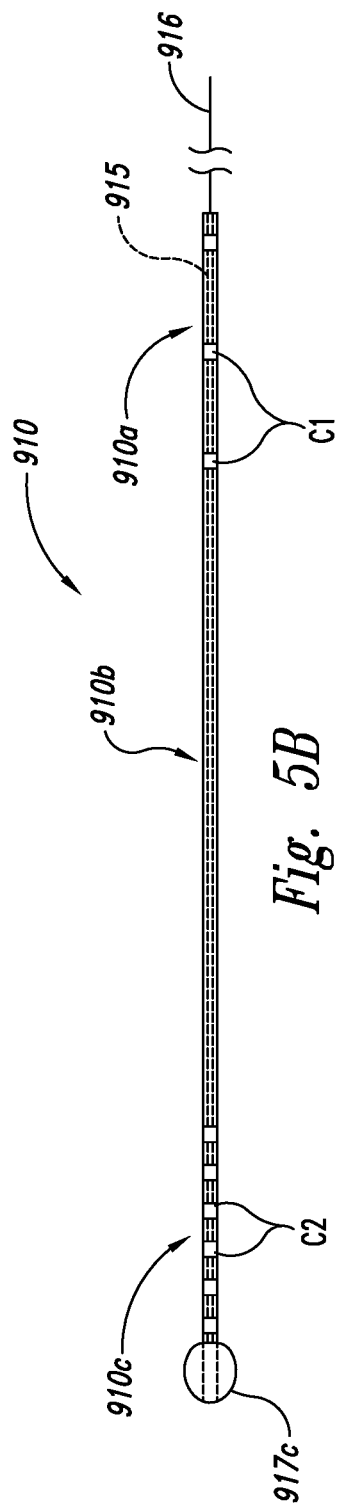
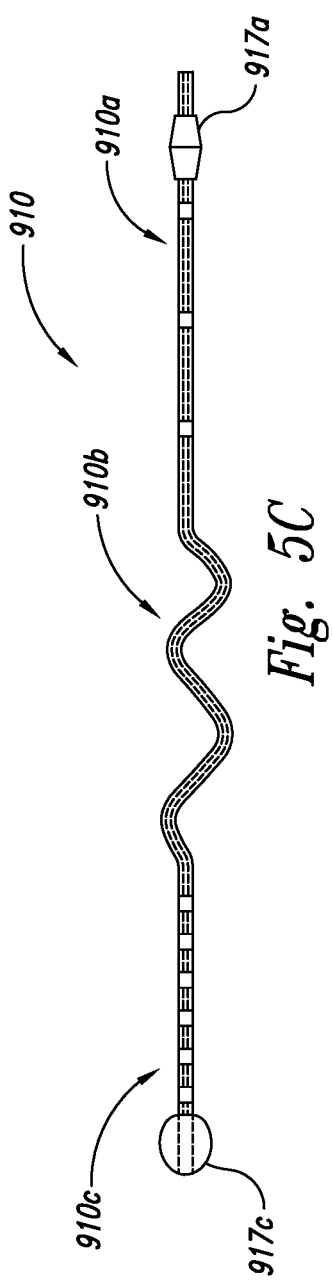

SPINAL CORD MODULATION FOR INHIBITING PAIN VIA SHORT PULSE WIDTH WAVEFORMS, AND ASSOCIATED SYSTEMS AND METHODS

CROSS-REFERENCE TO RELATED APPLICATIONS

The present application is a continuation of U.S. patent application Ser. No. 16/781,960, filled Feb. 4, 2020, which is a continuation of U.S. patent application Ser. No. 16/048,131, filed Jul. 27, 2018, which is a divisional of U.S. patent application Ser. No. 14/534,769, filed on Nov. 6, 2014, which claims priority to U.S. Provisional Application No. 61/901,255, filed on Nov. 7, 2013, incorporated herein by reference.

TECHNICAL FIELD

The present disclosure is directed generally to spinal cord modulation for inhibiting pain via short pulse width waveforms, and associated systems and methods.

BACKGROUND

Neurological stimulators have been developed to treat pain, movement disorders, functional disorders, spasticity, cancer, cardiac disorders, and various other medical conditions. Implantable neurological stimulation systems generally have an implantable pulse generator and one or more leads that deliver electrical pulses to neurological tissue via electrodes. For example, neurological stimulation systems for spinal cord stimulation (SCS) may include cylindrical leads that include a lead body with a circular cross-sectional shape and one or more conductive rings spaced apart from each other at the distal end of the lead body. The conductive rings operate as individual electrodes and, in many cases, the SCS leads are implanted percutaneously through a large needle inserted into the epidural space, with or without the assistance of a stylet.

Once implanted, the pulse generator applies electrical pulses to the neurological tissue via the electrodes, which in turn modifies the function of the patient's nervous system. Conventional SCS pain treatments, for example, apply low-frequency (e.g., less than 1,500 Hz), large pulse width (e.g., greater than 50 microsecond) electrical pulses to the spinal cord to generate sensations of tingling or paresthesia that mask or otherwise alter the patient's sensation of pain. In some cases, patients report that the generated sensations of tingling or paresthesia are perceived as more pleasant and/or less uncomfortable than the underlying pain sensation. Studies have suggested (at least anecdotally) that longer pulse width electrical pulses (e.g., in excess of 450 microseconds) achieve better pain-paresthesia overlap and comfort for patients (Lee et al., Predicted effects of pulse width programming in spinal cord stimulation: a mathematical modeling study, Med Biol Eng Comput (2011) 49:765-774).

BRIEF DESCRIPTION OF THE DRAWINGS

FIGS. 5A-5C are partially schematic illustrations of extendible leads configured in accordance with several embodiments of the disclosure.

DETAILED DESCRIPTION

1.0 Introduction

The present technology is directed generally to spinal cord modulation and associated systems and methods for inhibiting pain via waveforms with short pulse widths (e.g., less than 50 microseconds). In at least some embodiments, the waveforms also have frequencies (and/or frequency elements or components, e.g., fundamental frequencies) in the range of from about 2 Hz to about 1,500 Hz. In general, the short pulse width characteristics of the signal, alone or in combination with other signal parameters (e.g., frequency and/or amplitude) can produce pain relief without using the generation of paresthesia to mask the patient's sensation of pain. Several embodiments also provide simplified spinal cord modulation systems and components, and simplified procedures for the practitioner and/or the patient. Specific details of certain embodiments of the disclosure are described below with reference to methods for modulating one or more target neural populations (e.g., nerves) or sites of a patient, and associated implantable structures for providing the modulation. Although selected embodiments are described below with reference to modulating the dorsal column, dorsal horn, dorsal root, dorsal root entry zone, and/or other particular regions of the spinal column to control pain, the modulation may in some instances be directed to other neurological structures and/or target neural populations of the spinal cord and/or other neurological tissues. Some embodiments can have configurations, components or procedures different than those described in this section, and other embodiments may eliminate particular components or procedures. A person of ordinary skill in the relevant art, therefore, will understand that the disclosure may include other embodiments with additional elements, and/or may include other embodiments without several of the features shown and described below with reference to FIGS. 1A-6C.

In general terms, aspects of many of the following embodiments are directed to producing a therapeutic effect that includes pain reduction in the patient. The therapeutic effect can be produced by inhibiting, suppressing, downregulating, preventing, or otherwise modulating the activity of the affected neural population. In many embodiments of the presently disclosed techniques, therapy-induced paresthesia is not a prerequisite to achieving pain reduction.

Figure 1A:
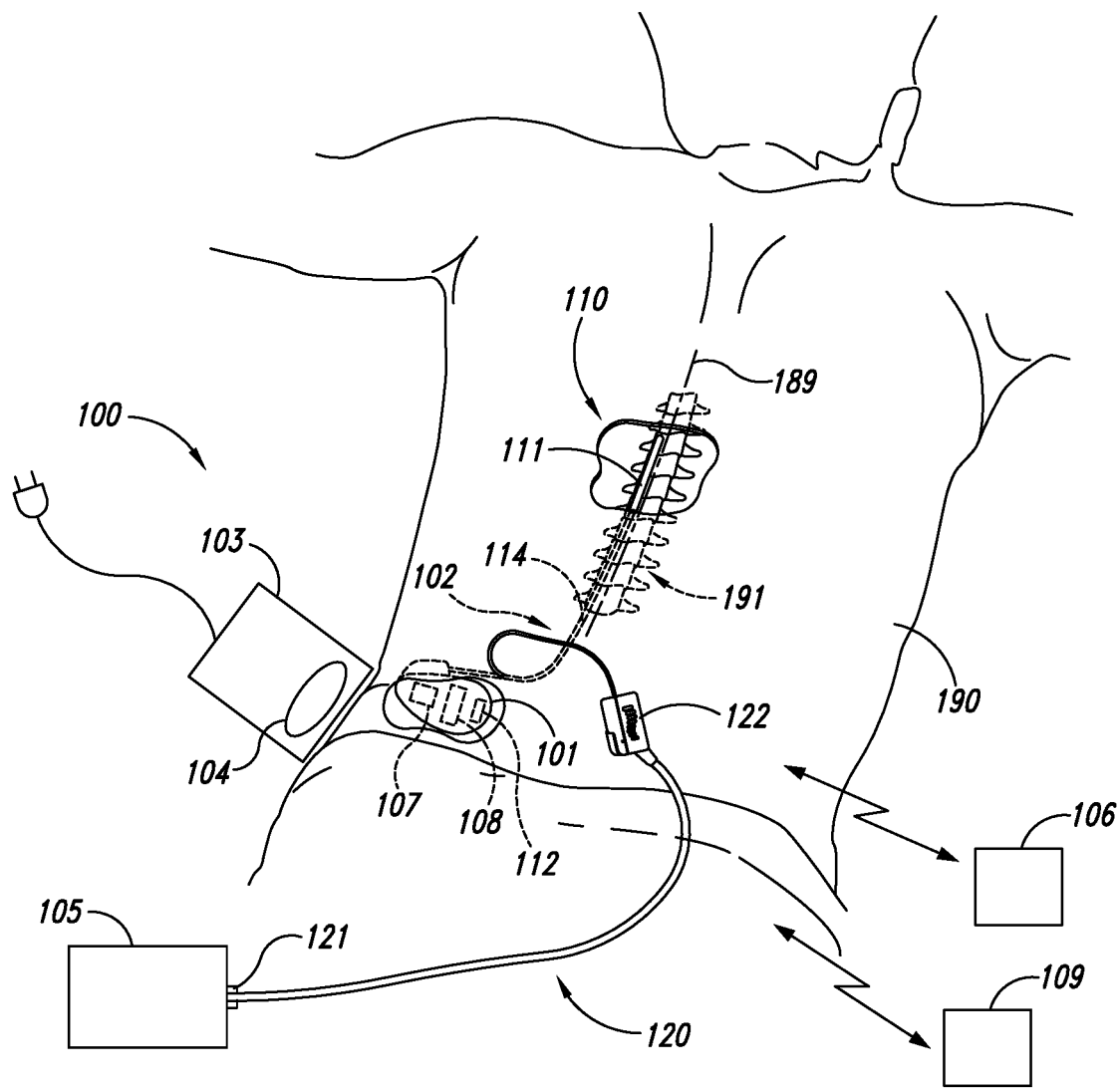
FIG. 1A is a partially schematic illustration of an implantable spinal cord modulation system positioned at the spine to deliver therapeutic signals in accordance with several embodiments of the present disclosure.

FIG. 1A schematically illustrates a representative treatment system 100 for providing relief from chronic pain and/or other conditions, arranged relative to the general anatomy of a patient's spinal cord 191. The system 100 can include an implantable pulse generator 101, which may be implanted subcutaneously within a patient 190 and may be coupled to a signal delivery element 110. In a representative example, the signal delivery element 110 includes a lead or lead body 111 that carries features for delivering therapy to the patient 190 after implantation. The pulse generator 101 can be connected directly to the lead 111, or it can be coupled to the lead 111 via a communication link 102 (e.g., an extension). Accordingly, the lead 111 can include a terminal section that is releasably connected to an extension at a break 114 (shown schematically in FIG. 1A). This allows a single type of terminal section to be used with patients of different body types (e.g., different heights). As used herein, the terms lead and lead body include any of a number of suitable substrates and/or support members that carry devices for providing therapy signals to the patient 190. For example, the lead 111 can include one or more electrodes or electrical contacts that direct electrical signals into the patient's tissue, such as to provide for patient relief. In other embodiments, the signal delivery element 110 can include devices other than a lead body (e.g., a paddle, a leadless implantable electrode, etc.) that also direct electrical signals and/or other types of signals to the patient 190.

The pulse generator 101 can transmit signals (e.g., electrical signals) to the signal delivery element 110 that up-regulate (e.g., stimulate or excite) and/or down-regulate (e.g., inhibit or suppress) target nerves. As used herein, and unless otherwise noted, the terms "modulate" and "modulation" refer generally to signals that have either type of the foregoing effects on the target nerves. The pulse generator 101 can include a machine-readable (e.g., computer-readable) medium containing instructions for generating and transmitting suitable therapy signals in accordance with the methods and/or parameters described herein. The pulse generator 101 and/or other elements of the system 100 can include one or more processors 107, memories 108 and/or input/output devices. Accordingly, the process of providing modulation signals and/or executing other associated functions can be performed by computer-executable instructions contained on computer-readable media, e.g., at the processor(s) 107 and/or memory(s) 108. The pulse generator 101 can include multiple portions, elements, and/or subsystems (e.g., for directing signals in accordance with multiple signal delivery parameters, housed in a single housing, as shown in FIG. 1A, or in multiple housings.

The pulse generator 101 can also receive and respond to an input signal received from one or more sources. The input signals can direct or influence the manner in which the therapy instructions are selected, executed, updated and/or otherwise performed. The input signal can be received from one or more sensors 112 (one is shown schematically in FIG. 1 for purposes of illustration) that are carried by the pulse generator 101 and/or distributed outside the pulse generator 101 (e.g., at other patient locations) while still communicating with the pulse generator 101. The sensors 112 can provide inputs that depend on or reflect patient state (e.g., patient position, patient posture and/or patient activity level), and/or inputs that are patient-independent (e.g., time). In other embodiments, inputs can be provided by the patient and/or the practitioner, as described in further detail later.

In some embodiments, the pulse generator 101 can obtain power to generate the therapy signals from an external power source 103. The external power source 103 can transmit power to the implanted pulse generator 101 using electromagnetic induction (e.g., RF signals). For example, the external power source 103 can include an external coil 104 that communicates with a corresponding internal coil (not shown) within the implantable pulse generator 101. The external power source 103 can be portable for ease of use.

In another embodiment, the pulse generator 101 can obtain the power to generate therapy signals from an internal power source, in addition to or in lieu of the external power source 103. For example, the implanted pulse generator 101 can include a non-rechargeable battery or a rechargeable battery to provide such power. When the internal power source includes a rechargeable battery, the external power source 103 can be used to recharge the battery. The external power source 103 can in turn be recharged from a suitable power source (e.g., conventional wall power).

In some cases, a trial modulator 105 can be coupled to the signal delivery element 110 during an initial implant procedure, prior to implanting the pulse generator 101. For example, a practitioner (e.g., a physician and/or a company representative) can use the trial modulator 105 to vary the modulation parameters provided to the signal delivery element 110 in real time, and select optimal or particularly efficacious parameters. These parameters can include the position of the signal delivery element 110, as well as the characteristics of the electrical signals provided to the signal delivery element 110. In a typical process, the practitioner uses a cable assembly 120 to temporarily connect the trial modulator 105 to the signal delivery device 110. The cable assembly 120 can accordingly include a first connector 121 that is releasably connected to the trial modulator 105, and a second connector 122 that is releasably connected to the signal delivery element 110. Accordingly, the signal delivery element 110 can include a connection element that allows it to be connected to a signal generator either directly (if it is long enough) or indirectly (if it is not). The practitioner can test the efficacy of the signal delivery element 110 in an initial position. The practitioner can then disconnect the cable assembly 120, reposition the signal delivery element 110, and reapply the electrical modulation. This process can be performed iteratively until the practitioner obtains the desired position for the signal delivery device 110. Optionally, the practitioner may move the partially implanted signal delivery element 110 without disconnecting the cable assembly 120.

After the position of the signal delivery element 110 and appropriate signal delivery parameters are established using the trial modulator 105, the patient 190 can receive therapy via signals generated by the trial modulator 105, generally for a limited period of time. In a representative application, the patient 190 receives such therapy for one week. During this time, the patient wears the cable assembly 120 and the trial modulator 105 outside the body. Assuming the trial therapy is effective or shows the promise of being effective, the practitioner then replaces the trial modulator 105 with the implanted pulse generator 101, and programs the pulse generator 101 with parameters selected based on the experience gained during the trial period. Optionally, the practitioner can also replace the signal delivery element 110. Once the implantable pulse generator 101 has been positioned within the patient 190, the signal delivery parameters provided by the pulse generator 101 can still be updated remotely via a wireless external programmer 109 (e.g., a physician's remote, laptop, PDA, tablet, etc.) and/or a wireless patient programmer 106 (e.g., a patient remote). Generally, the patient 190 has control over fewer parameters than does the practitioner. For example, the capability of the patient programmer 106 may be limited to only starting and/or stopping the pulse generator 101, and/or adjusting the signal amplitude.

In any of the foregoing embodiments, the parameters in accordance with which the pulse generator 101 provides signals can be adjusted during portions of the therapy regimen. For example, the frequency, amplitude, pulse width and/or signal delivery location can be adjusted in accordance with a preset program, patient and/or physician inputs, and/or in a random or pseudorandom manner. Such parameter variations can be used to address a number of potential clinical situations, including changes in the patient's perception of pain, changes in the preferred target neural population, and/or patient accommodation or habituation.

2.0 Representative Therapy Parameters

Figure 1B:
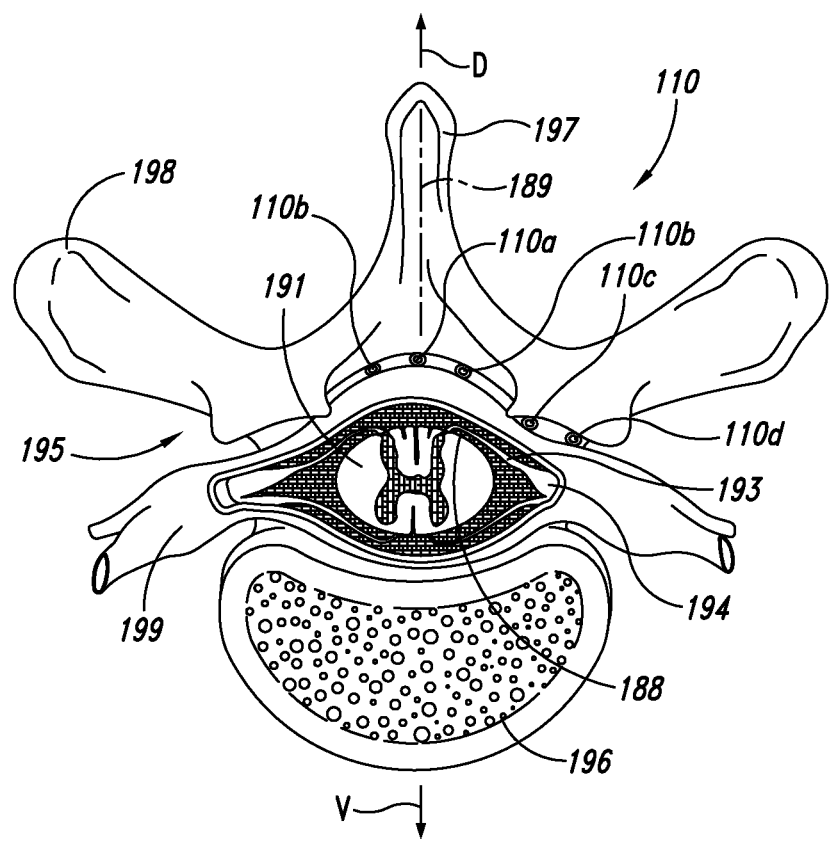
FIG. 1B is a partially schematic, cross-sectional illustration of a patient's spine, illustrating representative locations for implanted lead bodies in accordance with embodiments of the disclosure.

FIG. 1B is a cross-sectional illustration of the spinal cord 191 and an adjacent vertebra 195 (based generally on information from Crossman and Neary, "Neuroanatomy," 1995 (published by Churchill Livingstone)), along with the locations at which leads 110 can be implanted in representative patients. The spinal cord 191 is situated between a ventrally located ventral body 196 and the dorsally located transverse process 198 and spinous process 197. Arrows V and D identify the ventral and dorsal directions, respectively. The spinal cord 191 itself is located within the dura mater 199, which also surrounds portions of the nerves exiting the spinal cord 191, including the dorsal roots 193, dorsal root entry zone 188, and dorsal root ganglia 194. The leads 110 (indicated by leads 110b) can be positioned just off the spinal cord midline 189 (e.g., about 1 mm. offset) in opposing lateral directions so that the two leads 110b are spaced apart from each other by about 2 mm, in particular embodiments. In other embodiments, a single lead 110a can be positioned at the midline 189. In still further embodiments, lead(s) can be positioned at or proximate to the dorsal root 193 (as shown by lead 110c) and/or at or proximate to the dorsal root ganglia 194 (as shown by lead 110d).

Figure 2A:
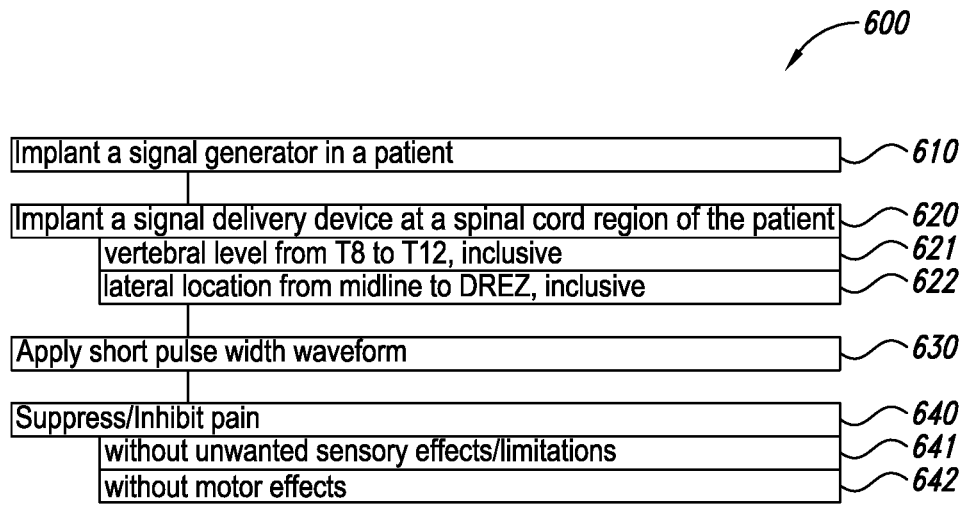
FIGS. 2A and 2B are flow diagrams illustrating methods conducted in accordance with embodiments of the disclosure.
Figure 2B:
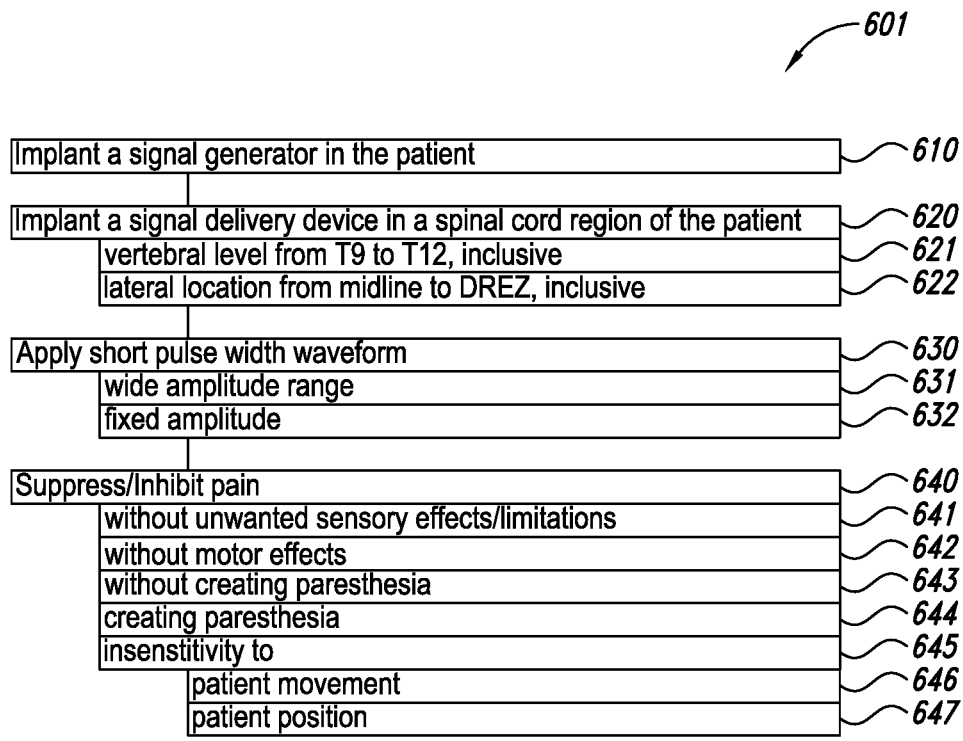

FIGS. 2A and 2B are flow diagrams illustrating methods for treating patients in accordance with particular embodiments of the present disclosure. Manufacturers or other suitable entities can provide instructions to practitioners for executing these and other methods disclosed herein. Manufacturers can also program devices of the disclosed systems to carry out at least some of these methods. FIG. 2A illustrates a method 600 that includes implanting a signal generator in a patient (block 610). The signal generator can be implanted at the patient's lower back or other suitable location. The method 600 further includes implanting a signal delivery device (e.g., a lead, paddle or other suitable device) at the patient's spinal cord region (block 620). This portion of the method can in turn include implanting the device (e.g., active contacts of the device) at a vertebral level ranging from about T8 to about T12 (e.g., about T8-T12, inclusive) (block 621), and at a lateral location ranging from the spinal cord midline to the DREZ, inclusive (block 622). At block 630, the method includes applying a short pulse width waveform, via the signal generator and the signal delivery device. In particular examples, the signal (or at least a portion of the signal) can have pulses with pulse widths ranging from about 10-50 microseconds, or from about 20-40 microseconds, or from about 25-35 microseconds, or from about 30-35 microseconds, or about 30 microseconds. The amplitude of the waveform (e.g., the amplitudes of the individual pulses) can be from about 0.5-20 mA, or from about 2-18 mA, or from about 5-15 mA, or from about 7-10 mA, or about 0.5-7 mA. The frequency of the signal (or at least a portion of the signal) can be at or below 1.5 kHz, e.g., from about 2 Hz to about 1.5 kHz, or from about 500 Hz to about 1.5 kHz, or from about 700 Hz to about 1.5 kHz, or from about 1 kHz to about 1.5 kHz, or about 1.2 kHz, or from about 500 Hz to about 1.2 kHz. In one representative example, the waveform includes a frequency of 1,200 Hz, a pulse width of 30 microseconds, and an amplitude that provides pain relief without generating paresthesia (generally between 0.5-20 mA).

The method 600 further includes suppressing, inhibiting or otherwise reducing the patient's pain, e.g., chronic low back pain (block 640). This portion of the method can in turn include reducing pain without unwanted sensory effects and/or limitations (block 641), and/or without motor effects (block 642). For example, block 641 can include reducing or eliminating pain without reducing patient perception of other sensations, and/or without triggering additional pain and/or paresthesia. Block 642 can include reducing or eliminating pain without triggering muscle action and/or without interfering with motor signal transmission.

FIG. 2B illustrates a method 601 that includes features in addition to those described above with reference to FIG. 2A. For example, the process of applying a short pulse width waveform (block 630) can include doing so over a wide amplitude range (e.g., over any of the amplitude ranges described immediately above) without creating unwanted side effects, such as undesirable sensations and/or motor interference (block 631). In another embodiment, the process of applying a short pulse width waveform can include applying the waveform at a fixed amplitude (block 632).

The process of inhibiting, suppressing or otherwise reducing patient pain (block 640) can include doing so without creating paresthesia (block 643), or in association with a deliberately generated paresthesia (block 644). For example, paresthesia may be used by the practitioner for site selection (e.g., to determine the location at which active electrodes are positioned). In addition to the above, reducing patient pain can include doing so with relative insensitivity to patient attributes that standard SCS is normally highly sensitive to (block 645). These attributes can include patient movement (block 646) and/or patient position (block 647).

Figure 2C:
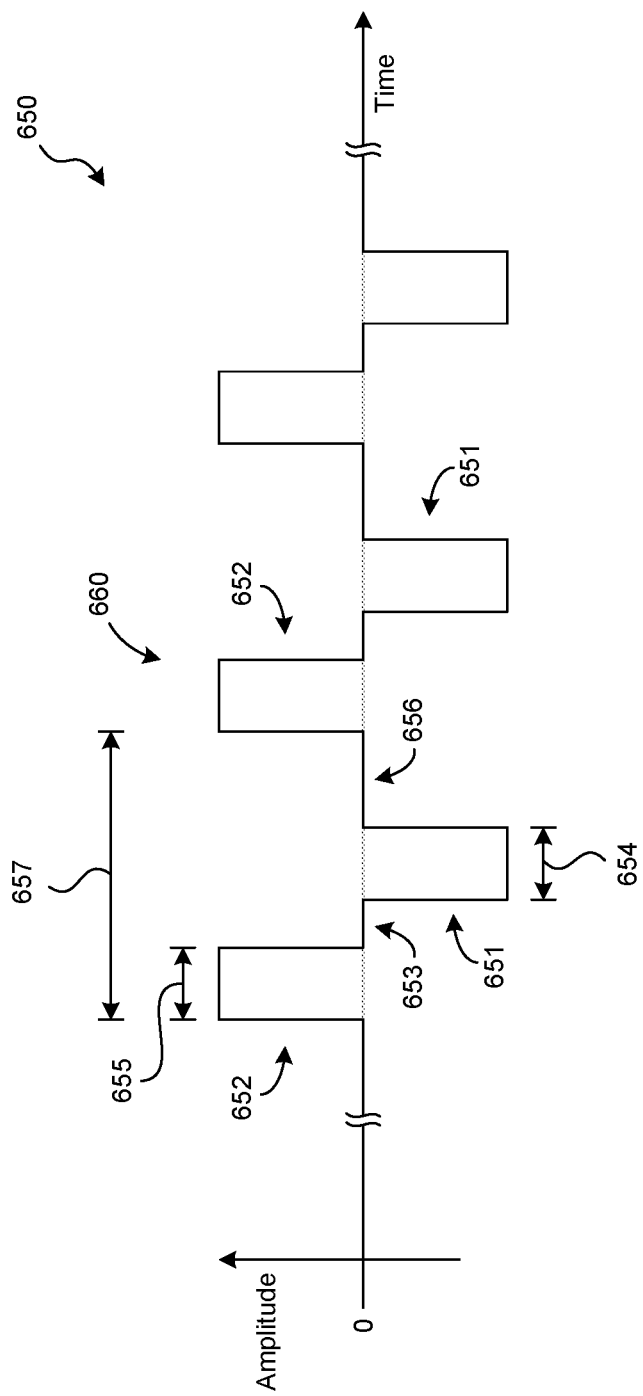
FIG. 2C is a schematic illustration of a representative waveform having features in accordance with embodiments of the present technology.

FIG. 2C illustrates a representative waveform 650 having pulses 660 and other characteristics, parameters and/or features in accordance with representative embodiments of the present technology. The pulses 660 can include cathodic phase pulses 651 paired with anodic phase pulses 652. The cathodic phase pulses 651 can be separated from the anodic phase pulses 652 by an interphase interval 653. A pulse pair interval 656 can separate one pulse pair (e.g., a cathodic phase pulse 651 paired with an anodic phase pulse 652) from the next. The frequency of the waveform 650 is generally defined as the inverse of the period 657. The period 657 is in turn the sum of a cathodic phase pulse width 654, an anodic phase pulse width 655, the interphase interval 653 and the pulse pair interval 656.

The values described above with reference to FIG. 2A for pulse width can apply to the cathodic phase pulse width 654 and/or the anodic phase pulse width 655. The cathodic and anodic phase pulse widths 654, 655 are equal in some embodiments, and unequal in others. In general, the area enclosed by the cathodic phase pulses 651 and the anodic phase pulses 652, as shown in FIG. 2C, can be equal. Accordingly, the overall charge applied to the patient as a result of the cathodic phase pulses 651 can be equal and opposite to the overall charge applied to the patient as a result of the anodic phase pulses 652. This charge balancing approach can reduce or eliminate potential adverse effects associated with charge accumulation within the patient.

In general, e.g., when the cathodic and anodic pulse widths 654, 655 are equal, the amplitudes of the cathodic phase pulses 651 and the anodic phase pulses 652 are also equal, but in at least some embodiments, the amplitudes can be different. For example, when the pulse widths of the cathodic phase pulses 651 are different than those of the anodic phase pulses 652, the respective amplitudes of the pulses can also be different, and can be selected to balance the overall charge applied to the patient.

In particular embodiments, the interphase interval 653 can have a value of from about 10 microseconds to about 980 milliseconds. The pulse pair interval 656 can have a value in the range of from about 10 microseconds to about 980 milliseconds. In at least some embodiments, the value of pulse pair interval 656 results from the selection of the cathodic phase pulse width 654, the anodic phase pulse width 655, the interphase interval 653 and the period 657. In other embodiments, the pulse pair interval 656 can be selected first with other parameters (e.g., the interphase interval 653) being secondary. In still further embodiments, the parameters can be selected in other orders, with the pulse width(s) (anodic and/or cathodic) generally being an independent variable.

Figure 3:
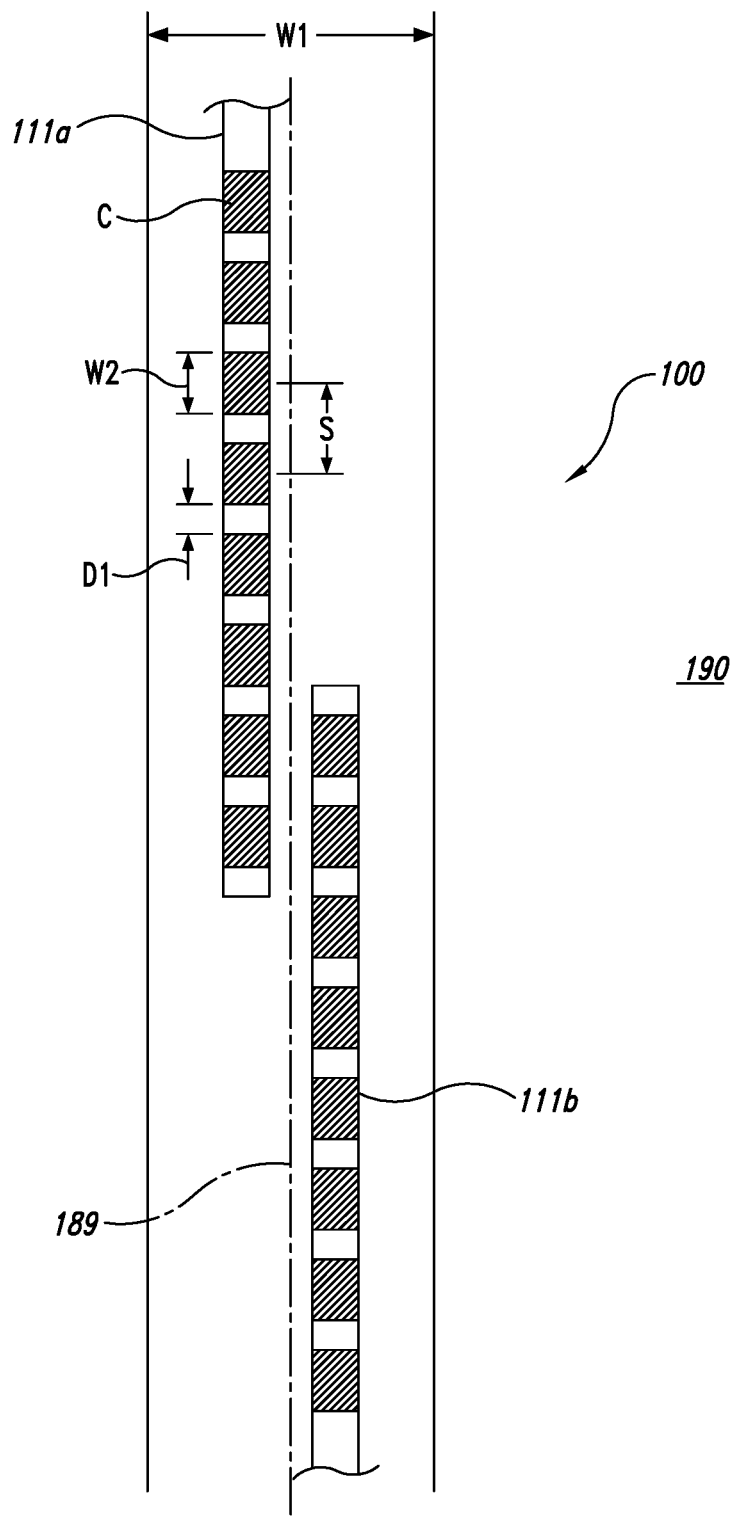
FIG. 3 illustrates an arrangement of leads.

FIG. 3 is a schematic illustration of a typical lead placement used during a representative treatment regimen. Two leads 111 (shown as a first lead 111a and a second lead 111b) can be positioned generally end-to-end to provide a modulation capability that extends over several vertebral levels of the patients' spine. The leads 111a, 111b can be positioned to overlap slightly, to account for possible shifts in lead location. During the course of the therapy, contacts C of the two leads 111a, 111b can be activated on one lead at a time. In other words, the contacts C of only one lead 111 can be active at any one time, and signals need not directed between the contacts C located on different leads 111. While two leads can be used is some cases, it is expected that in other cases, a single lead can be positioned at the appropriate vertebral level. The lead can have more widely spaced contacts to achieve the same or similar effects as those described herein as will be described in greater detail below with reference to FIG. 4.

The contacts C of each lead 111a, 111b have a width W2 of approximately 3 mm, and are separated from each other by a distance D1 of approximately 1 mm. Accordingly, the center-to-center spacing S between neighboring contacts C is approximately 4 mm. The leads 111a, 111b can be positioned at or close to the patients' spinal midline 189. In a representative embodiment one lead can be positioned on one side of the midline 189, and the other lead can be positioned on the other side of the patients' midline 189. The leads 111a, 111b can be positioned at any of a variety of locations within a relatively wide window W1 having an overall width of +3-5 mm from the midline 189 (e.g., an overall width of 6-10 mm), without significantly affecting the efficacy of the treatment.

In one embodiment, one or more of the above-described waveform parameters and lead placements are used to produce an incomplete conduction block (e.g., an incomplete block of afferent and/or efferent signal transmission) at the dorsal root level. This block may occur at the dorsal column, dorsal horn, and/or dorsal root entry zone, in addition to or in lieu of the dorsal root. In any of these cases, the conduction block is selective to and/or preferentially affects the smaller Aδ and/or C fibers and is expected to produce a decrease in excitatory inputs to the second order neurons, thus producing a decrease in pain signals supplied along the spinal thalamic tract.

In another embodiment, one or more of the above-described waveform parameters and lead placements are used to activate an interneuron pool and thus increase the inhibition of inputs into second order neurons. This activation can, in effect, desensitize the second order neurons and convert them closer to a normal state before the effects of the chronic pain associated signals have an effect on the patient.

In still another embodiment, one or more of the above-described waveform parameters and lead placements are used to reduce the hypersensitivity of neurons by restoring or moving the "baseline" of the neural cells in chronic pain patients toward the normal baseline and firing frequency of non-chronic pain patients. This effect can in turn reduce the sensation of pain in this patient population without affecting other neural transmissions (for example, touch, heat, etc.).

In another embodiment, one or more of the above-described waveform parameters and lead placements are used to (1) reduce neural transmissions entering the spinal cord at the dorsal root and/or the dorsal root entry zone, and/or (2) reduce neural activity at the dorsal horn itself. It is generally known that chronic pain patients may be in a state of prolonged sensory sensitization at both the nociceptive afferent neurons (e.g., a peripheral nerve and its associated dorsal root) and at higher order neural systems (e.g., the dorsal horn neuron). It is also known that the dorsal horn neurons (e.g., the width dynamic range or WDR cells) are sensitized in chronic pain states. Chronic pain can be associated with an acute "windup" of the WDR cells (e.g., to a hyperactive state). It is believed that the therapy signals applied using the disclosed parameters may be used to reduce pain by reducing, suppressing, and/or attenuating the afferent nociceptive inputs delivered to the WDR cells, as it is expected that these inputs, unless attenuated, can be responsible for the sensitized state of the WDR cells. In one embodiment, the disclosed parameters may be used to act directly on the WDR cells to desensitize these cells. The effect of the presently disclosed therapy on peripheral inputs may produce short term pain relief, and the effect on the WDR cells may produce longer term pain relief.

In one embodiment, one or more of the above-described waveform parameters and lead placements are used to modulate glial cells in the nervous system. Glial cells were traditionally thought to play primarily a structural role in the nervous system, for example by surrounding neurons, holding neurons in place, providing electrical insulation, and destroying pathogens. However, in recent years it has been suggested that glial cells play a role in the transmission of chronic pain by releasing various mediators such as nitric oxide, pro-inflammatory cytokines, excitatory amino acids, and prostaglandins. Release of these mediators can cause the release of substance P and excitatory amino acids by peripheral nerves, which in turn results in action potential generation. Substance P and excitatory amino acid release can also further activate glial cells, creating a positive feedback loop. Glial cells communicate via slow inward calcium currents, which are activated by a variety of factors including potassium. The short pulse width waveform parameters disclosed herein may be used to reduce extracellular potassium levels by primary afferent inhibition, thereby reducing glial cell activity. The short pulse width waveform parameters disclosed herein may also be used to produce pain reduction in part by changing the conductance of fast sodium channels in neurons and/or glial cells, thereby specifically down-regulating those sodium channels that are most involved with chronic pain.

As disclosed herein, short pulse width electrical modulation can be used to normalize pathological neural networks associated with fast sodium channel activity and/or expression by attenuating pathology-induced sodium channel activity and modulating glial neuronal cell interaction (GNI). Based on this, the present application provides methods and devices for attenuating pathology-induced sodium channel activity, modulating GNI, and treating various conditions associated with fast sodium channel activity and/or expression and GNI.

In certain embodiments, methods are provided for attenuating pathology-induced sodium channel activity by applying short pulse width electrical stimulation to a target tissue or organ (e.g., the spinal cord). This attenuation may result in decreased activity and/or expression of one or more fast sodium channels, including for example NaV1.8 or NaV1.9. In certain embodiments, decreased activity and/or expression of one or more fast sodium channels results in decreased glial cell and/or neuronal activity. In certain embodiments, attenuation of pathology-induced sodium channel activity may also result in increased activity and/or expression of one or more slow sodium channels, including for example NaV1.3.

4.0 Expected Benefits Associated With Certain Embodiments

As discussed above, an expected benefit of short pulse width waveforms (e.g., having pulse widths within the ranges described above) is that when applied at the appropriate amplitude, to the appropriate neural population, such pulses can effectively reduce or eliminate patient pain without the signal producing, creating, or generating paresthesia. In addition to providing pain relief without paresthesia, such waveforms can produce pain relief with less power than is required for waveforms having longer pulse widths, depending upon the values selected for other signal delivery parameters.

In any of the foregoing embodiments, aspects of the therapy provided to the patient may be varied within or outside the parameters described above, while still obtaining beneficial results for patients suffering from chronic pain (e.g., chronic lower back pain, chronic leg pain, chronic limb pain, etc.). For example, the location of the lead body (and in particular, the lead body electrodes or contacts) can be varied over the significant lateral and/or axial ranges described above. Other characteristics of the applied signal can also be varied. For example, the frequency of the signal (or at least a portion of the signal) can be at or below 1.5 kHz, e.g., from about 2 Hz to about 1.5 kHz, or from about 500 Hz to about 1.5 kHz, or from about 700 Hz to about 1.5 kHz, or from about 1 kHz to about 1.5 kHz, or about 1.2 kHz, or from about 500 Hz to about 1.2 kHz. The amplitude of the signal can range from about 0.1 mA to about 20 mA in a particular embodiment, and in further particular embodiments, can range from about 0.5 mA to about 10 mA, or about 0.5 mA to about 7 mA, or about 0.5 mA to about 5 mA. The amplitude of the applied signal can be ramped up and/or down. In particular embodiments, the amplitude can be increased or set at an initial level to establish a therapeutic effect, and then reduced to a lower level to save power without forsaking efficacy. In particular embodiments, the signal amplitude refers to the electrical current level, e.g., for current-controlled systems. In other embodiments, the signal amplitude can refer to the electrical voltage level, e.g., for voltage-controlled systems. In particular embodiments, the signal (or at least a portion of the signal) can have pulses with pulse widths ranging from about 10-50 microseconds, or from about 20-40 microseconds, or from about 25-35 microseconds, or from about 30-35 microseconds, or about 30 microseconds. The specific values selected for the foregoing parameters may vary from patient to patient and/or from indication to indication and/or on the basis of the selected vertebral location. In addition, the methodology may make use of other parameters, in addition to or in lieu of those described above, to monitor and/or control patient therapy. For example, in cases for which the pulse generator includes a constant voltage arrangement rather than a constant current arrangement, the current values described above may be replaced with corresponding voltage values. In another example, it is expected that the signal can have short pulse widths over a wide range of frequencies while producing pain relief without paresthesia. For example, pulse widths of 10-50 microseconds may be used to produce such results at frequencies ranging from about 2 Hz to about 1,500 Hz.

Patients can receive multiple signals in accordance with still further embodiments of the disclosure. For example, patients can receive two or more signals, each with different signal delivery parameters. In one particular example, the signals are interleaved with each other. In other embodiments, patients can receive sequential "packets" or "bursts" of pulses at different frequencies, with each packet having a duration of less than one second, several seconds, several minutes, or longer depending upon the particular patient and indication.

In still further embodiments, the duty cycle can be from about 50%-100%. In further embodiments, the duty cycle can have a value of less than 50%, e.g., at or less than 20% or at or less than 10%. In yet another embodiment, the duty cycle parameters can be set to 2 seconds on, 20 seconds off. In still further embodiments, the duty cycle parameters can be set to 20 seconds on, 120 seconds off.

5.0 Representative Lead Configurations

Figure 4:
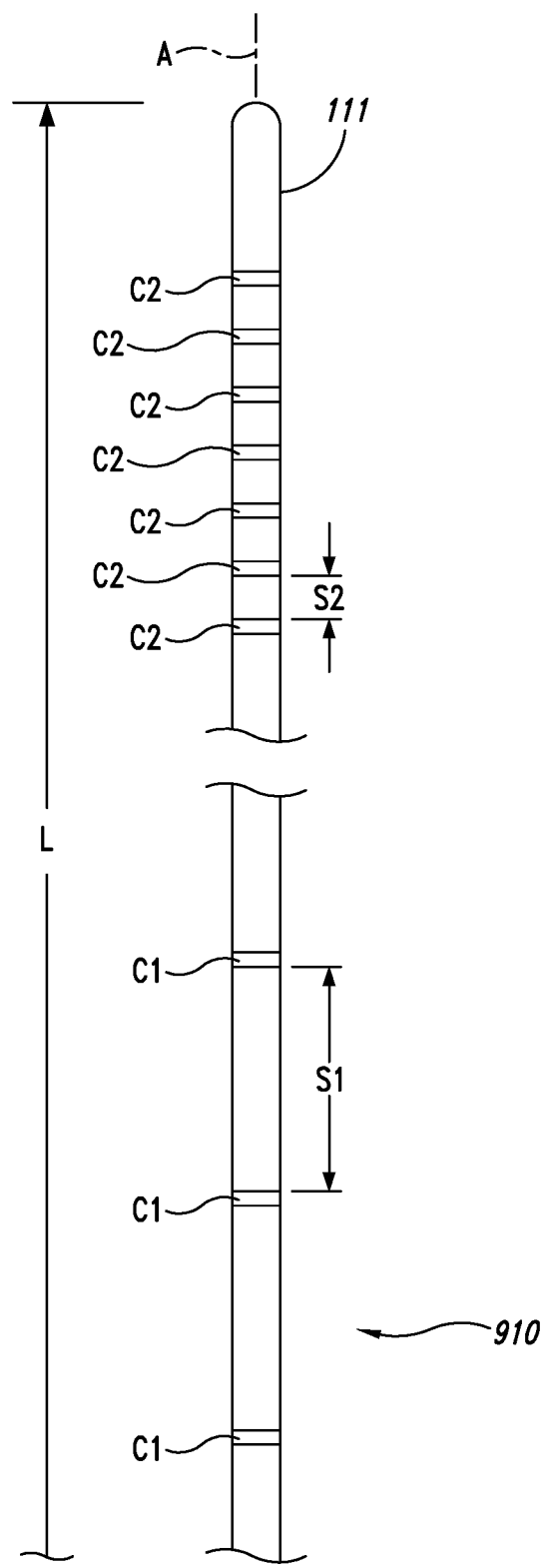
FIG. 4 is a partially schematic illustration of a lead body configured in accordance with an embodiment of the disclosure.

FIG. 4 is a partially schematic illustration of a lead 910 having first and second contacts C1, C2 positioned to deliver modulation signals in accordance with particular embodiments of the disclosure. The contacts are accordingly positioned to contact the patient's tissue when implanted. The lead 910 can include at least two first contacts C1 and at least two second contacts C2 to support bipolar modulation signals via each contact grouping. In one aspect of this embodiment, the lead 910 can be elongated along a major or lead axis A, with the contacts C1, C2 spaced equally from the major axis A. In general, the term elongated refers to a lead or other signal delivery element having a length (e.g., along the spinal cord) greater than its width. The lead 910 can have an overall length L (over which active contacts are positioned) that is longer than that of typical leads. In particular, the length L can be sufficient to position first contacts C1 at one or more vertebral locations (including associated neural populations), and position the second contacts C2 at another vertebral location (including associated neural populations) that is spaced apart from the first and that is superior the first. For example, the first contacts C1 may be positioned at vertebral levels T8-T12 to treat low back pain, and the second contacts C2 may be positioned at superior vertebral locations (e.g., cervical locations) to treat arm pain. Representative lead lengths are from about 30 cm to about 150 cm, and in particular embodiments, from about 40 cm to about 50 cm. Pulses may be applied to both groups of contacts in accordance with several different arrangements. For example pulses provided to one group may be interleaved with pulses applied to the other, or the same signal may be rapidly switched from one group to the other. In other embodiments, the signals applied to individual contacts, pairs of contacts, and/or contacts in different groups may be multiplexed in other manners. In any of these embodiments, each of the contacts C1, C2 can have an appropriately selected surface area, e.g., in the range of from about 3 mm$^2$ to about 25 mm$^2$, and in particular embodiments, from about 8 mm$^2$ to about 15 mm$^2$. Individual contacts on a given lead can have different surface area values, within the foregoing ranges, than neighboring or other contacts of the lead, with values selected depending upon features including the vertebral location of the individual contact.

Another aspect of an embodiment of the lead 910 shown in FIG. 4 is that the first contacts C1 can be spaced apart (e.g., closest edge to closest edge) by a first distance S1 that is greater than a corresponding second distance S2 between immediately neighboring second contacts C2. In a representative embodiment, the first distance S1 can range from about 3 mm up to a distance that corresponds to one-half of a vertebral body, one vertebral body, or two vertebral bodies (e.g., about 16 mm, 32 mm, or 64 mm, respectively). In another particular embodiment, the first distance S1 can be from about 5 mm to about 15 mm. This increased spacing can reduce the complexity of the lead 910, and can still provide effective treatment to the patient. In still further embodiments, the inferior first contacts C1 can have the close spacing S2, and the superior second contacts C2 can have the wide spacing S1, depending upon patient indications and/or preferences. In still further embodiments, as noted above, contacts at both the inferior and superior locations can have the wide spacing. In other embodiments, the lead 910 can include other arrangements of different contact spacings, depending upon the particular patient and indication. For example, the widths of the second contacts C2 (and/or the first contacts C1) can be a greater fraction of the spacing between neighboring contacts than is represented schematically in FIG. 4. The distance S1 between neighboring first contacts C1 can be less than an entire vertebral body (e.g., 5 mm or 16 mm) or greater than one vertebral body while still achieving benefits associated with increased spacing, e.g., reduced complexity. The lead 910 can have all contacts spaced equally (e.g., by up to about two vertebral bodies), or the contacts can have different spacings, as described above. Two or more first contacts C1 can apply modulation at one vertebral level (e.g., T9) while two or more additional first contacts C1 can provide modulation at the same or a different frequency at a different vertebral level (e.g., T10).

In some cases, it may be desirable to adjust the distance between the inferior contacts C1 and the superior contacts C2. For example, the lead 910 can have a coil arrangement (like a telephone cord) or other length-adjusting feature that allows the practitioner to selectively vary the distance between the sets of contacts. In a particular aspect of this arrangement, the coiled portion of the lead can be located between the first contacts C1 and the second contacts C2. For example, in an embodiment shown in FIG. 5A, the lead 910 can include a proximal portion 910a carrying the first contacts C1, a distal portion 910c carrying the second contacts C2, and an intermediate portion 910b having a pre-shaped, variable-length strain relief feature, for example, a sinusoidally-shaped or a helically-shaped feature. The lead 910 also includes a stylet channel or lumen 915 extending through the lead 910 from the proximal portion 910a to the distal portion 910c.

Referring next to FIG. 5B, the practitioner inserts a stylet 916 into the stylet lumen 915, which straightens the lead 910 for implantation. The practitioner then inserts the lead 910 into the patient, via the stylet 916, until the distal portion 910c and the associated second contacts C2 are at the desired location. The practitioner then secures the distal portion 910c relative to the patient with a distal lead device 917c. The distal lead device 917c can include any of a variety of suitable remotely deployable structures for securing the lead, including, but not limited to an expandable balloon.

Referring next to FIG. 5C, the practitioner can partially or completely remove the stylet 916 and allow the properties of the lead 910 (e.g., the natural tendency of the intermediate portion 910b to assume its initial shape) to draw the proximal portion 910a toward the distal portion 910c. When the proximal portion 910a has the desired spacing relative to the distal portion 910c, the practitioner can secure the proximal portion 910a relative to the patient with a proximal lead device 917a (e.g., a suture or other lead anchor). In this manner, the practitioner can select an appropriate spacing between the first contacts C1 at the proximal portion 910a and the second contacts C2 at distal portion 910c that provides effective treatment at multiple patient locations along the spine.

Figure 6A:
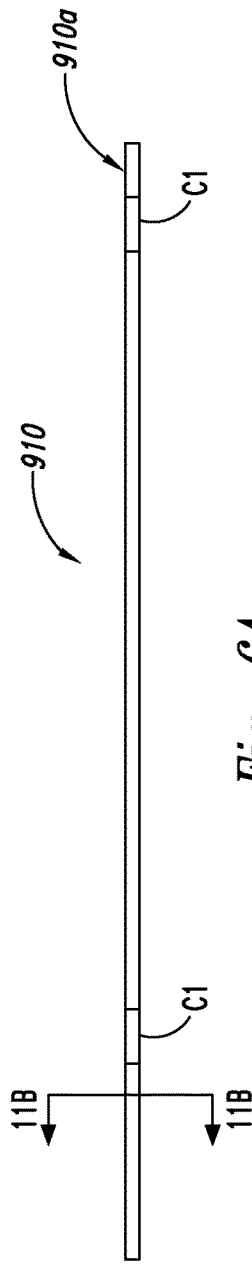
FIGS. 6A-6C are partially schematic illustrations of multifilar leads configured in accordance with several embodiments of the disclosure.
Figure 6B:
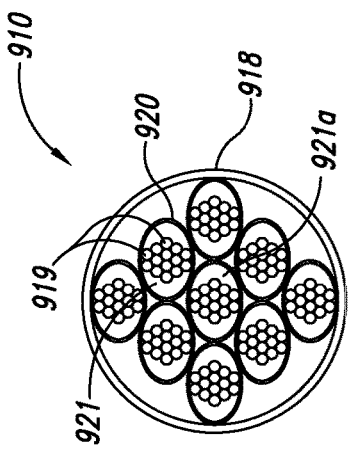

FIG. 6A is an enlarged view of the proximal portion 910a of the lead 910, illustrating an internal arrangement in accordance with a particular embodiment of the disclosure. FIG. 6B is a cross-sectional view of the lead 910 taken substantially along line 11B-11B of FIG. 6A. Referring now to FIG. 6B, the lead 910 can include multiple conductors 921 arranged within an outer insulation element 918, for example, a plastic sleeve. In a particular embodiment, the conductors 921 can include a central conductor 921a. In another embodiment, the central conductor 921a can be eliminated and replaced with the stylet lumen 915 described above. In any of these embodiments, each individual conductor 921 can include multiple conductor strands 919 (e.g., a multifilar arrangement) surrounded by an individual conductor insulation element 920. During manufacture, selected portions of the outer insulation 918 and the individual conductor insulation elements 920 can be removed, thus exposing individual conductors 921 at selected positions along the length of the lead 910. These exposed portions can themselves function as contacts, and accordingly can provide modulation to the patient. In another embodiment, ring (or cylinder) contacts are attached to the exposed portions, e.g., by crimping or welding. The manufacturer can customize the lead 910 by spacing the removed sections of the outer insulation element 918 and the conductor insulation elements 920 in a particular manner. For example, the manufacturer can use a stencil or other arrangement to guide the removal process, which can include, but is not limited to, an ablative process. This arrangement allows the same overall configuration of the lead 910 to be used for a variety of applications and patients without major changes. In another aspect of this embodiment, each of the conductors 921 can extend parallel to the others along the major axis of the lead 910 within the outer insulation 918, as opposed to a braided or coiled arrangement. In addition, each of the conductor strands 919 of an individual conductor element 920 can extend parallel to its neighbors, also without spiraling. It is expected that these features, alone or in combination, will increase the flexibility of the overall lead 910, allowing it to be inserted with a greater level of versatility and/or into a greater variety of patient anatomies then conventional leads.

Figure 6C:
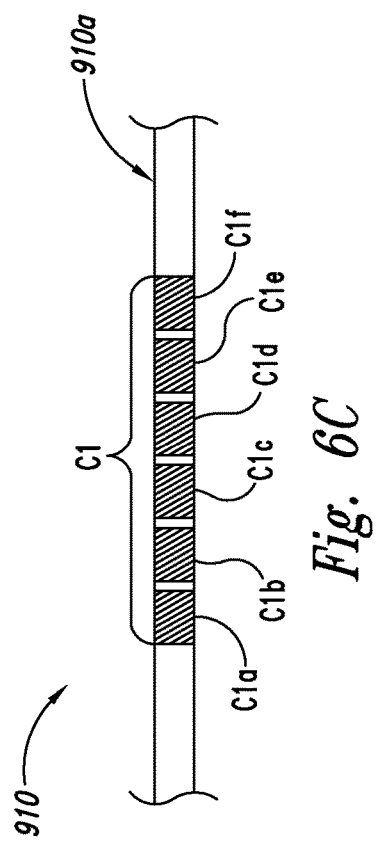

FIG. 6C is a partially schematic, enlarged illustration of the proximal portion 910a shown in FIG. 6A. One expected advantage of the multifilar cable described above with reference to FIG. 6B is that the impedance of each of the conductors 921 can be reduced when compared to conventional coil conductors. As a result, the diameter of the conductors 921 can be reduced and the overall diameter of the lead 910 can also be reduced. One result of advantageously reducing the lead diameter is that the contacts C1 may have a greater length in order to provide the required surface area needed for effective modulation. If the contacts C1 are formed from exposed portions of the conductors 921, this is not expected to present an issue. If the contacts C1 are ring or cylindrical contacts, then in particular embodiments, the length of the contact may become so great that it inhibits the practitioner's ability to readily maneuver the lead 910 during patient insertion. One approach to addressing this potential issue is to divide a particular contact C1 into multiple sub-contacts, shown in FIG. 6C as six sub-contacts C1a-C1f. In this embodiment, each of the individual sub-contacts C1a-C1f can be connected to the same conductor 921 shown in FIG. 6B. Accordingly, the group of sub-contacts connected to a given conductor 921 can operate essentially as one long contact, without inhibiting the flexibility of the lead 910.

As noted above, one feature of the foregoing arrangements is that they can be easy to design and manufacture. For example, the manufacturer can use different stencils to provide different contact spacings, depending upon specific patient applications. In addition to or in lieu of the foregoing effect, the foregoing arrangement can provide for greater maneuverability and facilitate the implantation process by eliminating ring electrodes and/or other rigid contacts, or dividing the contacts into subcontacts. In other embodiments, other arrangements can be used to provide contact flexibility. For example, the contacts can be formed from a conductive silicone, e.g., silicone impregnated with a suitable loading of conductive material, such as platinum, iridium or another noble metal.

Yet another feature of an embodiment of the lead shown in FIG. 4 is that a patient can receive effective therapy with just a single bipolar pair of active contacts. If more than one pair of contacts is active, each pair of contacts can receive the identical waveform, so that active contacts can be shorted to each other. In another embodiment, the implanted pulse generator (not visible in FIG. 4) can serve as a return electrode. For example, the pulse generator can include a housing that serves as the return electrode, or the pulse generator can otherwise carry a return electrode that has a fixed position relative to the pulse generator. Accordingly, the modulation provided by the active contacts can be unipolar modulation, as opposed to the more typical bipolar stimulation associated with standard SCS treatments.

6.0 Representative Modulation Locations and Indications

Many of the embodiments described above were described in the context of treating chronic, neuropathic low back pain with modulation signals applied to the lower thoracic vertebrae (T8-T12). In other embodiments, modulation signals having parameters (e.g., frequency, pulse width, amplitude, and/or duty cycle) generally similar to those described above can be applied to other patient locations to address other indications. For example, while the foregoing methodologies included applying modulation at lateral locations ranging from the spinal cord midline to the DREZ, in other embodiments, the modulation may be applied to the foramen region, laterally outward from the DREZ. In other embodiments, the modulation may be applied to other spinal levels of the patient. For example, modulation may be applied to the sacral region and more particularly, the "horse tail" region at which the sacral nerves enter the sacrum. Urinary incontinence and fecal incontinence represent example indications that are expected to be treatable with modulation applied at this location. In other embodiments, the modulation may be applied to other thoracic vertebrae. For example, modulation may be applied to thoracic vertebrae above T8. In a particular embodiment, modulation may be applied to the T3-T6 region to treat angina. Modulation can be applied to high thoracic vertebrae to treat pain associated with shingles. Modulation may be applied to the cervical vertebrae to address chronic regional pain syndrome and/or total body pain, and may be used to replace neck surgery. Suitable cervical locations include vertebral levels C3-C7, inclusive. In other embodiments, modulation may be applied to the occipital nerves, for example, to address migraine headaches.

As described above, modulation in accordance with the foregoing parameters may also be applied to treat acute and/or chronic nociceptive pain. For example, modulation in accordance with these parameters can be used during surgery to supplement and/or replace anesthetics (e.g., a spinal tap). Such applications may be used for tumor removal, knee surgery, and/or other surgical techniques. Similar techniques may be used with an implanted device to address post-operative pain, and can avoid the need for topical lidocaine. In still further embodiments, modulation in accordance with the foregoing parameters can be used to address other peripheral nerves. For example, modulation can be applied directly to peripheral nerves to address phantom limb pain.

From the foregoing, it will be appreciated that specific embodiments of the disclosure have been described herein for purposes of illustration, but that various modifications may be made without deviating from the disclosure. For example, the specific parameter ranges and indications described above may be different in further embodiments. The lead described above with reference to FIGS. 4-6C can have more than two groups of contacts, and/or can have other contact spacings in other embodiments. In some embodiments, as described above, the signal amplitude applied to the patient can be constant. In other embodiments, the amplitude can vary in a preselected manner, e.g., via ramping up/down, and/or cycling among multiple amplitudes. The signal delivery elements can have an epidural location, as discussed above with regard to FIG. 1B, and in other embodiments, can have an extradural location. In particular embodiments described above, signals having the foregoing characteristics are expected to provide therapeutic benefits for patients having low back pain and/or leg pain, when stimulation is applied at vertebral levels from about T8 to about T12. In at least some other embodiments, it is believed that this range can extend from about T5 to about L1.

Certain aspects of the disclosure described in the context of particular embodiments may be combined or eliminated in other embodiments. For example, therapies directed to particular indications may be combined in particular embodiments. Further, while advantages associated with certain embodiments have been described in the context of those embodiments, other embodiments may also exhibit such advantages, and not all embodiments need necessarily exhibit such advantages to fall within the scope of the present disclosure. Accordingly, the present disclosure and associated technology can encompass other embodiments not expressly shown or described herein.

I claim:

1. A method for reducing or eliminating pain in a patient, without causing paresthesia in the patient, the method comprising:
   programming a computer-readable medium of an implantable signal generator to:
      generate a non-paresthesia-producing therapy signal, wherein at least a portion of the therapy signal is at a frequency of from 2 Hz to 1,000 Hz, with a pulse width in a pulse width range from 10 microseconds to 50 microseconds, and a current amplitude in a current amplitude range from 0.5 mA to 20 mA; and
      transmit the therapy signal to the dorsal column of the patient's spinal cord via a signal delivery device implanted in the patient's epidural space and electrically coupled to the implanted signal generator.

2. The method of claim 1, wherein the therapy signal has a duty cycle.

3. The method of claim 2, wherein the duty cycle is 100%.

4. The method of claim 2, wherein the duty cycle is 50-100%.

5. The method of claim 2, wherein the frequency is applied throughout the length of an on period in the duty cycle.

6. The method of claim 2, wherein the frequency is applied during a portion of an on period in the duty cycle.

7. The method of claim 1, wherein the therapy signal has a current amplitude of about 2.5 mA.

8. The method of claim 1, wherein at least a portion of the therapy signal is a square-wave signal.

9. The method of claim 1, wherein the signal delivery device is a percutaneous lead.

10. The method of claim 1, wherein the signal delivery device is a paddle lead.

11. The method of claim 1, wherein the signal delivery device is an elongated lead having one or more electrodes.

12. The method of claim 1, wherein the signal delivery device is an elongated lead having a bipole arrangement of electrodes.

13. The method of claim 1, wherein programming the computer-readable medium includes programming the computer-readable medium to transmit the therapy signal to modulate glial cell activity at the patient's spinal cord.

14. The method of claim 1, wherein the pulse width is in a pulse width range from 20 microseconds to 40 microseconds.

15. The method of claim 1, wherein the current amplitude is in a current amplitude range from 0.5 mA to 7 mA.

16. The method of claim 1, wherein the current amplitude is in a current amplitude range from 0.5 mA to 5 mA.

17. The method of claim 1, wherein the current amplitude is in a current amplitude range from 0.5 mA to 2 mA.

18. A spinal cord stimulation system for reducing or eliminating pain in a patient, the system comprising:
   an implantable signal generator programmed to generate a non-paresthesia-producing therapy signal, wherein at least a portion of the therapy signal is at a frequency of from 2 Hz to 1,000 Hz, with a pulse width in a pulse width range from 10 microseconds to 50 microseconds, and a current amplitude in a current amplitude range from 0.5 mA to 7 mA; and
   a signal delivery device electrically coupled to the implantable signal generator to deliver the therapy signal to the dorsal column of the patient's spinal cord.

19. The system of claim 18, wherein the implantable signal generator generates the therapy signal at a duty cycle.

20. The system of claim 19, wherein the duty cycle is 100%.

21. The system of claim 19, wherein the duty cycle is 50-100%.

22. The system of claim 19, wherein the frequency is applied throughout the length of an on period in the duty cycle.

23. The system of claim 19, wherein the frequency is applied during a portion of an on period in the duty cycle.

24. The system of claim 18, wherein the therapy signal is delivered at a current amplitude of 2.5 mA.

25. The system of claim 18, wherein at least a portion of the therapy signal is a square-wave signal.

26. The system of claim 18, wherein the signal delivery device is a percutaneous lead.

27. The system of claim 18, wherein the signal delivery device is a paddle lead.

28. The system of claim 18, wherein the signal delivery device is an elongated lead having one or more electrodes.

29. The system of claim 18, wherein the signal delivery device is an elongated lead having a bipole arrangement of electrodes.

* * * * *